United States Patent [19]
Buechler et al.

[11] Patent Number: 5,824,799
[45] Date of Patent: Oct. 20, 1998

[54] HYBRID PHTHALOCYANINE DERIVATIVES AND THEIR USES

[75] Inventors: Kenneth F. Buechler, San Diego; Joseph B. Noar, Solana Beach; Lema Tadesse, San Diego, all of Calif.

[73] Assignee: Biosite Diagnostics Incorporated, San Diego, Calif.

[21] Appl. No.: 620,597

[22] Filed: Mar. 22, 1996

Related U.S. Application Data

[63] Continuation-in-part of Ser. No. 274,534, Jul. 12, 1994, and a continuation-in-part of Ser. No. 138,708, Oct. 18, 1993, abandoned, and a continuation-in-part of Ser. No. 126,367, Sep. 24, 1993, abandoned, and a continuation-in-part of Ser. No. 311,098, Sep. 23, 1994, and a continuation-in-part of Ser. No. 409,825, Mar. 23, 1995.

[51] Int. Cl.⁶ .......................... C09B 47/00; C09B 47/30; C07D 487/22
[52] U.S. Cl. .............................. 540/128; 540/122
[58] Field of Search ................... 540/122, 128, 540/129

[56] References Cited

U.S. PATENT DOCUMENTS

| | | | |
|---|---|---|---|
| 3,996,345 | 12/1976 | Ullman et al. | 424/12 |
| 4,166,105 | 8/1979 | Hirschfield | 424/8 |
| 4,199,363 | 4/1980 | Chen | 430/512 |
| 4,199,559 | 4/1980 | Ullman et al. | 424/8 |
| 4,326,008 | 4/1982 | Rembaum | 428/403 |
| 4,368,258 | 1/1983 | Fujiwhara et al. | 430/493 |
| 4,420,568 | 12/1983 | Wang et al. | 436/536 |
| 4,476,229 | 10/1984 | Fino et al. | 436/500 |
| 4,510,251 | 4/1985 | Kirkemo et al. | 428/403 |
| 4,542,104 | 9/1985 | Stryer et al. | 436/536 |
| 4,609,689 | 9/1986 | Schwartz et al. | 523/202 |
| 4,666,862 | 5/1987 | Chan | 436/501 |
| 4,777,128 | 10/1988 | Lippa | 435/5 |
| 5,039,798 | 8/1991 | Johnson | 540/123 |
| 5,055,414 | 10/1991 | Babb et al. | 436/501 |
| 5,089,391 | 2/1992 | Buechler et al. | 435/7.1 |
| 5,116,989 | 5/1992 | Hale et al. | 546/265 |
| 5,123,731 | 6/1992 | Yoshinaga et al. | 356/73 |
| 5,132,206 | 7/1992 | Dreyer | 435/6 |
| 5,154,887 | 10/1992 | Babb | 422/56 |
| 5,157,412 | 10/1992 | Kleinschmidt et al. | 346/1.1 |
| 5,187,288 | 2/1993 | Kang et al. | 548/110 |
| 5,194,393 | 3/1993 | Hugh et al. | 436/525 |
| 5,248,782 | 9/1993 | Haughland et al. | 548/110 |
| 5,274,113 | 12/1993 | Kang et al. | 548/405 |
| 5,326,692 | 7/1994 | Brinkley et al. | 435/6 |
| 5,403,928 | 4/1995 | Arrhenuis | 540/128 |
| 5,428,152 | 6/1995 | Hayashida et al. | 540/128 |
| 5,484,685 | 1/1996 | Tai et al. | 540/452 |

FOREIGN PATENT DOCUMENTS

| | | |
|---|---|---|
| 075982 | 4/1983 | European Pat. Off. ............ 33/58 |
| 076695 | 4/1983 | European Pat. Off. ............ 33/58 |
| 0285965 | 10/1988 | European Pat. Off. . |
| 0407188 | 1/1991 | European Pat. Off. ............ 33/58 |
| 0597389 | 5/1994 | European Pat. Off. . |
| 880477 | 6/1988 | WIPO . |
| 9118007 | 11/1991 | WIPO . |
| 9319366 | 9/1993 | WIPO . |
| 9323492 | 11/1993 | WIPO . |
| 9508772 | 3/1995 | WIPO . |

OTHER PUBLICATIONS

Cerfontain and Kort, "Electrophilic Aromatic Sulfonation with Acidic Sulfonating Reagent," *Int. J. Sulfur Chem.* C6:123–136 (1971).
Cerfontain and Kort, *Mechanistic Aspects in Aromatic Sulfonation and Desulfonation*, Interscience, New York, pp. 2–5, 68–79 and 121–126 (1968).
Cook et al., "Octa–alkoxy Phthalocyanine and Naphthalocyanine Derivatives: Dyes with Q–Band Absorption in the Far Red or Near Infrared," *J. Chem. Soc. Perkin Trans. I* pp. 2453–2458 (1988).
Eldred and Young, "Dichlorofumaric Acid," *J. Am. Chem. Soc.* 75:4338–4339 (1953).
Förster, "Zwischenmolekulare Energiewanderung und Fluoreszenz," *Ann. Physik.* 2:55–75 (1948).
Gilbert, *Sulfonation and Related Reactions*, Interscience, New York, pp. 102–103, 306–307 and 339–383 (1965).
Gregoriadis (editor), *Liposome Technology*, vol. III, CRC Press Inc., p. 19 (1984).
Haughland et al., "Dependence of the Kinetics of Singlet–Singlet Energy Transfer on Spectral Overlap," *Proc. Natl. Acad. Sci. USA* 63:23–30 (1969).
Haughland, "Potential Sensitive Probes," *Handbook of Fluorescent Probes and Research Chemicals*, 5th edition, Molecular Probes, Inc., pp. 156–158 (1992–1994).
Hemmila, *Applications of fluorescence in immunoassays*, John Wiley & Sons, Inc., pp. 131–135 (1991).
Ikeda et al., "Synthesis of Non–Symmetrically Benzo–Substituted Phthalocyanines and Their Electronic Spectra,"0 *Chemistry Letters* pp. 763–766 (1992).
Kirby and Gregoriadis, "Ch. 2—A Simple Procedure For Preparing Liposomes Capable of High Encapsulation Efficiency Under Mild Conditions," *Liposome Technology*, vol. I, Gregoriadis editor, CRC Press Inc., pp. 20–26 (1984).
Kobayashi et al., "Synthesis, Spectroscopy, Electrochemistry and Spectroelectrochemistry of a Zinc Phtalocyanine with $D_{2h}$ Symmetry," *Chemistry Letters* pp. 2031–2034 (1992).

(List continued on next page.)

*Primary Examiner*—Mukund J. Shah
*Assistant Examiner*—Pavanaram K. Sripada
*Attorney, Agent, or Firm*—Lyon & Lyon LLP

[57] ABSTRACT

Water soluble hybrid phthalocyanine derivatives useful in competitive and noncompetitive assays immunoassays, nucleic acid and assays are disclosed and claimed having (1) at least one donor subunit with a desired excitation peak; and (2) at least one acceptor subunit with a desired emission peak, wherein said derivative(s) is/are capable of intramolecular energy transfer from said donor subunit to said acceptor subunit. Such derivatives also may contain an electron transfer subunit. Axial ligands may be covalently bound to the metals contained in the water soluble hybrid phthalocyanine derivatives. Ligands, ligand analogs, polypeptides, proteins and nucleic acids can be linked to the axial ligands of the dyes to form dye conjugates useful in immunoassays and nucleic acid assays.

22 Claims, 8 Drawing Sheets

OTHER PUBLICATIONS

Kobayashi et al., "Benzene or Naphthalene Ring–fused Mono–Substituted Type Tetraazaoctaphenylporphyrin Zinc Complexes," *Chemistry Letters* pp. 1567–1570 (1992).

Kobayashi et al., "New Route to Unsymmetrical Phtalocyanine Analogues by the Use of Structurally Distorted Subphtalocyanines," *J. Am. Chem. Soc.* 112:9640–9641 (1990).

Kobayashi et al., "Phtalocyanines of a Novel Structure: Dinaphthotetraazaporphyrins with $D_{2h}$ Symmetry," *Inorg. Chem.* 33:1735–1740 (1994).

Konami et al., "Electronic spectra of benzo–substituted phthalocyanines," *Molecular Physics* 80:153–160 (1993).

Mayhew et al., "Ch. 2—Preparation of Liposomes Entrapping Cancer Chemtherapeutic Agents for Experimental In Vivo and In Vitro Studies," *Liposome Technology*, vol. II, Gregoriadis editor, CRC Press Inc., pp. 19–31 (1984).

McHugh and Gouterman, "Porphyrins XXIV. Energy, Oscillator Strength, and Zeeman Splitting Calculations (SCMO–CI) for Phthalocyanine, Prophyrins, and Related Ring Systems," *Theoret. Chim. Acta* (Berlin) 24:346–370 (1972).

Mikhalenko et al., "Pthalocyanines and Related Compounds," *J. Org. Chem.* (USSR (English Translation) 8:341–343 (1972).

Molecular Probes Ad entitled "Novel Fluorescent Latex Microspheres—Transfluospheres a Breakthrough in Latex Microsphere Technology" (1994).

Pariser et al., "A Semi–Empirical Theory of the Electronic Spectra and Electronic Structure of Complex Unsaturated Molecules. II," *J. Chem. Phys.* 21:767–776 (1953).

Pekcan et al., "Energy–Transfer Studies on Doped and Labeled Polymer Latex Particles," *Physical Review Letters* 61:641–644 (1988).

Pople, "Electron Interaction in Unsaturated Hydrocarbons," *Trans. Faraday Soc.* 49:1375–1385 (1953).

Stryer, "Fluorescence Energy Transfer as a Spectroscopic Ruler," *Annual Review of Biochemistry* 47:819–846 (1978).

Van Arman et al., "General Fluorescence Assay for Enzyme– Catalyzed Polyanion Hydrolysis Based on Template–Directed Excimer Formation. Application to Heparin and Polyglutamate," *J. Am. Chem. Soc.* 112:5376–5377 (1990).

Wheeler et al., "A Silicon Phthalocyanine and Silicon Napthalocyanine: Synthesis, Electrochemistry and Electrogenerated Chemiluminescence," *J. Am. Chem. Soc.* 106:7404–7410.

PHTHALOCYANINE

NAPHTHALOCYANINE

ANTHRANYLOCYANINE

SILICON PHTHALOCYANINE

SILICON NAPHTHALOCYANINE

SILICON ANTHRACYANINE

HYBRID PHTHALOCYANINE DERIVATIVES AND THEIR USES

REFERENCE TO RELATED APPLICATIONS AND PATENTS

This application is a continuation in part of application Ser. No. 08/274,534 filed Jul. 12, 1994 pending, and of application Ser. No. 08/138,708 filed Oct. 18, 1993 now abandoned, and of application Ser. No. 08/126,367 filed Sep. 24, 1993 now abandoned, and of application Ser. No. 08/311,098 filed Sep. 23, 1994 pending, and of application Ser. No. 08/409,825, filed Mar. 23, 1995 pending, from each of which priority is claimed. All of these applications are hereby fully incorporated by reference herein.

TECHNICAL FIELD

This invention relates generally to the synthesis of novel dyes and labels and methods for the detection or visualization of analytes and more specifically to fluorescent latex particles which incorporate the novel fluorescent dyes and utilize, in certain aspects, fluorescence energy transfer and intramolecular energy transfer, for the detection of analytes in immunoassays or in nucleic acid assays.

BACKGROUND ART

Various methodologies are available for the visualization of cells or molecules in cells and for the measurement of analyte concentrations in fluids. Fluorescence microscopy utilizes fluorescent dyes, generally connected to specific probes, such as antibodies, for the localization of proteins and complexes in cells. For the measurement of analyte concentrations, immunoassays have become popular over the last 40 years because of the specificity of antibodies toward the analyte or target ligand. Radio immunoassays were developed because the high specific activity of the radionucleotide allowed measurement of very low concentrations of analyte. However, because of the concerns for the environment and human health, the use of radionucleotides in immunoassays is becoming less popular. The use of enzymes in immunoassays to amplify a signal has been a very important advance in the field of immunoassays because their use does not involve environmental or human health hazards or risks. Enzyme-linked immunoassays, however, can be problematic because the activity of the enzyme is temperature dependent and the instability of the enzyme or the substrates can result in inaccurate quantitation of the target ligand. Still other immunoassays monitor fluorescence as the signal, with or without enzymes, for the measurement of analyte concentrations.

The characteristics of the fluorescent dyes are very important when quantifying analyte concentrations in biological fluids. For example, when the biological fluid is blood, serum or plasma, the intrinsic fluorescence of the fluid precludes the use of many dyes. These biological fluids generally have fluorescence emissions up to 600 nm when exciting at various wavelengths above 200 nm. The fluorescence is generated by excitation of the dye at the appropriate wavelength. The fluorescent signal is measured by a fluorometer which is tuned to excite the fluorescent molecule at a specific wavelength and to measure the emission of fluorescence at another wavelength. The difference in the excitation and emission wavelengths is referred to as the Stokes shift. To achieve the most sensitive measurement, the emission wavelength of the sample should not interfere with the emission of the dye. Also, the Stokes shift should be as large as possible so that the excitation light is not seen by the detector as a background signal. When the Stokes shift is not large, filters or monochromators can be utilized in the fluorometer to exclude light near the emission wavelength; however, the use of filters decreases the yield of light reaching the detector and generally one circumvents this problem of light loss by the use of high intensity lamps. Thus, to avoid problems associated with small Stokes shifts and dyes which emit near the intrinsic emission of the biological fluid, a sophisticated instrument is generally built. With the advent of near-patient diagnostics in hospitals, there is a need for portable, simple fluorometers which can assess fluorescence in an immunoassay for the detection of analytes in biological samples.

Another problem associated with the assay of analytes in fluids or the visualization of cellular components with an intrinsic fluorescence is that of selection of the dye which is utilized as the label. The dye is generally chosen for its brightness (the product of fluorescence quantum yield and extinction coefficient) since a certain sensitivity in the assay or the visualization technique is required. However, the selection of the dye used as the label is limited when the sample has an intrinsic fluorescence because the instrument may not be capable of distinguishing sample fluorescence from dye fluorescence.

The current invention provides a methodology for the development of amplified fluorescent label systems which can be tuned to specific excitation and emission wavelengths. The methodology teaches improved methods for incorporation of dyes into particles to minimize fluorescence quenching and to maximize fluorescence intensities of the dye molecules in the particles. In addition, the design and synthesis of novel hybrid phthalocyanine derivatives are described which are incorporated into particles or are synthesized as water-soluble molecules for use as labels and are directly coupled to proteins, polypeptides, other labels, nucleic acids and the like. The novel dye systems can be utilized for the quantitation of analytes in fluids, and in particular, in biological fluids. The novel dye systems can be tuned to specific exciting and emitting wavelengths so that low current sources, such as light emitting diodes and laser diodes, and detectors, such as photo diodes, and the like, can be used in the manufacture of fluorometers which can be battery powered and portable, for use, for example, in immunoassays dedicated to near-patient diagnostics.

DISCLOSURE OF THE INVENTION

This invention relates to novel fluorescent particles and novel water soluble fluorescent dyes. These novel particles and dyes can be tuned to specific excitation and emission wavelengths to accommodate a wide variety of assay or visualization systems. In yet another aspect of the invention, the methodology teaches improved methods for incorporation of dyes into particles to minimize fluorescence quenching and to maximize fluorescence intensities of the dye molecules in the particles through the use of different dye molecules which possess the same or very similar excitation and emission wavelengths.

Many novel phthalocyanine derivatives and hybrid phthalocyanine derivatives are disclosed and claimed. In one embodiment microparticles are disclosed having at least one hybrid phthalocyanine derivative, said derivative(s) having (1) at least one donor subunit with a desired excitation peak; and (2) at least one acceptor subunit with a desired emission peak, wherein said derivative(s) is/are capable of intramolecular energy transfer from said donor subunit to said acceptor subunit.

In another embodiment, water soluble hybrid phthalocyanine derivatives are disclosed having (1) at least one donor subunit with a desired excitation peak; and (2) at least one acceptor subunit with a desired emission peak, wherein said derivative(s) is/are capable of intramolecular energy transfer from said donor subunit to said acceptor subunit. Such derivatives also may contain an electron transfer subunit. Axial ligands may be covalently bound to the metals contained in the hybrid phthalocyanine derivatives. The axial ligands of the dyes can be further elaborated with drug analogues and compounds, proteins, polypeptides and nucleic acids. Numerous compounds capable of intramolecular energy transfer as well as compounds for fluorescence energy transfer are claimed.

MODES FOR CARRYING OUT THE INVENTION

Figure 1:
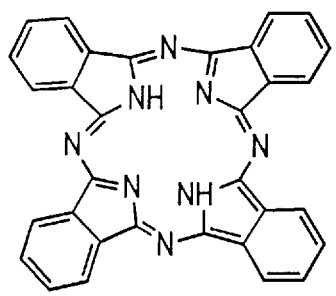
FIG. 1 depicts the structures of phthalocyanine, naphthalocyanine and anthranylocyanine.
Figure 1:
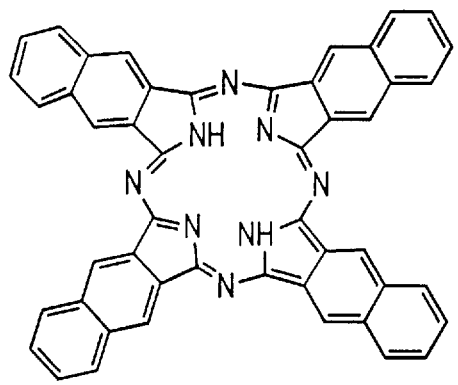
Figure 1:
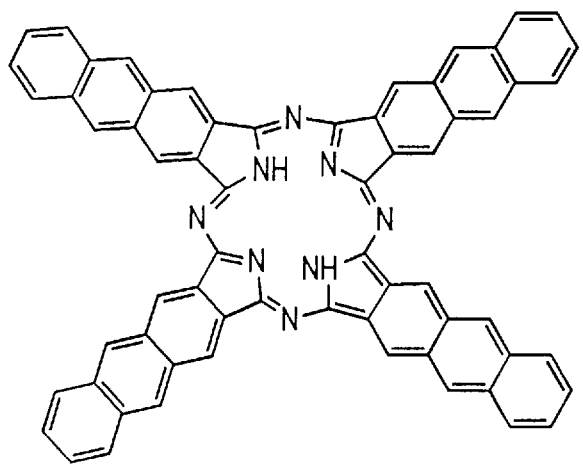

This invention describes novel fluorescent particles and novel fluorescent molecules and diagnostic methods for their use. Developing a method for the visualization of a cellular component or a cell or for an assay which utilizes a fluorescent dye and which quantifies an analyte in a sample requires the use of a fluorometer. The fluorescent label, the sample and the instrument must be compatible with each other to achieve an accurate measurement. Several criteria for a fluorescent label as they relate to the sample and instrument are described below. First, the absorption or excitation and emission wavelengths of the dye should not correspond so closely to the absorption or fluorescence of the specimen or sample such that the sample affects the fluorescence measurement of the dye. Second, the Stokes shift of the dye should be as large as possible to minimize the measurement of background from the excitation wavelength. Third, the dye must be compatible with the phase of the visualization or the fluid phase of the assay; that is, the dye must be water soluble or water insoluble depending on the visualization or assay format. Fourth, the dye should be as bright as is necessary to achieve the desired sensitivity. Brightness is the product of the extinction coefficient and the quantum yield of the dye. Fifth, the instrument used to detect the fluorescent signal is generally designed around the specifications of the dye and the specimen or sample being visualized or assayed.

These points will be discussed in more detail and illustrate some of the intricacies in developing a fluorescent visualization technique or an assay using fluorescent dyes. One is limited either to dyes which have been synthesized or ones which must be synthesized in order to meet the above criteria. Using prior art methods, a very limited range of excitation and emission wavelengths can be planned for a specific molecule. The teachings of this invention allow one to prepare fluorescent dyes and labels which can be tuned to many excitation and emission wavelengths allowing for large Stokes shifts. Thus, designing a dye system with the specifications of the sample or specimen and the instrument is possible from the teachings of this invention, as opposed to the prior art methods which involve designing the instrument around the specifications of the dye. Tuning the dye system to accommodate the characteristics of the sample and the instrument results in an improved visualization process for the assay.

The excitation and emission wavelengths of the dye should not correspond to those of the sample being assayed or visualized, otherwise the sample can interfere with the measurement of the fluorescent signal. When absorption or emission wavelengths of the sample do correspond to those of the dye, in practice, one dilutes, for example, a serum or blood sample so that the interference by the sample is reduced or the interfering sample is washed away from the detection area. Indeed, currently, there is no fluorescent assay system on the market for the measurement of analytes in neat biological fluids, particularly blood, plasma or serum. One reason for the lack of fluorescent assay systems which detect analytes in neat samples is that no good fluorescent dye exists which meets all the criteria listed above, particularly for measuring fluorescence in biological samples. When the sample absorbs significantly at the excitation wavelength the amount of light which excites the sample is thus affected by the variation in the sample characteristics. For example, serum, plasma, or blood from different individuals will be different in their relative absorptivities, which differences translate into different intensities of excitation light used to excite the fluorescent label. The fluorescence emission of the dye is directly proportional to the intensity of the incident light, such that when the sample absorbs a portion of the incident light, the intensity of the fluorescent signal will vary accordingly. This results in measuring an incorrect or effected fluorescence emission. In addition, the emission wavelength of the dye should not correlate with the emission or absorbance of the sample because the sample will increase the measured fluorescence of the dye or the sample will absorb all or a portion of the dye fluorescence and also result in an incorrect or effected fluorescence emission. These problems are avoided when the sample is invisible to the excitation and emission wavelengths.

Figure 8:
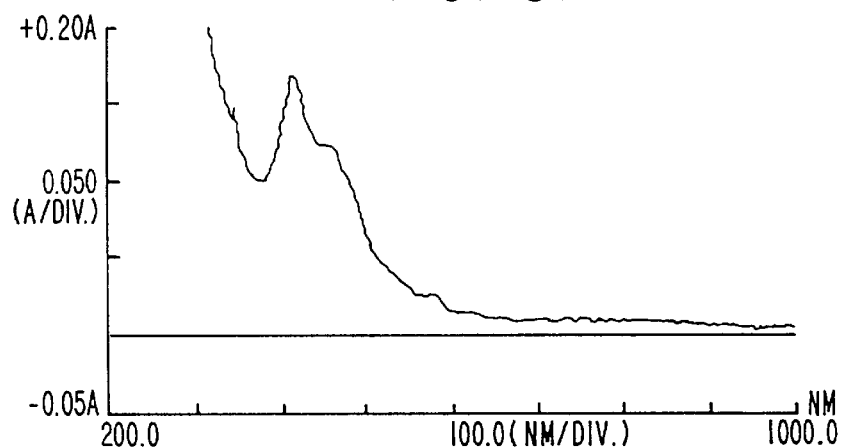
FIG. 8 depicts the absorbance spectrum of human serum between 200 nm and 1000 nm.
Figure 10:
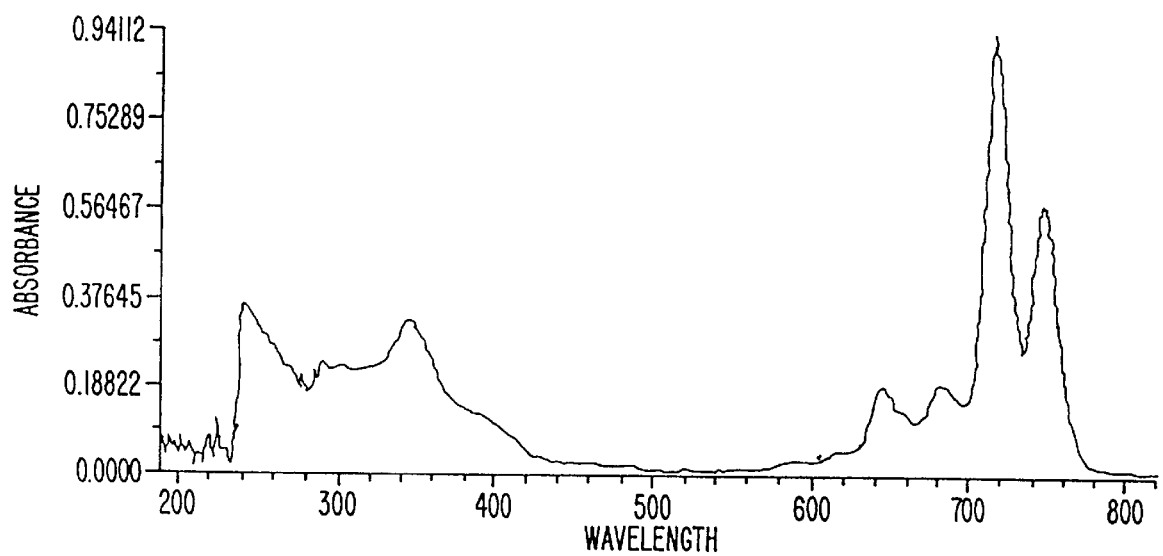
FIG. 10 depicts the spectrum of Silicon [di(1,6-diphenylnaphthalocyanine)] diphthalocyanine bis (dimethylhexylvinylsilyloxide).

FIG. 8 shows the spectrum between 200 nm and 1000 nm of human serum. Wavelengths above 600 nm absorb considerably less than those between 200 nm and 600 nm. Thus, both the absorption of the incident light and the effect on the fluorescence of a dye are minimal when exciting above 600 nm. Preferred excitation wavelengths for biological fluids, including urine, blood, serum or plasma is 600 nm or greater. Particularly preferred excitation wavelengths above 600 nm are those which correspond to the maximum light output of laser diodes and light emitting diodes. Preferred emission wavelengths are those above 600 nm. The intrinsic sample fluorescence can cause a high background signal if the emission wavelength of the dye and the sample are overlapping. In addition, the scattered light of the excitation source can also contribute to the background signal. The contribution of scattered light to the background can be seen, for example, in FIG. 5. In general, the magnitude of the scatter is inversely proportional to the fourth power of the measured wavelength. This teaches that desired emission wavelengths are in the near-infrared or in the infrared region of the spectrum. The inventive teachings described herein provide for dyes and dye systems which excite above 600 nm and which emit above 650 nm and more preferred, above 730 nm.

The Stokes shift of the dye should be as large as possible to minimize the measurement of background from the excitation source so that the signal-to-background ratio at the limit of sensitivity is maximized. A large Stokes shift, however, will only maximize the efficiency of the fluorescence measurement and may not always result in an accurate fluorescence measurement. For example, table 3 shows data from several dye systems which were excited between 420 nm and 670 nm in either buffer, undiluted human serum and blood. The fluorescence intensity of the first dye system (line 1, table 1), when excited at 475 nm in serum and blood, is only 7.6% and 13%, respectively, of the intensity in buffer even though the Stokes shift is 205 nm. The second dye system (line 4, table 1), excited at 420 nm, is 28% and 4% in serum and blood of the intensity in buffer, respectively, with a 260 nm Stokes shift. The third and fourth dye systems (line 60 and line 59, table 1), excited at 670 nm and 650 nm and with 110 nm and 130 nm Stokes shifts, respectively, have fluorescence intensities which are comparable in buffer and in serum. The fifth dye system (line 107, table 1), excited at 670 nm with a 90 nm Stokes shift, has fluorescence intensities which are also comparable in buffer, serum and blood. The sixth dye system, which is a hybrid phthalocyanine derivative (line 1, table 2), has comparable fluorescence intensities in buffer, serum and blood when excited at 646 nm with a Stokes shift of 114 nm. The data show that the fluorescence intensity is greatly affected when the excitation wavelength is within the range of the absorbance of the sample in which the measurement is made. The data also show that the magnitude of the Stokes shift does not have an influence on the accuracy of the measurement. These data are representative of other dyes and dye systems which are excited at a wavelength where the sample absorbs. The effect of the decreased fluorescence emission is not a result of the emission wavelength (that is, 680 nm or 780 nm) because the samples absorb minimally at 680 nm and 780 nm. One skilled in the art can appreciate, that with the inventive teachings described herein, the wavelengths for excitation and emission of a dye system should be a function more of the absorption and emission characteristics of the sample rather than selecting only a dye system with a large Stokes shift.

The availability of dyes with Stokes shifts greater than 100 nm is greatly limited, particularly when the excitation wavelength is greater than 600 nm. To further limit the usefulness of available dyes, the solubility of the dyes in aqueous samples can be a problem because most dyes with large Stokes shifts are water insoluble.

The problem of a dye possessing a small Stokes shift is usually overcome in the engineering of the fluorometer by the use of monochromators or expensive optics which filter out the light from the excitation source. However, to overcome the loss in light intensity due to the filters, for example, one requires the use of high powered light sources. These light sources produce heat which must be dissipated in an instrument by using heat sinks or fans. The complexity of the fluorescence measuring device, both from an optical and a mechanical perspective, is thus greatly affected by the inadequacies of the dye system. With the advent of near-patient testing in hospitals and emergency departments, instruments which measure fluorescence in immunoassays will be required to be portable and uncomplicated to the technician. Thus, the future state of the art for the manufacture of, for example, fluorometers which are employed for immunoassays will be required to change to simple and portable instruments. The high powered light sources and expensive optics currently incorporated into fluorometers will not meet the requirements for small, portable instruments.

The instant invention teaches that fluorescent labels can be prepared with large Stokes shifts and be tuned to wavelengths both of which are compatible with excitation sources and emission detectors and which are compatible with the absorption and emission of the sample, for example, blood, serum, plasma, urine, ground water, and the like. The excitation and emission wavelengths of the novel fluorescent dyes and particles can generally be varied independently of each other.

The dye must be compatible with the fluid phase of the assay, or in other words, the dye must be water soluble or water insoluble depending on the visualization or assay format. Many fluorescent dyes are water insoluble or poorly water soluble and these dyes are not easily used for labeling molecules, proteins, nucleic acids or cells. One skilled in the art will recognize that water insoluble dyes can be incorporated into latex particles as described in U.S. Pat. Nos. 4,326,008, 4,609,689 and 5,154,887, which are hereby incorporated by reference. Thus, water insoluble dyes can be made useful by incorporation into latex particles for visualization in a variety of assay formats.

The dye should be as bright as is necessary to achieve the desired sensitivity. If one knows the extinction coefficient and the quantum yield of the dye and the concentration of the target to be measured, it can be estimated whether the dye is bright enough to achieve the desired sensitivity. Incorporation of dyes into latex particles or the utilization of an enzyme which catalyzes the production of a fluorescent substrate are examples of techniques which one skilled in the art uses as amplification systems.

The instrument used to detect the fluorescent signal is generally designed around the specifications of the dye and the specimen or sample being visualized or assayed because of the limited numbers of dyes which can be successfully used. As discussed above, the components of the instrument are selected for a particular dye system since a useful instrument must be highly tuned to eliminate the light from the excitation source.

Each of the conditions described above impose limitations on dye systems which can be employed for measuring sub-picomolar concentrations of analytes, particularly in biological fluids. The limitations also impose restrictions on the design of an instrument to measure the fluorescence. The novel teachings of the instant invention allow the design, synthesis and tuning of dye systems to match, generally, nearly any instrument design.

Several inventive teachings are described for tuning excitation and emission wavelengths of dyes so that the excitation and emission are compatible with the sample matrix in which the fluorescence is measured and the instrument for quantifying the fluorescence. One teaching is to either incorporate or adsorb at least two dyes into or onto particles, which, as a pair, exhibit fluorescence energy transfer. The particles which can be used are those which adsorb dyes on the surface or absorb or imbibe dyes inside the particle. Another teaching is to incorporate dyes which are covalently attached to each other and which also exhibit fluorescence energy transfer both in solution and in particles.

Another teaching is to incorporate hybrids of phthalocyanines, naphthalocyanines, anthranylocyanines (collectively termed hybrid phthalocyanine derivatives) and various derivatives of these classes of compounds which have different subunits depending on the desired excitation or emission wavelengths. The hybrid phthalocyanine derivatives may also be synthesized as water soluble compounds to be used for direct attachment to proteins, polypeptides other labels or nucleic acids. One advantage of hybrid phthalocyanine derivatives is that they allow one to create dyes and dye systems which have greater Stokes shifts with higher extinction coefficients at the excitation wavelength. This is accomplished by properly selecting the subunits which are to be tetramerized to form the hybrid phthalocyanine derivative structure and which will absorb the light at the excitation wavelength.

The selection of dye pairs for incorporation into particles is based on their ability to exhibit energy transfer (singlet-singlet energy transfer) at the appropriate excitation wavelength of the donor dye and the emission of the acceptor. Fluorescence energy transfer of two molecules is well known to those skilled in the art and the rate of energy transfer is described by Forster in Ann. Physik. (1948) 2,55–75. Fluorescence energy transfer has been used as a spectroscopic ruler to predict proximity relationships in proteins, RNA and peptides (Annual Review of Biochemistry (1978), 47, 819–846) and also to probe geometrical details in particles (Physical Review Letters (1988) 61, 641–644). U.S. Pat. No. 5,326,692 describes fluorescent particles with controllable enhanced Stokes shifts. U.S. Pat. Nos. 4,542,104 and 4,666,862 describe fluorescence energy transfer in phycobiliproteins. These dye complexes are described for use as labels in immunoassays. The limited use, however, of phycobiliproteins and the expense of these natural protein complexes make them undesirable for use on a commercial scale. Some unsymmetrical or hybrid phthalocyanines have been described, for example, in J. Am. Chem. Soc. 1990, 112, 9640–9641, Chemistry Letters 1992, 2031–2034 and Inorg. Chem. 1994, 33, 1735–1740, but this invention greatly expands the compounds which can be synthesized for use in immunodiagnostics to achieve adequate fluorescence intensities and desired excitation and emission characteristics. The ratio of the various diiminoisoindiline or dicarbonitrile precursors and their substitution by electron donating or electron withdrawing groups in the synthesis of the hybrid phthalocyanines, naphthalocyanines and anthranylocyanines will affect the absorption spectrum and the excitation and emission wavelengths of the compounds. This is taught and applied to the novel dyes herein.

In one aspect, the novel fluorescent particles of this invention are composed of at least two dyes which are positioned in the interior or on the exterior of particles at an energy exchanging distance. One skilled in the art will recognize that various particles can be utilized, such as latex, silica, alumina, liposomes, various colloids and the like. Particularly preferred particles are latex particles. The selection of the dye molecules for incorporation into the particles should be related to the specific use of the particles, the sample to be analyzed and the instrument for measuring the fluorescence. For example, when developing an assay for an analyte in a biological medium, such as blood, serum or a cell extract, the intrinsic absorbance and fluorescence of the sample must be considered. Serum and cellular components absorb in the ultraviolet spectrum as well as in the visible spectrum up to around 600 nm and the intrinsic fluorescence can broadly approach 600 nm. In addition, samples which contain small particles, such as dirt particles in ground water, lipoproteins in serum or blood, cells and cellular particles and components will scatter the excitation light which results in a higher background signal. The ideal dye couple would include the donor dye which would be excited or absorb at above 600 nm and emit at a wavelength which the acceptor dye absorbs, and the acceptor dye should emit at a wavelength above 600 nm. In the case of a single dye system, for example, with the use of hybrid phthalocyanine derivatives, the excitation and emission wavelengths should also be above 600 nm. The sample, for example, serum, then does not affect fluorescence of the acceptor dye because the sample poorly absorbs at the absorption of the donor dye and the acceptor dye emits at a wavelength where the sample does not absorb or fluoresce.

Fluorescent dye molecules incorporated into or onto particles will exhibit fluorescence quenching because of the close proximity of the dyes to each other and to the matrix of the particle. When loading dyes into or onto particles, one must optimize the concentration of dye as it relates to quenching. The dyes can be loaded successively or together. The degree of quenching can be quantified by measuring the fluorescence emission of a dilute suspension of particles (about 0.001% to 0.1% solids) in a buffer solution, in a buffered protein solution or in water and then also measuring the fluorescence of the same concentration of particles in solvent which liberates the dyes from the particles. The ratio of the fluorescence intensities (1 - [fluorescence intensity of incorporated dyes divided by the intensity of liberated dyes] is the degree of quenching of the dyes in the particle. In practice, one incorporates dyes at various concentrations and measures the fluorescence intensities of the incorporated and liberated dyes to optimize the intensity of fluorescence of the particle while minimizing the quenching of fluorescence in the particle. In a situation where more than one acceptor dye is used to minimize fluorescence quenching and to maximize fluorescence intensity, one may use different acceptor dyes which have emission peaks which are within about 25 nanometers of one another. The emission of both acceptor dyes may be useful if the fluorometer is set-up to measure a wide band pass of fluorescence, for example, about a 20 to 60 nm bandpass.

Another important consideration is the efficiency of the fluorescence energy transfer. In practice, if the energy transfer efficiency is not close to 100%, then one can observe the fluorescence of the donor dye. The resulting fluorescence of the donor dye can make the particles undesirable or even useless because the "effective Stokes shift" (that is, the shortest wavelength distance to a light source from the defined acceptor molecule emission wavelength in the fluorescence system) of the particles is now not the difference between the excitation and emission wavelengths of the donor and acceptor dyes, respectively, but rather the difference between the donor emission and the acceptor emission wavelengths. The emissions of the donor and acceptor wavelengths can overlap partially with each other when efficient energy transfer is not obtained and complicate the selection of filters for use in a fluorometer. The decrease in the energy transfer efficiency can also be directly related to a decrease in the emission of the acceptor dye, resulting in a particle which may not be as bright as a particle with efficient energy transfer. In addition, under conditions of inefficient energy transfer, slight changes in the sample or in solution conditions, for example, pH, ionic strength and the like, may affect the magnitude of energy transfer efficiency and thereby may affect the intensity of the fluorescent signal.

In selecting dye pairs for fluorescence energy transfer one begins by studying the overlap of the donor emission and acceptor excitation wavelengths. The dyes are positioned in the particle at an energy exchanging distance from one another which allows singlet-singlet energy transfer. Although a particular pair of dyes has acceptable overlapping excitation and emission wavelengths (for example, see Proc. Natl. Acad. Sci. USA 1969, 63, 23–30), they may not exhibit fluorescence energy transfer in particles or they may have suboptimal (less than 80%) efficiency of energy transfer. The process to determine whether 2 or more dyes will exhibit efficient energy transfer is through experimentation after the appropriate spectral overlap criteria are met. The efficiency of fluorescence energy transfer is determined by measuring the fluorescence intensity of the donor dye alone in particles and also measuring the fluorescence emission of the particles which have incorporated 2 or more dyes (that is, the fluorescent energy transfer particle) at the emission wavelength of the donor dye, both sets of particles having the same concentrations of donor dye and particles. The measured fluorescence at the donor dye emission wavelength of the fluorescent energy transfer particles divided by the fluorescence of the donor dye particles is the efficiency of fluorescence energy transfer. Ideally, in practice, the emission of the donor dye should be undetectable or only slightly detectable so that the effective Stokes shift is not reduced because of the donor dye emission. Preferred fluorescence energy transfer efficiencies are 80% or greater and particularly preferred fluorescence energy transfer efficiencies are 90% or greater.

Another important criteria for preparing partices exhibiting fluorescence energy transfer is the selection of the solvent used to swell and/or imbibe the dyes. The solvent system should penetrate the interior of the particle, for example, when using latex particles, and the dyes should also be soluble in the solvent system so that the dyes in the solvent can enter the interior of the particle. Optimization by experimentation is recommended, however, to produce particles with energy transfer or with optimum energy transfer. For example, table 6 of Example 67 shows the results of fluorescence energy transfer in latex particles prepared with dimethylformamide and tetrahydrofuran, both of which swell latex particles and dissolve the dyes.

When using particles which are not porous, for example, silica or alumina, for fluorescence energy transfer, the solvent system should dissolve the dyes but allow the dyes to adsorb to the particles. In some instances, it may be necessary to exchange solvent systems to adsorb the dyes; that is, the first solvent system dissolves the dyes in the particle slurry and a second solvent is introduced which promotes the adsorption of the dyes to the particles. When preparing liposomes which contain energy transfer dyes, ultrasonic techniques, for example, can be utilized to trap the dyes in the liposome interior as the liposome is formed. Techniques for forming liposomes can be found in, for example, *Liposome Technology*, Volumes I–III (1984), ed., G. Gregoriadis, CRC Press Inc.

The novel particles described herein exhibit reduced quenching and improved fluorescence intensities. A large majority of fluorescent molecules have aromatic character, that is, they possess $4n+2$ $\pi$ electrons. The resultant aromatic character promotes stacking of the molecules, especially of water insoluble molecules in aqueous solutions or in particles in aqueous solution, which in turn promotes fluorescence quenching. The novel particles described herein are incorporated with dyes which, through steric interference of the dye molecules, have a minimized propensity to stack in the particles.

In another aspect of this invention, fluorescence quenching of dye molecules in particles is minimized by employing different dyes with approximately the same excitation and emission wavelengths. That is, the wavelength maximum for excitation and/or emission of the different dyes is within about 25 nm of each other so that there is substantial overlap of the peaks. Different dyes will not stack in an organized orientation with each other to the same degree as dyes which are the same. Incorporating different dyes into or onto particles using organic solvents and then removing the solvent causes the dye to precipitate or crystallize in the particle. The disruption of the crystalline lattice of dye molecules in particles alters the stacking of the molecules and thereby reduce quenching. Thus, incorporation of dissimilar dye molecules with similar excitation and emission spectra improves fluorescence intensities of the particles by decreasing the quenching interactions of the molecules.

In another aspect of this invention, incorporation into particles of dissimilar dyes which exhibit fluorescence energy transfer in the particles may also disrupt the other's crystalline lattice formation. Thus, the fluorescence intensities of particles exhibiting fluorescence energy transfer will be improved as a result of decreasing quenching in the particle because the stacking of similar dyes in the particles is disrupted by the dissimilar dye.

In yet another aspect of this invention, the synthesis of phthalocyanine derivatives and hybrid phthalocyanine derivatives with axial ligands reduces the stacking of the aromatic ring system, thus minimizing the interactions between molecules and maximizing fluorescence intensities.

One skilled in the art can appreciate that more than one dye pair which exhibits fluorescence energy transfer can be incorporated into or onto particles resulting in a class of particles which fluoresce at different wavelengths. In addition, with the inventive teachings described herein, incorporation into or onto particles of 3 or more dyes, which together provide a cascade of energy transfer from the absorber(s) to the intermediate donor(s) to the acceptor(s) (which fluoresces), can result in the production of particles with very long Stokes shifts and allows one to produce particles with nearly an unlimited variety of excitation and emission characteristics.

Figure 2:
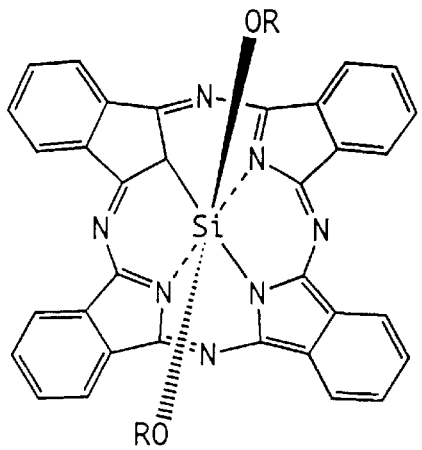
FIG. 2 depicts the structures of silicon phthalocyanine, silicon naphthalocyanine and silicon anthranylocyanine.
Figure 2:
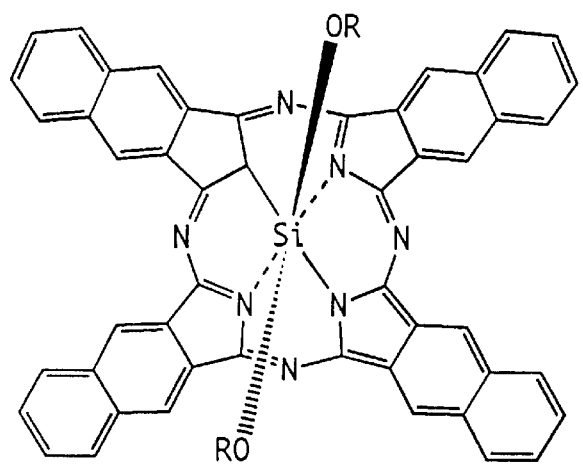
Figure 2:
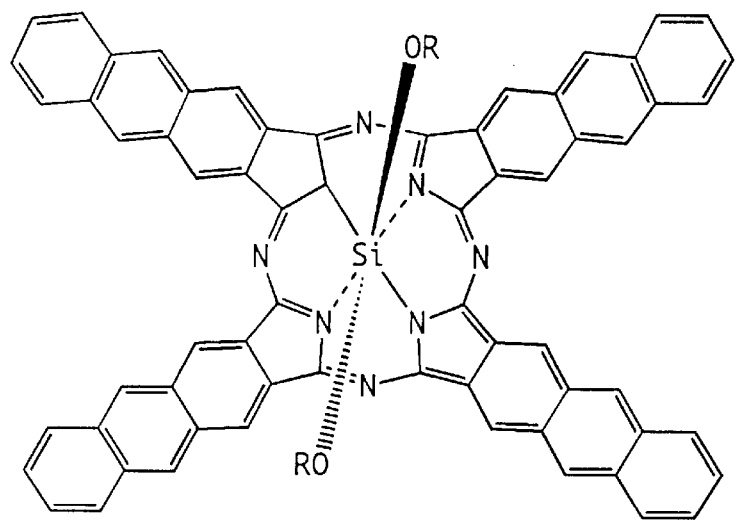

FIG. 1 shows preferred acceptor dyes which are phthalocyanines, naphthalocyanines and anthranylocyanines. FIG. 2 shows particularly preferred acceptor dyes which are derivatives of silicon phthalocyanines, naphthalocyanines and anthranylocyanines, where R is hydrogen or an alkylcarbon chain from 1–20 carbons, either saturated or unsaturated, having 0–10 heteroatoms (N,O,S), and having 0 or 1 siloxide groups. The best mode compounds are those in which R=

Si $(CH_3)_2C_6F_5$

S $(C_6H_{13})_3$

Si $(CH_3)_2(CH_2)_3CN$

Si $(CH_3)_2(CH_2)_{10}COOCH_3$

Si $(CH_3)_2CH=CH_2$
Si $(CH_3)_2(CH_2)_{10}COOH$
Si $(CH_3)_2(CH_2)_4Cl$; and
Si $(CH_3)_2(CH_2)_6CH=CH_2$.

Figure 3A:
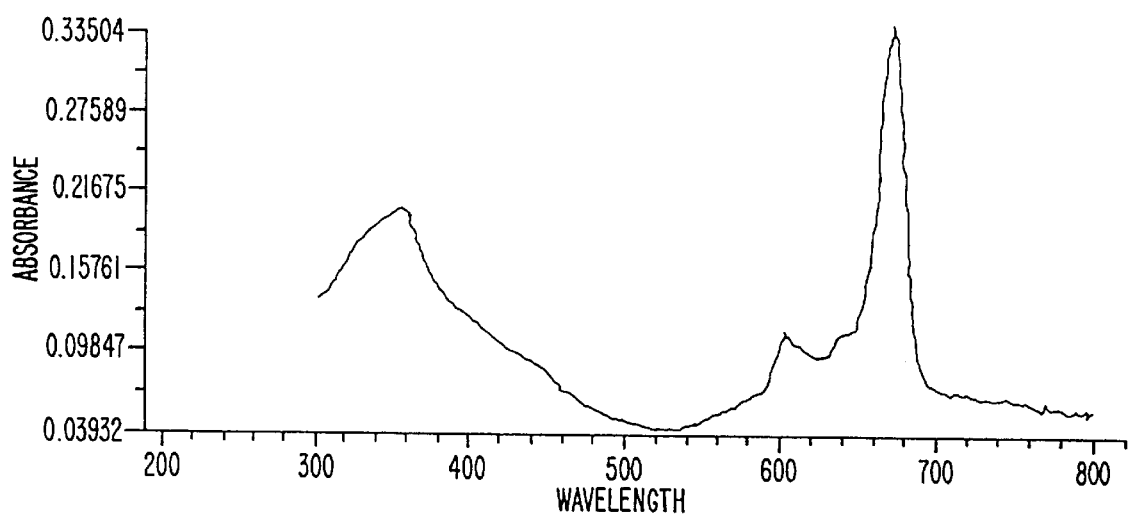
FIG. 3 depicts the spectra of silicon phthalocyanine dihydroxide and the spectra of silicon 2,3-naphthalocyanine dihydroxide.
Figure 3B:
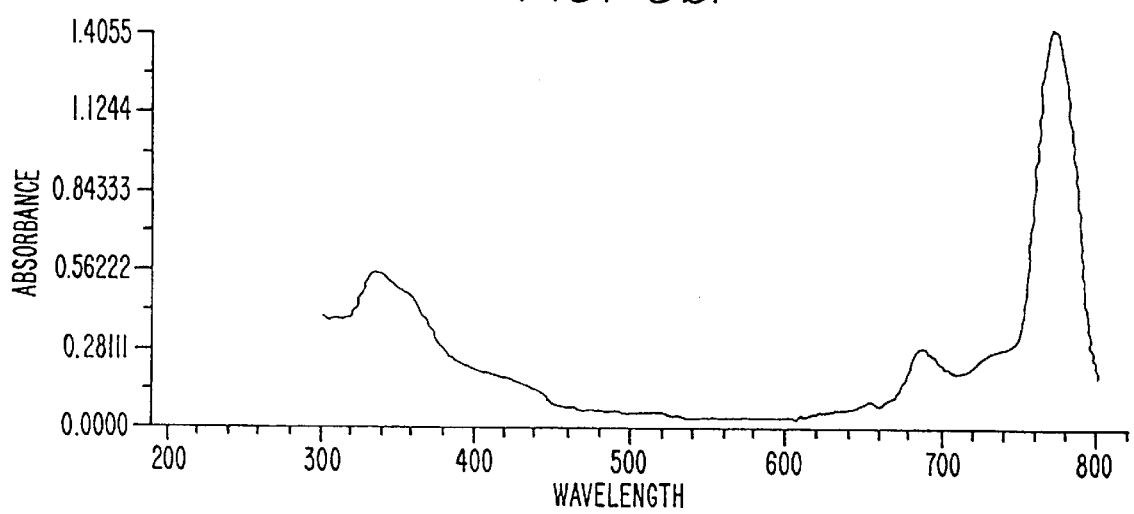
Figure 9:
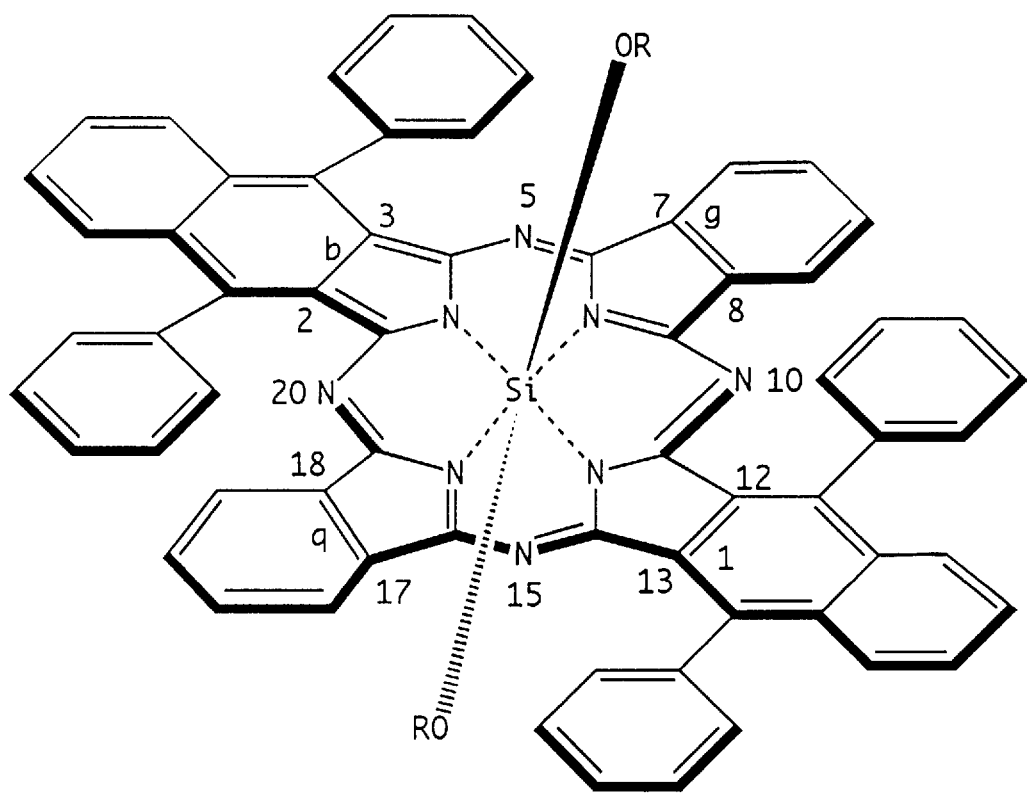
FIG. 9 depicts the structure of a novel hybrid phthalocyanine derivative, Silicon [di(1,6-diphenylnaphthalocyanine)] diphthalocyanine bis (dimethylhexylvinylsilyloxide).
Figure 9:
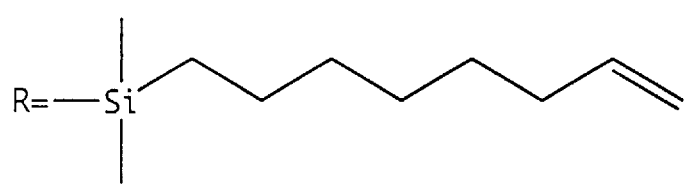

The parent compounds of the phthalocyanines and naphthalocyanines are preferred because their emission wavelengths are around 680 nm and 780 nm in latex particles, respectively. Also preferred parent compounds are the anthranylocyanines which have emissions around 850 to 900 nm. These three classes of preferred parent compounds will collectively be called "phthalocyanine derivatives" and may or may not have an included metal and may or may not have axial ligands. Also, preferred parent compounds include "hybrid phthalocyanine derivatives" which have 2 or more different subunits of the 4 total subunits and may or may not have an included metal and may or may not have axial ligands. An example of a hybrid phthalocyanine derivative containing a metal and an axial ligand is illustrated in FIG. 9. The emission wavelengths for the phthalocyanine derivatives or the hybrid phthalocyanine derivatives are particularly useful for quantifying fluorescence in biological samples and tissues and for minimizing the background scatter intensity. Those skilled in the art can appreciate that phthalocyanine derivatives and hybrid phthalocyanine derivatives can be synthesized, for example, by derivatization of the phenyl, naphthyl or anthranyl rings with various substitutes to yield different molecules. These variants are within the scope of the instant invention. Derivatives of tetraazaporphine are also within the scope of the instant invention. The derivatization of the aromatic structure of phthalocyanine derivatives and hybrid phthalocyanine derivatives can produce blue or red shifted excitation or emission wavelengths. The choice of the donor dye to excite the phthalocyanine or hybrid phthalocyanine derivatives is dependent on having a donor dye emission wavelength which corresponds to the appropriate range of absorbance wavelengths of the phthalocyanine or hybrid phthalocyanine derivative. FIG. 3 shows the absorbance spectra of the silicon dihydroxypilthalocyanine and silicon dihydroxynaphthalocyanine in dimethylformamide. A potential range of excitation of the these acceptor dyes by the donor dye is between approximately 550 nm and 670 nm and 600 nm and 760 nm, respectively. One skilled in the art will recognize that many dyes would be candidates for the donor dye because of the wide useful range of wavelengths which can excite the acceptor dyes. Indeed, the phthalocyanine derivative can be the donor for the naphthalocyanine derivative. The choice of the acceptor dye should meet the criteria outlined above. Several examples are described which illustrate the versatility of this novel approach.

If one wants to build an instrument with an excitation source which has a maximum intensity at 480 nm and a detector which has a good quantum efficiency at 600 to 700 nm, the donor dye should be capable of being excited at 480 nm. Assuming that a phthalocyanine derivative is the acceptor dye for emission at 680 nm, the donor should then emit in the range of 550 to 670 nm.

Preferred classes of dyes for this application are styryl, phenylbutadienyl and phenylhexatrienyl dyes. Styryl dyes are those of the following formula:

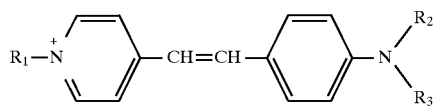

and phenylbutadienyl dyes are of the formula:

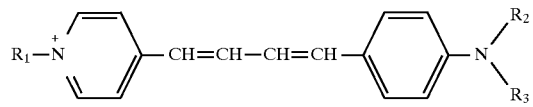

and phenylhexatrienyl dyes are of the formula:

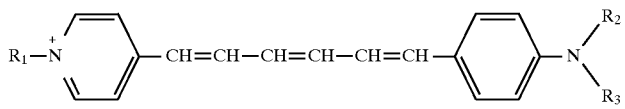

wherein R1, R2 and R3 can be the same or different and R1, R2 and R3 are H or alkylcarbon chains from 1–20 carbons, either saturated or unsaturated, and having 0–10 heteroatoms (N, O, S).

In general, these dye classes excite approximately between about 470 and 530 nm and emit approximately between 600 and 780 nm (see Molecular Probes Handbook of Fluorescent Probes and Research Chemicals by Richard P. Haugland, 1992–1994, p. 156). A particularly preferred styryl dye is the trans-4-[4-(dibutylamino)styryl]-1-methylpyridinium iodide (Aldrich Chemical Co.) which has its maximum absorbance at 486 nm in dimethylformamide and its emission at 600 nm. One skilled in the art will recognize that the substituents off the aniline nitrogen and the pyridium nitrogen of these classes of dyes can vary and that preferred substituents are those with hydrophobic groups to maintain water insolubility.

In another application, an instrument system is built which has a source of maximum intensity at 420 nm and a detector as described in the above example. The dye system here can include the phthalocyanine acceptor; however, a different donor must be employed. A preferred donor for this application is a meso-tetra-2-aminophenylporphine (Porphyrin Products, Inc., Logan Utah) which has a maximum absorbance for excitation at 418 nm in dimethylsulfoxide and an emission around 655 nm. This porphyrin will excite the phthalocyanine derivative in latex particles and the dye system will emit at 680 nm.

In a particularly preferred application, an instrument system is built to perform immunoassays in neat blood or serum or in various biological specimens. The excitation source is a light emitting diode (LED) or laser diode which has a maximum intensity around 650 nm to avoid absorption of the light by the blood or serum sample. The detector has good quantum efficiency at 700 to 800 nm so a preferred acceptor dye is a naphthalocyanine derivative which has an emission at approximately 780 nm, an emission wavelength which is generally not in common with blood or serum samples or biological specimens. A donor dye for the naphthalocyanine acceptor should absorb at around 650 nm to coincide with the source and emit between approximately 660 nm and 760 nm. Preferred classes of dyes for this donor application are the carbocyanine dyes and the ethenyl-substituted dipyrrometheneboron difluoro dyes, as described in U.S. Pat. Nos. 5,187,288, 5,248,782 and 5,274,113.

In yet another particularly preferred application, an instrument system is built to perform immunoassays in neat blood, plasma or serum or in various biological specimens. The excitation source is an LED or a laser diode which has its maximum intensity around 670 nm to avoid absorption of the light by the blood, plasma or serum sample. The detector has good quantum efficiency at 700 to 800 nm so preferred acceptor dyes are silicon [(diphthalocyanine) dinaphthalocyanine] ligands or a naphthalocyanine derivative which have an emissions at approximately 760 nm and 780 nm, respectively, emission wavelengths which are generally not in common with blood or serum samples or biological specimens. A donor dye for the preferred acceptors should absorb at around 670 nm to coincide with the source and emit between approximately 660 nm and 760 nm. Preferred donor dyes are silicon phthalocyanine with axial ligands.

In yet another particularly preferred application, for immunoassays in neat blood or serum, the excitation source is around 790 nm and the emission wavelength is around 900 nm. A preferred dye for a single dye system is a silicon 1,6-octaethoxynaphthalocyanine bis (dimethylhexylvinylsilyloxide) which is excited at 790 nm and emits at about 900 nm.

Preferred dyes for use as donor dyes for naphthalocyanines and naphthalocyanine derivatives are, carbocyanines and ethenyl-substituted dipyrrometheneboron difluoro dyes, as described in U.S. Pat. Nos. 5,187,288, 5,248,782 and 5,274,113 which have excitation wavelengths up to 790 nm and emission wavelengths between about 670 nm and 800 nm.

Preferred carbocyanine dyes, which generally excite between 500 and 750 nm (see Molecular Probes Handbook) are of the general formula:

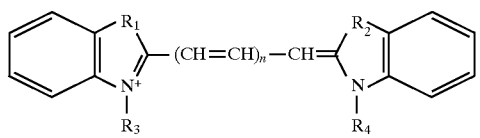

wherein n is 1 or 2; or 3; wherein R1 and R2 are S, N, or O; and wherein R3 and R4 are H or alkylcarbon chains of from 1–20 carbons, either saturated or unsaturated and having 0–10 heteroatoms (N, O, S).

Also preferred carbocyanine dyes are also of the general formula:

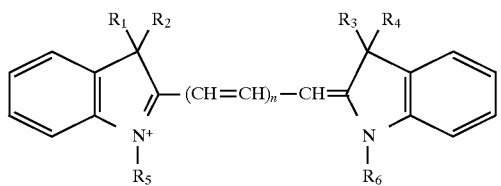

wherein n is 1 or 2; or 3; wherein R1–R6 are H or alkylcarbon chains of from 1–20 carbons, either saturated or unsaturated and having 0–10 heteroatoms (N, O, S).

Figure 4:
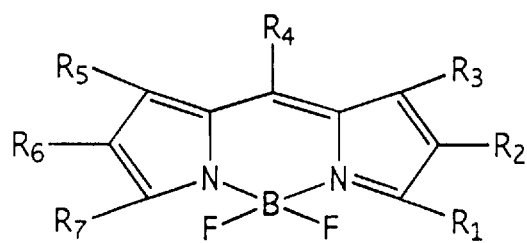
FIG. 4 depicts the general structure of ethenyl-substituted dipyrrometheneboron difluoro dyes.

Preferred donor dyes are also the ethenyl-substituted dipyrrometheneboron difluoro dyes, which generally excite above 500 nm (see Molecular Probes Handbook) and are of the general formula as depicted in FIG. 4, wherein R1–R7 include substituents as described in U.S. Pat. Nos. 5,187, 288, 5,248,782 and 5,274,113.

Particularly preferred donor dyes are 1,1'-didexyl-3,3,3', 3'-tetramethylindocarbocyanine iodide, 1,1'-diethyl-3,3,3'3'-tetramethylindodicarbocyanine iodide and (E,E)-3,5-bis-(4-phenyl-1,3-butadienyl)-4,4-difluoro-4-bora-3a, 4a-diazo-5-indacene (from Molecular Probes Inc., Eugene, Oreg.) which have absorption maximums of 642 nm, and 645 nm and 650 nm and emission maximums of 674 nm and 665 nm, and 670 nm, respectively, in dimethylformamide. Particles incorporated with these particularly preferred dyes and a naphthalocyanine derivative will excite with a 650 nm source and emit at approximately between 780 nm and 870 nm. One skilled in the art will recognize that the excitation and emission spectra for any particular dye has a Gaussian form and therefore the excitation source does not need to correspond exactly to the excitation maximum of the donor dye in order to obtain an intense fluorescent signal. Likewise, the donor emission does not have to coincide with the highest absorption of the acceptor dye in order to achieve efficient energy transfer. One skilled in the art will also recognize that the substituents at and on the 1 and 3 positions of the carbocyanines and the substituents at the R1and R7 positions of the dipyrrometheneboron difluoro dyes, and the conjugation between the ring structures can vary and these variations are also useful in tuning fluorescence spectra of the particles.

Also preferred emission wavelengths of fluorescent particles range from about 800 nm to 1000 nm. This near infra-red region is important because the scattering component of the light decreases substantially, thus lowering the background of the fluorescent measurement. In addition, biological samples do not absorb or fluoresce substantially in the 800 nm–1000 nm range. Particulate materials in the samples, for example, lipoproteins in serum, particles in ground water, cellular debris in biological samples and the like, can increase the background signal because of scattered light and the measurement of the scattered light is minimized in the 800–1000 nm range.

Figure 5:
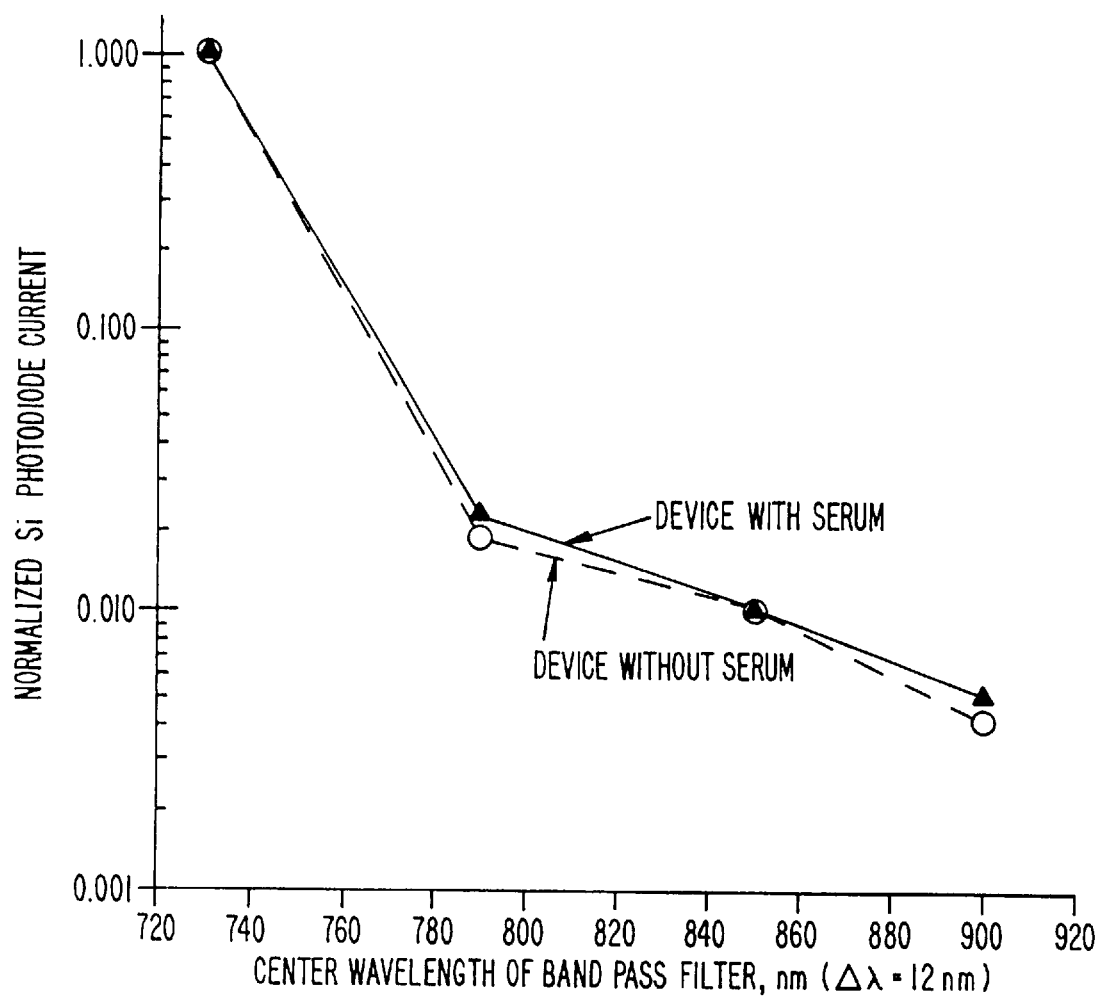
FIG. 5 depicts the attenuation of the background signal as a function of increasing wavelength. The data was measured using a device as described in Applicant's allowed Ser. No. 07/887,526 filed May 21, 1992 entitled "Diagnostic Devices and Apparatus for the Controlled Movements of Reagents Without Membranes," which is hereby fully incorporated herein.
Figure 6:
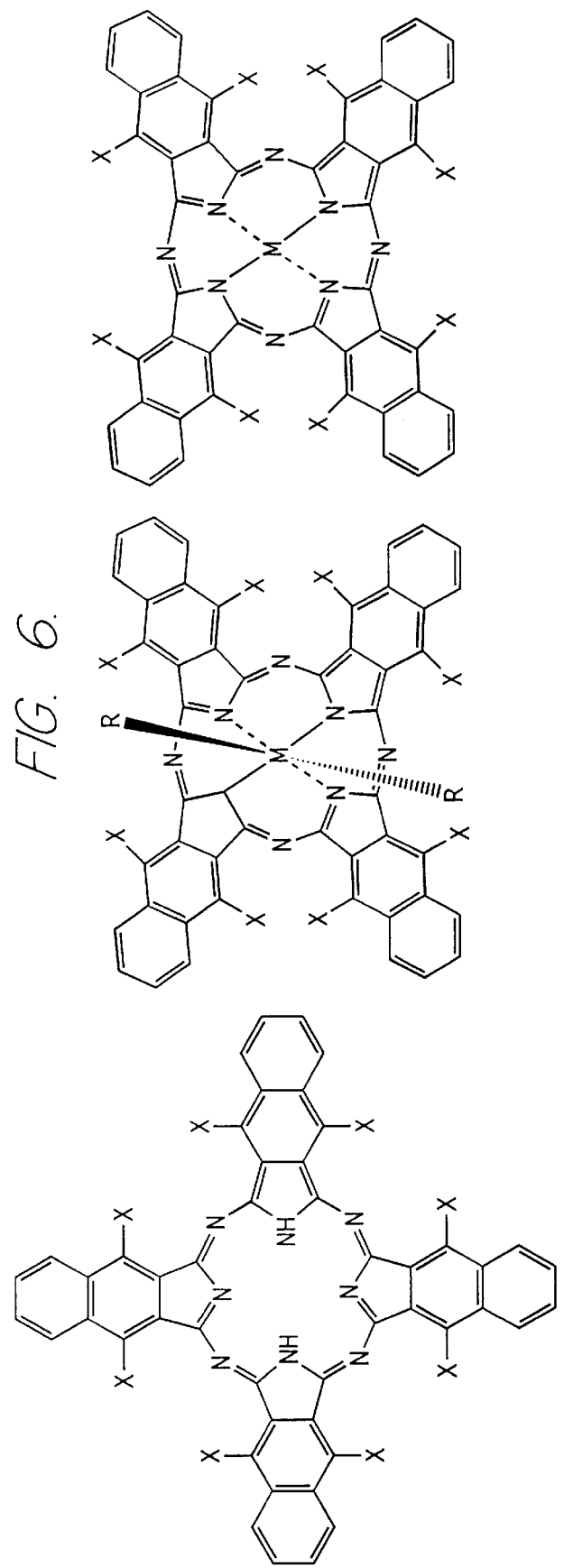
FIG. 6 depicts naphthalocyanine derivatives which emit in the near infrared.

FIG. 5 illustrates the attenuation of the background signal as the wavelength of the measured light increases from 730 nm to 900 nm in an immunoassay device, as described in allowed application Ser. No. 07/887,526 (which is herein incorporated by reference), containing either neat human serum or no serum. This figure shows that the background signal decreases by a factor of 5 when measuring at 900 nm as compared to 790 nm when the illumination source is a 1 milliwatt ("mW") 670 nm laser diode. In addition, excitation of neat serum at 670 nm does not result in a significant measurable fluorescence between 730 nm and 900 nm. Thus, for example, the signal to background ratio of the measurement of fluorescence of a dye which emits at around 900 nm as compared to a dye emitting at around 790 nm would be improved by a factor of 5. The signal to background ratio improves by a factor of about 30 when measuring emission at 780 nm as compared to 730 nm (see FIG. 5). Preferred dyes, for example as described in J. Chem. Soc. Perkin Trans. 1, (1988), 2453–2458, which emit above 780 nm include derivatives of the naphthalocyanine and anthranylocyanine classes (FIG. 1) and the naphthalocyanine class is characterized by the general formulae, as depicted in FIG. 6, where M is a metal such as Si, Ge, Al, Sn and Ti and the like, and where R is an axial ligand, alkyl or aryl with or without a silicon (preferred axial moieties are synthesized from alkyl or aryl silyl chlorides), and where X is an electron donating group or groups which can be the same or different, including, such as amino, hydroxyl, alkoxy, aryloxy, phenyl, alkyl and the like. The electron donating character of the X group or groups red-shifts the emission wavelength as compared to the general naphthalocyanine compounds (FIG. 1).

For example, the compounds described in examples 26, 27 and 28 are illustrative of dyes which have emission wavelengths around 850 nm. These preferred dyes would yield an improved signal to background ratio as compared to dyes emitting at 780 nm (See FIG. 5). Electron withdrawing groups can also be utilized for the X groups, such as halogen, nitro, cyano, sulfate, carboxyl and carboxyalkyl and the like, which will blue shift the excitation or emission wavelengths. Preferred donor dyes for this class of near infra-red emitting dyes are those which have emission wavelengths which correlate to the absorbance characteristics of the acceptor dye. Preferred dyes for this application are the ethenyl-substituted dipyrromethyleneboron difluoride dyes, as described in U.S. Pat. Nos. 5,187,288, 5,248,782 and 5,274,113.

Preferred molar ratios of donor to acceptor dyes in the latex particles generally range from about 20:1 to about 1:20 and particularly from about 1:1 to 6:1. The desired fluorescence intensity should be obtained through experimentation using the principles taught herein, and by incorporating various ratios of donor to acceptor dyes into the particles at various dye concentrations and measuring the fluorescence emission of the particles.

Figure 7:
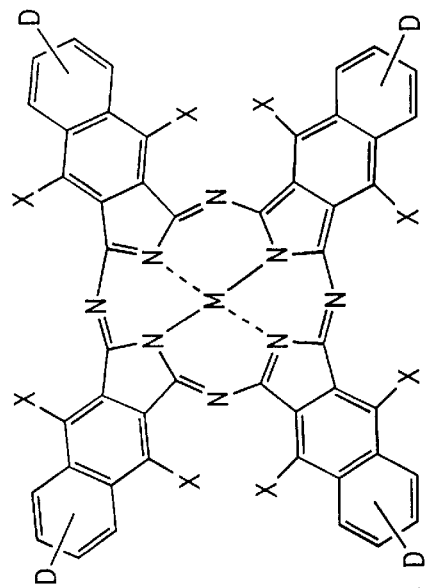
FIG. 7 depicts general structures of fluorescent energy transfer naphthalocyanine compounds.
Figure 7:
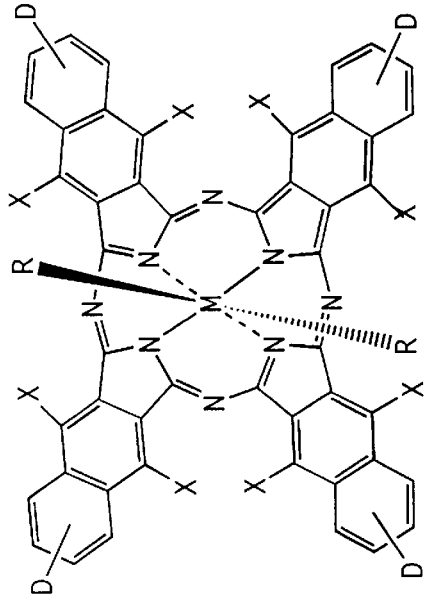
Figure 7:
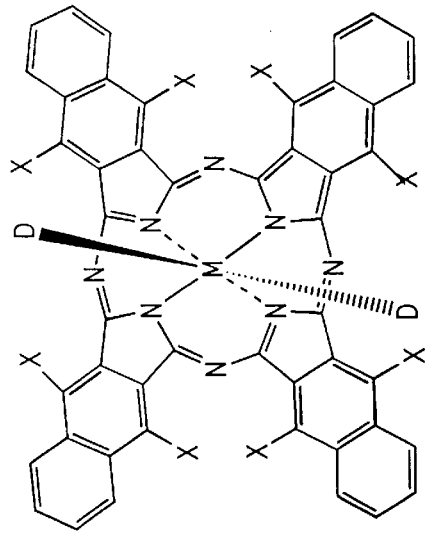

The geometrical orientation of the dipoles of the donor and acceptor dyes will affect the efficiency of energy transfer between them. The donor and acceptor dyes can be synthesized to form a compound of optimal dipole geometry, which, in solution, exhibits efficient fluorescence energy transfer ("FET"). The optimized FET compound then may be incorporated into particles. Phthalocyanine derivatives can be utilized for this application for the acceptor moiety, where the phthalocyanine derivative can be substituted with electron donating or withdrawing groups (as described above) to accommodate the desired excitation and emission wavelength. For example, preferred naphthalocyanine compounds for this application are those as depicted in FIG. 7, where X is hydrogen or electron donating groups, such as amino, hydroxyl, alkoxy, aryloxy, phenyl, alkyl and the like and D is the donor dye covalently attached to the naphthalocyanine derivative at a distance which allows for energy transfer between the donor and acceptor.

By applying the teachings of this invention, all phthalocyanine of hybrid phthalocyanine derivatives can function as donor or acceptor molecules. For example, a silicon ortho octaethoxy(phthalocyanine) derivative will emit at approximately 750 nm to 780 nm, similar to a silicon naphthalocyanine derivative. Generally, the distances between donor and acceptor are about 5 angstroms to 60 angstroms, and preferably from 5 angstroms to 15 angstroms. In addition, each naphthalocyanine derivative can have 1–4 donor dyes attached, depending on the required application of the FET compound. Suitable donor dyes are those which emit in the absorbance range of the acceptor dye. Example 29 describes the synthesis of a fluorescein-silicon phthalocyanine FET compound. Table 1, item 56, shows the fluorescence characteristics of this compound in latex particles. One skilled in the art will appreciate that with the inventive teachings described herein, many FET compounds may be synthesized for many particular applications requiring specific excitation and emission wavelengths.

Another approach to developing particles which exhibit desired and predictable fluorescence properties in the high visible to near infrared spectrum is to synthesize unsymmetrical or hybrid phthalocyanines, naphthalocyanines or anthranylocyanines and their derivatives. As used herein, the term "hybrid phthalocyanine derivatives" refers to all classes of hybrid phthalocyanines, naphthalocyanines and anthranylocyanines and their derivatives, with or without metal and axial ligands, including tetraazaporphines and their derivatives. The novel hybrid molecules described herein appear to exhibit intramolecular energy transfer. The hybrid phthalocyanine derivatives can be synthesized from diiminoisoindoline or derivatives of diiminoisoindolines and incorporate a metal, for example, silicon, and elaboration with axial ligands or they can be synthesized from dicarbonitrile derivatives of benzene, naphthalene or anthracene compounds, respectively, for subsequent inclusion of various metals and elaboration with axial ligands. Hybrid molecules comprised of derivatives of tetraazaporphines, as described in Inorg. Chem. (1994), 33, 1735–1740, are also within the scope of the hybrid phthalocyanine derivatives of the instant invention. A synthetic strategy for hybrid phthalocyanine derivatives with 2 different subunits is described, for example, in J. Am. Chem. Soc. (1990), 112, 9640–9641, Inorg. Chem. (1994), 33, 1735–1740, Chem. Letters, (1992), 763–766, Chem. Letters, (1992), 1567–1570 and Chem. Letters, (1992), 2031–2034. These references describe the synthesis of hybrid molecules with zinc metal or without metal and without axial ligands. The character of the diiminoisoindoline and its derivatives will dictate the excitation and emission characteristics of the molecule. Moreover, incorporation of dyes with axial ligands, as taught herein, will result in particles which exhibit minimum quenching and maximum fluorescence intensity.

Axial ligands are also beneficial on water soluble compounds because the axial ligands will minimize interaction of the hybrid molecule with, for example, proteins, antibodies and nucleic acids, which may or may not be covalently coupled to the hybrid molecule. The axial ligand may itself, impart water solubility to the hybrid phthalocyanine derivative.

Examples of water soluble phthalocyanine derivatives are disclosed in Examples 92, 95–98, 108, 110, 114–124, and 126–128.

Novel hybrid phthalocyanine derivatives are described herein, which contain 3 or 4 different subunits, and allow for larger Stokes shifts. In these derivatives, excitation occurs with the subunit which has the highest energy or the lowest wavelength absorption and the emission occurs in the lowest energy subunit.

The desired excitation and emission wavelengths of the hybrid phthalocyanine derivative will determine the types of diiminoisoindoline derivative and dicarbonitrile derivative precursors which are used in the synthesis of the hybrid phthalocyanines. The desired excitation and emission wavelengths are generally dictated by the sample, the type of fluorescent measurement and the instrument. Various combinations of diiminoisoindoline derivative and dicarbonitrile derivative precursors also may be combined to form a hybrid phthalocyanine derivative which may have a red shifted or blue shifted excitation and/or emission wavelength pattern.

In general, electron donating substituents on the diiminoisoindoline or dicarbonitrile precursors, particularly situated at the ortho positions (that is, ortho to the tetraazaporphine structure as indicated in FIG. 6 for the X substituents) of the phthalocyanine structure, such as amino, hydroxyl, alkoxy, aryloxy, phenyl, alkyl and the like, will red shift the excitation and/or emission wavelengths. Conversely, electron withdrawing substituents, also particularly at the ortho positions, such as halogen, nitro, cyano, sulfate, carboxyl and carboxyalkyl and the like, will blue shift the excitation or emission wavelengths. In addition, positions on the subunits other than the ortho positions can affect the excitation and emission characteristics of the hybrid phthalocyanine derivative. The choice of either diiminoisoindoline or dicarbonitrile precursors for the synthesis of the hybrid phthalocyanine derivatives is related to the desired presence or absence of metal and the type of metal in the hybrid molecule. For example, when using the diiminoisoindoline precursors in the synthesis, a silicon metal can be incorporated during the tetramerization reaction to form the phthalocyanine derivative structure. The silicon can be further modified to a silicon dihydroxy phthalocyanine derivative molecule so that axial ligands can be elaborated with, for example, various silyl chloride reagents. The importance of axial ligands in reducing quenching and maximizing fluorescence intensity is evident for both phthalocyanine/ naphthalocyanine molecules and the hybrid phthalocyanine derivatives (see example 65).

The axial ligands are also useful for further elaboration of the molecules, for example, for attaching another fluorescent molecule, for attaching to a ligand, protein, polypeptide or nucleic acid or for changing the charge of the molecule using sulfate, carboxylic acid or amino substituents which can affect solubility of the molecule. In the case of using axial ligands to attach the water soluble dye to ligands, proteins, polypeptides or nucleic acids, a mono- or bis- substituted metal can be utilized. The mono-substituted metal in the dye, however, yields only one axial ligand onto which the chemistry of attachment is made. The other face of the dye, after attachment to a ligand, protein, polypeptide or nucleic acid, which has no axial ligand, may interact with neighboring molecules (proteins, polypeptides, nucleic acids and the like) and result in quenching of fluorescence. The bis-substituted dye can minimize potential interactions between neighboring molecules when one axial ligand is used for attachment and the other is unattached. In this case, the unattached axial ligand can be synthesized such that the terminal atom of the unattached axial ligand imparts water solubility to the molecule, for example, a sulfate, carboxyl, or an amino derivative, such that interactions between neighboring molecules is minimized. In the case of utilizing water soluble hybrid phthalocyanine derivatives, for example, for competitive immunoassays, the ligand analogue of the target ligand which is being measured, can be attached to the dye through the axial ligand(s). The axial ligands of the water soluble phthalocyanine and hybrid phthalocyanine derivatives can also contain functional groups, for example, amines, carboxylic acids and esters, alkyl halides, thiols, thio ester and the like for attachment of ligands, proteins, polypeptides and nucleic acids. The axial ligands can also impart water solubility on the phthalocyanine and hybrid phthalocyanine derivatives when the axial ligand is comprised of poly(ethylene oxide). The carboxylic acid ester or the thioester groups on the axial ligands can be hydrolyzed in dilute base to the carboxylic acid and thiol groups, respectively. The chemical reactions to attach the axial ligands to ligands and ligand analogues, proteins, polypeptides and nucleic acids should be compatible with the functional groups of the compounds or macromolecules. For example, an amine on the axial ligand of the dye can be reacted with a compound or macromolecule containing a carboxylic acid or an alkyl halide, an alkyl halide on the axial ligand of the dye can be reacted with an amine or a thiol on the compound or macromolecule, a thiol on the axial ligand of the dye can be reacted with an alkyl halide or a maleimide group on the compound or macromolecule. Thus, compounds, such as ligands, ligand analogues and macromolecules, such as nucleic acids, polypeptides and antibodies can be reacted specifically to the dye by reaction with functional groups on the dye.

In general, phthalocyanine and hybrid phthalocyanine derivatives can be made water soluble by sulfonating the compounds using, for example, sulfuric acid or chlorosulfonic acid (see Gilbert, "Sulfonation and Related Reactions", Interscience, New York, 1965; Cerfontain, "Mechanistic Aspects in Aromatic Sulfonation and Desulfonation", Interscience, New York, 1968, *Int. J. Sulfur Chem.* C6, 123–136 (1971)). The sulfonation of the aromatic ring structure of the dye molecules can occur at various carbons of the ring. Added water solubility of the dye molecules can be achieved using axial ligands comprised of poly (ethylene oxide).

When using the dicarbonitrile precursors, the phthalocyanine derivative is synthesized without metal, but various metals can subsequently be included, for example, Ge, Al, Sn, Ti and the like. These metals can also be elaborated with axial ligand(s), depending on the valence of the metal.

The fluorescence quenching character of the hybrid phthalocyanine derivatives in particles are particularly preferred over the phthalocyanine derivatives. Example 66 is a typical example of comparison of the quenching characteristics in latex particles of silicon 2,3-naphthalocyanine-bis (dimethylhexylvinylsilyloxide) and silicon-[di(1,6-diphenylnaphthalocyanine)]-diphthalocyanine-bis-(dimethylhexylvinylsilyloxide). The hybrid phthalocyanine derivative has essentially no quenching as compared to up to 50% quenching of the naphthalocyanine derivative for the various dye loading concentrations listed in the table. The fluorescence intensity of latex containing the hybrid phthalocyanine derivative are much greater than the phthalocyanine derivative. This illustrates the special properties of the hybrid phthalocyanine derivatives.

The hybrid phthalocyanine derivatives are also very good acceptors when using phthalocyanine derivatives as donors. This is shown in table 6 of example 67. When the phthalocyanine derivative is the donor and the hybrid phthalocyanine derivative is the acceptor (dye system 3), the fluorescence intensity of the particles is about 145% higher than when the same phthalocyanine derivative is the donor and a naphthalocyanine derivative is the acceptor (dye system 2). These results show the special properties of the hybrid phthalocyanine derivative in particles exhibiting fluorescence energy transfer.

The hybrid phthalocyanine derivative also acts as an intermediate donor compound. Table 6 of Example 67 shows that the fluorescence intensity of a naphthalocyanine acceptor in a particle prepared in 70% tetrahydrofuran (dye system 4) is increased about 65% when a phthalocyanine donor excites a hybrid phthalocyanine compound as compared to the phthalocyanine donor directly exciting the naphthalocyanine acceptor (dye system 2). These results further illustrate the special properties of the hybrid phthalocyanine derivatives in latex particles exhibiting fluorescence energy transfer.

The results of Table 6 of Example 67 also show the ability of phthalocyanine derivatives with axial ligands to exhibit singlet-singlet energy transfer to other phthalocyanine or hybrid phthalocyanine derivatives with axial ligands. That is, it is apparent from Example 65 and Table 4, that axial ligands reduce the quenching of the dyes and enhance the fluorescence of the particles. Other experiments (see Example 15, Tables 1 and 2) also support this observation. Thus, axial ligands minimize quenching by preventing the close contact of the ring structures. One would then expect that phthalocyanine or hybrid phthalocyanine derivatives with axial ligands would not be spaced sufficiently close to function efficiently as energy transfer donor and acceptor pairs because the molecules are spaced apart by the axial ligands. However, nearly 100% efficiency of energy transfer and high fluorescence intensities are observed in particles when phthalocyanine or hybrid phthalocyanine derivatives with axial ligands are donors and phthalocyanine or hybrid phthalocyanine derivatives are acceptors.

The tetramerization reactions of the diiminoisoindoline or dicarbonitrile precursors to form the hybrid phthalocyanine derivatives can be directed so that opposing subunits can be the same. This is accomplished, for example, with the use of bulky substituents on the precursors so that in the tetramerization reaction, like subunits with bulky substituents cannot be adjacent because of steric considerations. Bulky phenyl substituents have been used on dicarbonitrile precursors to direct the precursors tetramerization to be opposing subunits as described in Inorg. Chem. (1994), 33, 1735–1740, Chemistry Letters (1992), 2031–2034 and Chemistry Letters (1992), 1567–1570.

Preferred hybrid phthalocyanine derivatives have similar opposing subunits so that two different subunits comprise the structure. Particularly preferred hybrid phthalocyanine derivatives have similar opposing subunits on one axis and different opposing subunits on the other axis. The nature of the particularly preferred molecules is that red or blue shifted excitation or emission wavelengths and a longer Stokes shift can result because of the selection of the precursor molecules for the tetramerization reaction. For particularly preferred hybrid phthalocyanine derivatives, for example, the "donor" diphenyldiiminoisoindoline or the diiminoisoindoline precursors would contribute to 650 nm absorbance of the hybrid molecule, and thereby to the excitation of the hybrid molecule. The diphenyl phenyldiiminoisoindoline or the phenyldiiminoisoindoline precursors would act as an "electron transfer subunit" to the "acceptor subunit", which would be a dialkoxy or aryloxy phenyldiiminoisoindoline precursors, so that emission is dictated at the lowest energy by the acceptor subunit at about 850 nm. The nature of the "electron transfer subunit" is important because it is not desirable for this subunit to emit because then the desired emission of the acceptor subunit will not take place. Thus, the highest occupied molecular orbital (HOMO) and lowest unoccupied molecular orbital (LUMO) character of the electron transfer subunit should be designed with reference to the donor and acceptor subunit molecules. The relationship of the energies of the HOMO and LUMO as they relate to excitation and emission are taught by Pariser et al., J. Chem. Phys. (1953), 21, 767–776, by Pople, Trans. Faraday Soc. (1953), 49, 1375–1385, by McHugh et al., Theoret. Chim. Acta (Berlin) (1972), 24, 346–370 and by Kobayashi et al, Inorg. Chem. (1994), 33, 1735–1740, Chemistry Letters (1992), 2031–2041, Konami et al., Molecular Physics (1993), 80, 153–160.

Another application requires the hybrid molecule to have two excitation wavelengths, one at approximately 650 nm and another at about 680 nm with emission for both excitations at about 760 nm. Thus, the precursors responsible for the excitation could be a diiminoisoindoline for the 650 nm and a tetrafluorodiiminoisoindoline for the 680 nm excitations. The emitting subunit, which can also be used to direct the tetramerization reaction so that the emitting subunits are opposed in the molecule, can be a diphenyl phenyldiiminoisoindoline. The excitation and emission wavelengths of the resulting hybrid phthalocyanine derivative are thus generally representative of the individual diiminoisoindoline precursors.

Yet another application requires excitation at about 650 nm and emission at about 750 nm. The precursors responsible for excitation and emission could be diiminoisoindoline and diphenyl phenyldiiminoisoindoline, respectively. The latter precursor also acts to direct the emitting subunits to be opposed.

In another application, a large extinction coefficient at the excitation wavelength is desired for excitation at about 650 nm. The emission wavelength should be at about 850 nm. The precursors responsible for excitation could be a diphenyldiiminoisoindoline, which would direct these subunits to be opposed and thereby two subunits would contribute to provide the desired extinction coefficient. A phenyldiiminoisoindoline derivative precursor could act as an electron transfer subunit and an alkoxyphenyldiiminoisoindoline precursor could be the acceptor with a characteristic emission at about 850 nm.

In another application, two emission wavelengths are desired from a compound which is excited at a single wavelength. The desired excitation is around 650 nm and the emission should be around 760 nm and 810 nm. The precursor responsible for excitation could be a tetrafluorodiiminoisoindoline or a tetrafluorobenzene-1,2-dicarbonitrile. The precursor responsible for emission could be a dibutoxy-phenyldiiminoisoindoline or a 3,4-dibutoxynaphthalene-1,2-dicarbonitrile, respectively.

Incorporation of Dyes into Particles

The resulting compounds are then incorporated into particles to yield particles which exhibit excitation wavelengths above about 600 nm and emission wavelengths above about 650 nm. One skilled in the art will also appreciate that water soluble hybrid phthalocyanine derivatives are valuable for coupling to proteins, polypeptides, nucleosides, nucleic acids and the like, for detecting their presence in biological fluids or for performing DNA probe or immunoassays.

Preferred particle sizes range from about 0.1 nm to 5000 nm and preferably from about 1 nm to 1000 nm. The choice of particle size should be related to the specific function for the label. The particle size may vary for a particular application. For example, in an immunoassay, if the label requires a more intense fluorescence for measuring very low concentrations of analytes, then one would employ larger particles because larger particles can incorporate more dye molecules. The small particle sizes (0.1–1 nm) may be employed in fluorescence polarization assays, as described for example, in U.S. Pat. Nos. 4,420,568, 4,476229 and 4,510,251, in in vitro visualization of cellular components or in in vivo imaging techniques.

The resulting fluorescent dye particles which exhibit the appropriate excitation and emission characteristics are further adsorbed or chemically reacted with various nucleic acids, nucleotides, proteins or peptides and the like which are required for a specific purpose. The adsorption of macromolecules to particles, particularly latex particles is well known to those skilled in the art and generally involves adsorption of the macromolecule at a temperature between 5° C. and 50° C. and at a pH which is below the pI of the molecule.

Use of Incorporated Dye Particles in Assays

Fluorescent particles exhibiting fluorescence energy transfer can be adsorbed with either antibodies for use in non-competitive immunoassays or ligand analogues for use in competitive immunoassays in reaction mixtures of the assays. In the case of non-competitive assays, the reaction mixture would include at least one target ligand and at least one class of fluorescent particles having bound thereto at least one receptor specific for target ligand, forming an antibody (fluorescent) conjugate. In the case of competitive assays, the reaction mixture will include at least one target ligand, at least one receptor specific to the target ligand, and at least one class of fluorescent particles, having bound thereto at least one ligand analogue, forming a ligand analogue (fluorescent) conjugate. The antibody conjugates bound to target ligands in the non-competitive reaction mixture and the ligand analogue conjugates not bound by receptors specific to the target ligands in the competitive reaction mixture can be bound to a solid phase consisting of receptors specific to another epitope of the target ligand of the target ligand-antibody conjugate complexes and of receptors specific to ligand analogues of the ligand analogue conjugates, respectively. The fluorescent conjugates unbound by the solid phase are removed and the fluorescence of the bound conjugates is measured. The measured fluorescence is related to the target ligand concentration. The various reagents described above can also be attached covalently to the latex particles. For example, antibodies or ligand analogues can be attached through amine or carboxylic acids to carboxylic acids or amines on the surface of the particles, respectively, to form stable amide linkages.

In the case of quantifying nucleic acids in samples, the novel compounds described in the instant invention are useful because of their brightness and because of the near infrared emission characteristics. In general, in designing an assay for a nucleic acid, one selects a probe molecule which is complementary to the nucleic acid to be quantified. The probe molecule is then labeled, generally covalently, with a signal generator. The signal generator can be a water soluble phthalocyanine derivative or hybrid phthalocyanine derivative or a particle with the appropriate dye system, which may exhibit fluorescence energy transfer or hybrid phthalocyanine derivatives or combinations of these compounds. The labeled probe molecule is then introduced into a biological sample suspected of containing the target nucleic acid, and the labeled probe sequence assembles with the target nucleic acid. The labeled probe/target nucleic acid can then be immobilized onto a surface which has immobilized another nucleic acid which is also complementary to the target nucleic acid. Conversely, the biological sample can be introduced to a surface which has immobilized a complementary nucleic acid for immobilization of the target nucleic acid. The labeled probe can then be introduced to the system for binding to the immobilized target molecule. The excess labeled probe is then washed away and the resultant fluorescent intensity is correlated with fluorescence intensity from a standard curve to arrive at a concentration of the nucleic acid in the sample.

Use of Water Soluble Hybrid Phthalocyanine Derivatives in Assays

Water soluble hybrid phthalocyanine derivatives can be attached to antibodies for use in non-competitive immunoassays or ligand analogues for use in competitive immunoassays in reaction mixtures of the assays. In the case of non-competitive assays, the reaction mixture would include at least one target ligand and at least one water soluble hybrid phthalocyanine derivative having attached thereto at least one receptor specific for target ligand, forming an antibody (fluorescent) conjugate. In the case of competitive assays, the reaction mixture will include at least one target ligand, at least one receptor specific to the target ligand, and at least one water soluble hybrid phthalocyanine derivative having attached thereto at least one ligand analogue, forming a ligand analogue (fluorescent) conjugate. In addition, in certain embodiments, the antibody conjugates and ligand analogue conjugates can be utilized as non-fluorescent labels. The non-fluorescent labels would be used in applications where only a color response, measured by reflectance in an assay device, is necessary.

The fluorescent conjugates of water soluble hybrid phthalocyanine derivatives, which are smaller in molecular weight than the fluorescent particles described herein, will diffuse faster in solution and result in binding reactions which have faster kinetics. Fast kinetics of the binding reactions in assays are preferred because the assays will reach equilibrium binding in a shorter time, and in turn, assay results can be obtained in a shorter time. The antibody conjugates bound to target ligands in the non-competitive reaction mixture and the ligand analogue conjugates not bound by receptors specific to the target ligands in the competitive reaction mixture can be bound to a solid phase consisting of receptors specific to another epitope of the target ligand of the target ligand-antibody conjugate complexes and of receptors specific to ligand analogues of the ligand analogue conjugates, respectively. The fluorescent conjugates unbound by the solid phase are removed and the fluorescence (or color) of the bound conjugates is measured. The measured fluorescence (or color) is related to the target ligand concentration.

In the case of quantifying nucleic acids in samples, the novel compounds described in the instant invention are useful because of their brightness and because of the near infrared emission characteristics. In general, in designing an assay for a nucleic acid, one selects a probe molecule which is complementary to the nucleic acid to be quantified. The probe molecule is then labeled, generally covalently, with a signal generator. The signal generator can be a water soluble phthalocyanine derivative or hybrid phthalocyanine derivative. The labeled probe molecule is then introduced into a biological sample suspected of containing the target nucleic acid, and the labeled probe sequence assembles with the target nucleic acid. The labeled probe/target nucleic acid can then be immobilized onto a surface which has immobilized another nucleic acid which is also complementary to the target nucleic acid. Conversely, the biological sample can be introduced to a surface which has immobilized a complementary nucleic acid for immobilization of the target nucleic acid. The labeled probe can then be introduced to the system for binding to the immobilized target molecule. The excess labeled probe is then washed away and the resultant fluorescent intensity is correlated with fluorescence intensity from a standard curve to arrive at a concentration of the nucleic acid in the sample.

Those skilled in the art will recognize that many variations of immunoassays and nucleic acid assays can be performed and the inventive teachings in the instant invention for the use of novel dye systems can be used to develop novel adaptations to existing technologies.

Those skilled in the art will appreciate that the novel fluorescent particles and dyes described herein have many uses in immunoassays, fluorescence microscopy, in vivo imaging, in vitro cancer therapy, nucleic acid assays, cell sorters and the like.

Experimental Section

Fluorescence measurements referred to in the following Examples were performed on a Perkin-Elmer model LS 50B Luminescence Spectrometer for dyes emitting up to around 780 nm. In some instances, as indicated in Table 1 by describing the Intensity in terms of nanoamps (nA), dyes emitting above 800 nm were measured according to Example 18. The fluorescence intensities are not corrected. Absorbance measurements were performed on a Hewlett Packard 8452A Diode Array Spectrophotometer.

EXAMPLE 1

Synthesis of Silicon Phthalocyanine Dihydroxide SiPc(OH)$_2$

A suspension of silicon phthalocyanine dichloride (1.83 g, 3.0 mmol) in pyridine (50 ml) and water (50 ml) was refluxed with stirring on an oil bath at 120° C. for 18 hours. After cooling the dark blue solid product was filtered and the residue was washed with water (10 ml), acetone (5 ml) and then dried under vacuum to afford 1.71 g of the title compound.

EXAMPLE 2

Synthesis of Silicon Phthalocyanine bis (trihexylsilyloxide) (hereinafter sometimes referred to as PcSi trihexyl)

A suspension of silicon phthalocyanine dihydroxide (115 mg, 0.2 mmol) in anhydrous pyridine (11 ml) containing chlorotrihexylsilane (733 μL, 2.0 mmol) was refluxed on an oil bath at 130° C. for 5 hours. The resulting purple solution was allowed to cool and was evaporated. The resulting slurry was treated with ice-cold hexane (2 ml) and the dark blue solid product was filtered, washed with ice-cold hexane (2 ml) and was dried under vacuum to yield 249 mg of crude product. The crude product in chloroform was purified on an Alumina column (Activity 1) equilibrated in hexane and the product was eluted with hexane/toluene (2/1, v/v) as a bright blue band. The solvent containing the product was evaporated to yield 69 mg of the title compound with a melting point of (mp) 171° C. (literature mp is 175° C.).

EXAMPLE 3

Synthesis of Silicon Phthalocyanine bis[(10-carbomethoxydecyl) dimethylsilyloxide] (Hereinafter sometimes referred to as PcSi methyl ester)

To a suspension of silicon phthalocyanine dihydroxide (115 mg, 0.2 mmol) in anhydrous pyridine (11 ml) was added (10-carbomethoxydecyl)dimethylchlorosilane (586 mg, 2 mmol) and the mixture was refluxed with stirring on an oil bath at 130° C. for 5 hours. The dark blue solution was allowed to cool and the solvent was evaporated. The residue was purified on a Silica gel 60 Å column equilibrated in hexane and the product eluted slowly as a blue band with toluene. The toluene fraction containing product was evaporated, hexane (10 ml) was added to the residue and the blue product was filtered, washed with hexane and dried to afford 105 mg of the title compound.

EXAMPLE 4

Synthesis of Silicon Phthalocyanine bis (dimethylvinylsilyloxide) (Hereinafter sometimes referred to as PcSi vinyl)

To a suspension of silicon phthalocyanine dihydroxide (115 mg, 0.2 mmol) in anhydrous pyridine (11 ml) was added chlorodimethylvinylsilane (276 μL, 2.0 mmol) and the mixture was refluxed with stirring on an oil bath at 130° C. for 5 hours. The dark solution was allowed to cool and was evaporated. The residue was purified on a Silica gel 60 Å column equilibrated in hexane and the product was eluted with toluene as a blue band. The eluate containing product was evaporated, the residue treated with hexane and the dark blue solid product was filtered, washed with hexane and was dried under vacuum to afford 7.5 mg of the title compound.

EXAMPLE 5

Synthesis of Silicon Phthalocyanine bis[(3-cyanopropyl) dimethylsilyloxide] (Hereinafter sometimes referred to as PcSi cyano)

To a suspension of silicon phthalocyanine dihydroxide (115 mg, 0.2 mmol) in anhydrous pyridine (11 ml) was added chloro(3-cyanopropyl)-dimethylsilane (328 μL, 2.0 mmol) and the mixture was refluxed with stirring on an oil bath at 130° C. for 5 hours. The purple solution was allowed to cool and was evaporated. The residue was purified on a Silica gel 60 Å column equilibrated in hexane. The column was washed with toluene and the product was eluted with toluene/isopropyl alcohol (90/10, v/v) as a bright blue band. The eluate containing product was evaporated under vacuum to afford 101 mg of the title compound with a mp>260° C.

EXAMPLE 6

Synthesis of Silicon Phthalocyanine bis (dimethylpentafluoro-phenylsilyloxide) (Hereinafter sometimes referred to as PcSi pentafluoro)

To a suspension of silicon phthalocyanine dihydroxide (115 mg, 0.2 mmol) in anhydrous pyridine (11 ml) was added chlorodimethylpentafluorophenylsilane (376 μL, 2.0 mmol) and the mixture was refluxed with stirring on an oil bath at 130° C. for 5 hours. The dark green solution was allowed to cool and was evaporated. The residue was purified on a Silica gel 60 Å column equilibrated in hexane. The product was eluted with toluene as a dark blue band. The eluate containing the product was evaporated, the residue was treated with hexane (10 ml) and the dark blue solid product was filtered, washed with hexane and was dried under vacuum to afford 73 mg of the title compound.

EXAMPLE 7

Synthesis of Silicon 2,3-Naphthalocyanine Dihydroxide (Hereinafter sometimes referred to as NaPcSi hydroxide)

A suspension of silicon 2,3-naphthalocyanine dichloride (280 mg, 0.34 mmol) in pyridine (10 ml) and water (10 ml) was refluxed with stirring on an oil bath at 130° C. for 24 hours. After cooling to room temperature, the dark green solid product was filtered and, the residue was washed, successively, wit h water (5 ml) and acetone (2 ml). The product was dried under vacuum to affor d 217 mg of the title compound.

EXAMPLE 8

Synthes is of Silicon 23-Napohthalocyanine bis (dimethylvinylsilyloxide) (Hereinafter sometimes referred to as NaPcSi vinyl)

To a s uspension of silicon 2,3-naphthalocyanine dihydroxide (87 mg, 0.11 mmol) in anhydrous dimethylformamide (1 ml) was added chlorodimethylvinylsilane (0.042 ml, 0.3 mmol), followed by imidazole (14 mg, 0.2 mmol). The mixture was stirred under argon at room temperature for 24 hours. The solvent was evaporated and the residue was purified on a Silica gel 60 Å column which was equilibrated in hexane. The product was eluted with toluene as a green band. The toluene fraction containing the product was evaporated and the residue was treated with hexane. The dark green solid was filtered, washed with hexane and was dried under vacuum to afford 26 mg of the title compound.

EXAMPLE 9

Synthesis of Silicon 2,3-Naphthalocyanine bis (dimethylpentafluorophenylsilyloxide) (Hereinafter sometimes referred to as NaPcSi pentafluoro)

To a suspension of silicon 2,3-naphthalocyanine dihydroxide (87 mg, 0.11 mmol) in anhydrous pyridine (5 ml) was added chlorodimethylpentafluorophenylsilane (0.188 ml, 1 mmol). The mixture was refluxed with stirring on an oil bath at 130° C. for 5 hours. After cooling, the solvent was evaporated and the residue was purified on a Silica gel 60 Å column which was equilibrated in hexane. The product was eluted with toluene as a green band. The toluene fraction containing the product was evaporated and the residue was treated with hexane. The dark green solid was filtered, washed with hexane and was dried under vacuum to afford 23 mg of the title compound.

EXAMPLE 10

General Preferred Procedures for the Preparation of Dye-loaded Latex Particles of Varying Sizes The various dyes were loaded into latex particles of varying sizes according to the general procedures outlined below. The procedures described involve swelling latex particles with aqueous solutions of either tetrahydrofuran or dimethylformamide prior to addition of the dye solutions. Latex particle sizes used range from 67 nm to 783 nm and one skilled in the art recognizes that smaller and larger particles can be used. Tables 1 and 2 of Example 15 below show the aqueous organic solvent system and the optimum dye concentration which were used for the loading into particles for each dye pair or for hybrid phthalocyanine derivatives, respectively, of a selected number of dyes. One skilled in the art recognizes that many changes can be made to these procedures to prepare particles with different degrees of fluorescence intensities and quenching by loading higher or lower amounts of dye in the particles and also by changing the ratios of each dye pair to the other. One skilled in the art also recognizes that similar techniques are useful for incorporation of dyes into latex particles, for example, as described in U.S. Pat. Nos. 4,199,363 and 4,368,258.

Surfactant-free polystyrene sulfate latex particles in sizes ranging from 67 nm to 783 nm and carboxyl-modified latex ("CML") particles ranging from 200 nm to 400 nm particles were obtained through Interfacial Dynamics Corp. Inc., Portland Oreg.

Method 1 Utilizing Tetrahydrofuran a. 20% Tetrahydrofuran

Tetrahydrofuran (0.09 ml) was added, dropwise over a 5 minute period, to a stirring solution of 0.5 ml of 2.0% solids of latex particles at room temperature. The latex suspension was stirred at room temperature for an additional 30 minutes to swell the latex. The dye solution (0.01 ml), which consists of one or more dyes at an appropriate concentration in tetrahydrofuran, was added dropwise over 5 minutes to the stirred latex solution, to give the loading dye concentration (in a 0.6 ml volume) as indicated in Table 1. The latex-dye solution was stirred at room temperature for 30 minutes in the dark. The latex solution was then transferred to dialysis tubing (Spectra-por, 12–14,000 molecular weight cutoff, Spectrum, Houston, Tex.) and the dye-latex solutions were dialyzed against water for 12–15 hours at 4° C. The dye-latex solution was removed from dialysis and the % solids of the solution was calculated from the final volume after dialysis and the starting solids concentration.

b. 50% Tetrahydrofuran

Tetrahydrofuran (0.20 ml) was added, dropwise over a 5 minute period, to a stirring solution of 0.24 ml of 4.1% solids of latex particles at room temperature. The latex suspension was stirred at room temperature for an additional 30 minutes to swell the latex. The dye solution (0.06 ml), which consists of one or more dyes at an appropriate concentration in tetrahydrofuran, was added dropwise over 5 minutes to the stirred latex solution, to give the loading dye concentration (in a 0.5 ml volume) as indicated in Table 1. The latex-dye solution was stirred at room temperature for 30 minutes in the dark. The latex solution was then dialyzed and analyzed according to the procedures outlined in the 20% tetrahydrofuran method.

c. 70% Tetrahydrofuran

Tetrahydrofuran (0.29 ml) was added, dropwise over a 5 minute period, to a stirring solution of 0.15 ml of 6.7% solids of latex particles at room temperature. The latex suspension was stirred at room temperature for an additional 30 minutes to swell the latex. The dye solution (0.06 ml), which consists of one or more dyes at an appropriate concentration in tetrahydrofuran, was added dropwise over 5 minutes to the stirred latex solution, to give the loading dye concentration (in a 0.5 ml volume) as indicated in Table 1. The latex-dye solution was stirred at room temperature for 30 minutes in the dark. The latex solution was then dialyzed and analyzed according to the procedures outlined in the 20% tetrahydrofuran method.

Method 2 Utilizing Dimethylformamide a. 50% Dimethylformamide

Dimethylformamide (0.20 ml) was added, dropwise over a 5 minute period, to a stirring solution of 0.24 ml of 4.1% solids of latex particles at room temperature. The latex suspension was stirred at room temperature for an additional 30 minutes to swell the latex. The dye solution (0.06 ml), which consists of one or more dyes at an appropriate concentration in dimethylformamide, was added dropwise over 5 minutes to the stirred latex solution, to give the loading dye concentration (in a 0.5 ml volume) as indicated in Table 1. The latex-dye solution was stirred at room temperature for 30 minutes in the dark. The latex solution was then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the % solids of the solution was calculated from the final volume after dialysis and the starting solids concentration.

b. 70% Dimethylformamide

Dimethylformamide (0.29 ml) was added, dropwise over a 5 minute period, to a stirring solution of 0.15 ml of 6.7% solids of latex particles at room temperature. The latex suspension was stirred at room temperature for an additional 30 minutes to swell the latex. The dye solution (0.06 ml), which consists of one or more dyes at an appropriate concentration in dimethylformamide, was added dropwise over 5 minutes to the stirred latex solution, to give the loading dye concentration (in a 0.5 ml volume) as indicated in Table 1. The latex-dye solution was stirred at room temperature for 30 minutes in the dark. The latex solution was then dialyzed and analyzed according to the procedures outlined in the 50% dimethylformamide method.

EXAMPLE 11

Effect of Varying Dye Loading Concentration on Fluorescence Intensity and Optimization of Fluorescence Intensity Latex Particles The incorporation of dye into latex particles must be optimized in order to achieve the maximum fluorescence intensity and to minimize the degree of fluorescence quenching of the dye molecules. Fluorescence quenching can be significant because of the close proximity of the dye molecules in the particles. The PcSi vinyl was incorporated into 67 nm latex particles (polystyrene sulfate from Interfacial Dynamics Corp. (IDC), Inc., Portland, Oreg.) using method 1 (example 10) at various concentrations as indicated in the table below. The dye latex particles were diluted to 0.0019% solids in either water or tetrahydrofuran for each dye concentration. The solutions were excited at 350 nm and the emission at 680 nm was measured. The percent quenching in the particles is: (1-[fluorescence intensity in water divided by the intensity in the organic solvent])×100. The table below shows the fluorescence intensities as a function of dye loading concentrations and quenching for each condition.

| Loading Dye Concentration (mg/ml) | Intensity (680 nm) | Quenching (%) |
|---|---|---|
| 0.01 | 420 | 41 |
| 0.025 | 489 | 65 |
| 0.05 | 492 | 73 |
| 0.075 | 401 | 76 |
| 0.1 | 338 | 83 |
| 0.15 | 197 | 87 |
| 0.3 | 91 | 90 |
| 0.9 | 34 | 96 |

These results show that an optimum loading dye concentration gives the highest fluorescence intensities and the lowest quenching. In this case, a dye concentration of between 0.025 and 0.05 mg/ml in the loading solution gives the best intensity and the least quenching. Less dye than 0.025 mg/ml gives less intensity and less quenching because the spacing of the dyes begins to significantly increase and more dye than 0.05 mg/ml gives less intensity and more quenching because of the increased closeness of the dyes in the particles. This type of experiment illustrates the procedure for optimization of fluorescence intensity and for minimizing quenching.

EXAMPLE 12

Verification of Fluorescence Energy Transfer in Latex Particles

The latex particles which were incorporated with various dyes for energy transfer were diluted to 0.06% to 0.001% solids in water and either tetrahydrofuran or dimethylformamide and the solutions of equal solids concentrations were excited at wavelengths which corresponded to the approximate excitation maximum of the donor dye. The particles were diluted into organic solvents in order to liberate the dyes from the latex, and therefore, disrupt any energy transfer process between the dyes in the particles. The fluorescence of the solutions in water and organic solvent at the emission maximum of the acceptor dye or dyes were recorded and compared. Fluorescence energy transfer was defined as significant when the emission intensity of the acceptor was at least 5-fold higher in water than in the organic solvent.

EXAMPLE 13

Effect of Varying Donor Dye Concentration With Respect to Acceptor Dye Concentration in Latex Particles on the Fluorescence Intensity of the Particles Meso-tetra-2-dimethylaminophenyl porphyrin was made as follows. To a stirring solution of meso-tetra-2-aminophenyl porphyrin (100 mg, 0.15 mmol) and 37% aqueous formaldehyde (500 µL, 6.0 mmol) in tetrahydrofuran (2.5 ml was added sodium cyanoborohydride (114 mg, 1.8 mmol). The mixture was then treated with a glacial acetic acid (60 µL) over 10 minutes and stirred at room temperature for 3 hours. More glacial acetic acid (60 µL) was added and the mixture stirred a further 1 hour at room temperature. The mixture was evaporated and the residue was purified on a Silica gel 60 Å column which was equilibrated in toluene. The product was eluted with toluene/ 1% isopropanol as a dark brown band. The fraction containing the product was evaporated and the ink-blue solid residue dried under vacuum to afford 85 mg of the title compound.

Meso-tetra-2-dimethylaminophenyl porphyrin (Tdap synthesized from the meso-tetra-2-aminophenyl porphyrin which was obtained through Porphyrin Products, Inc. Logan, Utah) and PcSi vinyl (example 4) were incorporated into 67 nm latex particles (polystyrene sulfate latex from Interfacial Dynamics Inc., Portland, Oreg.) using the tetrahydrofuran method 1 of example 10. The molar ratio of the Tdap to the PcSi vinyl varied from 1/1 to 2/1 to 6/1 in the latex loading solutions while maintaining a constant mass (0.1 mg/ml) of PcSi vinyl in each solution. The dialyzed particles were diluted to 0.0019% solids in water and the fluorescence intensity at 680 nm of the PcSi vinyl was measured as a function of excitation wavelength between 350 nm and 470 nm. The excitation maximum of the Tdap is 430 nm and of the PcSi vinyl is 350 nm. The emission maximum of the Tdap is 650 nm. The table below shows the results.

| Tdap/PcSi vinyl | Excitation λ (nm) | Fluorescence Intensity at 680 nm |
|---|---|---|
| 1/1 | 350 | 490 |
| 1/1 | 430 | 83 |
| 1/1 | 450 | 38 |
| 1/1 | 470 | 11 |
| 2/1 | 350 | 580 |
| 2/1 | 430 | 830 |
| 2/1 | 450 | 460 |
| 2/1 | 470 | 220 |
| 6/1 | 350 | 600 |
| 6/1 | 430 | 1800 |
| 6/1 | 450 | 890 |
| 6/1 | 470 | 200 |

These results show that as the molar ratio of donor to acceptor in the latex particles increases from 1/1 to 6/1, the energy transfer, as measured by the fluorescence intensity of the acceptor dye, becomes significantly more efficient. There was no observable emission of the Tdap dye in the particles at the emission maximum of 650 nm suggesting that the energy transfer is very efficient. The data indicates that the fluorescence intensity of the latex particles, generated through an energy transfer pathway, is affected by the "light gathering" capability of the donor dye. Thus, optimization of the fluorescence intensity of the latex particles should involve changing the molar ratio of donor to acceptor.

EXAMPLE 14

Effect of Incorporation of Different Dyes on Quenching and Fluorescence Intensity of Latex Particles Five different silicon phthalocyanines, synthesized as described in examples 2–6, were incorporated into 67 nm surfactant-free, polystyrene latex particles (Interfacial Dynamics Corp. Inc. Portland, Oreg.) in sets of 1, 3 or 5 dyes according to the following methods. Each silicon phthalocyanine derivative had maximum excitation and emission wavelengths at 350 nm and 680 nm, respectively. After preparation of each dye-latex, each suspension was diluted to 0.057% solids in either water or tetrahydrofuran. The dye-latex solutions were excited at 350 nm and the fluorescence intensity at 680 nm was measured. The intensity of fluorescence in water divided by the intensity of fluorescence in tetrahydrofuran minus 1 is the degree of quenching of the dyes in the latex particles.

Preparation of One Phthalocyanine Dye in Latex

A solution of PcSi pentafluoro dye (0.02 mg) in tetrahydrofuran (0.1 ml) was added dropwise over 5 minutes to a stirred 2% solids solution of latex particles (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 4°. The dye-latex solution was removed from dialysis and the solids concentration was adjusted to 1.6%.

Preparation of Three Phthalocyanine Dyes in Latex

A solution which consists of PcSi pentafluoro, PcSi trihexyl and PcSi cyano dyes in equimolar amounts to total 0.02 mg dye in tetrahydrofuran (0.1 ml), was added dropwise over 5 minutes to a stirred 2% solids solution of latex particles (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the solids concentration was adjusted to 1.6%.

Preparation of Five Phthalocyanine Dyes in Latex

A solution which consists of PcSi pentafluoro, PcSi trihexyl, PcSi cyano, PcSi vinyl and PcSi methyl ester dyes in equimolar amounts to total 0.02 mg dye in tetrahydrofuran (0.1 ml), was added dropwise over 5 minutes to a stirred 2% solids solution of latex particles solution (1.0 ml). The latex suspension was stirred at room temperature for 6 hours, then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solutions were removed from dialysis and the % solids concentration was adjusted to 1.6%.

The table that follows illustrates the results of the fluorescence experiments.

| Dyes Entrapped | Intensity | % Quenching |
| --- | --- | --- |
| 1 | 413 | 72 |
| 3 | 561 | 56 |
| 5 | 747 | 49 |

The data show that as the number of different dyes entrapped into the latex goes from 1 to 3 to 5, the fluorescence intensity increases because the quenching in the particles decreases.

EXAMPLE 15

Preparation and Characterization of Fluorescence Energy Transfer Dye Latex (Table 1) and Fluorescent Latex Incorporating Hybrid Phthalocyanine Derivatives (Table 2)

A variety of fluorescent energy transfer latexes were prepared with various donor and acceptor dye molecules. Table 1 shows the loading concentrations of the respective donor and acceptor dyes, the mole ratio of the donor and acceptor dyes, the dye loading solvent system as described in Example 10 and the excitation and emission wavelengths and the fluorescence intensity for each particle size at the specified solids concentration. For some of the energy transfer latexes, the same dye pair was incorporated into different diameter latexes. The fluorescence energy transfer efficiency of the entries is greater than 80%. The dye system represented in line 56 is a fluorescence energy transfer compound (FET compound) so that the donor and acceptor pair reside in the molecule before incorporation into latex.

Table 2 shows the characteristics of latex particles incorporated with hybrid phthalocyanine derivatives as described in Example 10 and the fluorescence intensity at the specified solids concentration.

TABLE 1

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
| --- | --- | --- | --- | --- | --- | --- | --- |
| 1. trans-4-[4-(Dibutyl amino) styryl]-1-methyl pyridinium iodide | 0.12 mg/ml | Silicon phthalocyanine bis(dimethylvinyl-silyl-oxide) | 0.1 mg/ml | 2:1 | THF (20%) (0.067 μm) | 340 (0.0019%) | 679 nm (475 nm) |
| 2. trans-4-[4-(Dibutyl amino)styryl]-1-methyl pyridinium iodide | 0.1 mg/ml | Silicon 2,3-naphthalo-cyanine bis(dimethyl-vinylsilyloxide) | 0.23 mg/ml | 1:1 | DMF (70%) (0.067 μm) | 347 (0.057%) | 789 nm (475 nm) |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 3. trans-4-[4-(Dibutyl amino)styryl]-1-methyl pyridinium iodide | 0.1 mg/ml | 1,1'-Dihexyl-3,3,3',3'-tetramethylindo dicarbo-cyanine iodide | 0.144 mg/ml | 1:1 | DMF (70%) (0.067 μm) | 688 (0.057%) | 688 nm (645 nm) |
| 4. Meso-tetra-2-aminophenyl porphine | 0.18 mg/ml | Silicon phthalocyanine bis(dimethylvinyl-silyl-oxide) | 0.1 mg/ml | 2:1 | THF (20%) (0.202 μm) | 1000 (0.00095%) | 679 nm (420 nm) |
| 5. Meso-tetra-2-aminophenyl porphine | 0.1 mg/ml | 1,1'-Dihexyl-3,3,3',3'-tetramethylindo dicarbo-cyanine iodide | 0.098 mg/ml | 1:1 | DMF (70%) (0.067 μm) | 157 (0.0019%) | 676 nm (645 nm) |
| 6. Meso-tetra-2-dimethylaminophenyl porphine | 0.21 mg/ml | Silicon phthalocyanine bis(dimethylvinyl-silyl-oxide) | 0.1 mg/ml | 2:1 | THF (20%) (0.412 μm) | 209 (0.00095%) | 679 nm (430 nm) |
| 7. 3-Ethyl-3'-ethyl carboxyethyl-thiadicarbocyanine iodide | 0.056 mg/ml | Silicon 2,3-naphthalo-cyanine bis(dimethyl-vinylsilyloxide) | 0.25 mg/ml | 4:1 | DMF (70%) (0.067 μm) | 289 (0.057%) | 785 nm (650 nm) |
| 8. 1,1'-Dioctadecyl-3,3,3',3'-tetramethylindodicarbocyanine perchlorate | 0.036 mg/ml | Silicon 2,3-naphthalo-cyanine bis(dimethyl-vinylsilyloxide) | 0.013 mg/ml | 4:1 | DMF (70%) (0.067 μm) | 324 (0.057%) | 787 nm (650 nm) |
| 9. 1,1'-Diethyl-3,3,3',3'-tetramethylindodicarbocyanine iodide | 0.078 mg/ml | Silicon 2,3-naphthalo-cyanine bis(dimethyl-vinylsilyloxide) | 0.025 mg/ml | 6:1 | DMF (70%) (0.067 μm) | 723 (0.057%) | 787 nm (635 nm) |
| 10. 1,1'-Dihexyl-3,3,3',3'-tetramethylindodicarbocyanine iodide | 0.094 mg/ml | Silicon 2,3-naphthalo-cyanine bis(dimethyl-vinylsilyloxide) | 0.025 mg/ml | 6:1 | DMF (70%) (0.067 μm) | 907 (0.057%) | 783 nm (635 nm) |
| 11. 3,3'-Diethyl thiatricarbocyanine iodide | 0.013 mg/ml | Silicon 2,3-naphthalo-cyanine bis(dimethyl-vinylsilyloxide) | 0.025 mg/ml | 1:1 | DMF (70%) (0.067 μm) | 12 (0.057%) | 788 nm (650 nm) |
| 12. 3,3'-Dipropyl thiadicarbocyanine iodide | 0.013 mg/ml | Silicon 2,3-naphthalo-cyanine bis(dimethyl-vinylsilyloxide) | 0.025 mg/ml | 1:1 | DMF (70%) (0.067 μm) | 65 (0.057%) | 788 nm (660 nm) |
| 13. 1,9-Dimethyl-methylene blue, chloride | 0.008 mg/ml | Silicon 2,3-naphthalo-cyanine bis(dimethyl-vinylsilyloxide) | 0.025 mg/ml | 1:1 | DMF (70%) (0.067 μm) | 57 (0.057%) | 788 nm (650 nm) |
| 14. N,N'-Di(3-trimethyl-ammoniumpropyl) thia-dicarbocyanine tribromide | 0.013 mg/ml | Silicon 2,3-naphthalo-cyanine bis(dimethyl-vinylsilyloxide) | 0.025 mg/ml | 1:1 | DMF (70%) (0.067 μm) | 63 (0.057%) | 788 nm (650 nm) |
| 15. 1,1',3,3,3',3'-Hexamethyl-indotricarbocyanine perchlorate | 0.012 mg/ml | Silicon 2,3-naphthalo-cyanine bis(dimethyl-vinylsilyloxide) | 0.025 mg/ml | 1:1 | DMF (70%) (0.067 μm) | 33 (0.057%) | 788 nm (650 nm) |
| 16. N-(3-Triethyl-ammoniumpropyl)-4-(4-(p-dibutylaminophenyl) butadienyl) pyridium, dibromide | 0.014 mg/ml | Silicon 2,3-naphthalo-cyanine bis(dimethyl-vinylsilyloxide) | 0.025 mg/ml | 1:1 | DMF (70%) (0.067 μm) | 55 (0.057%) | 788 nm (500 nm) |
| 17. 1,1',3,3,3',3'-Hexamethyl-4,4'-5,5'-dibenzo-2,2'-indo-tricarbocyanine perchlorate | 0.015 mg/ml | Silicon 2,3-naphthalo-cyanine bis(dimethyl-vinylsilyloxide) | 0.025 mg/ml | 1:1 | DMF (70%) (0.067 μm) | 8 (0.057%) | 788 nm (650 nm) |
| 18. Fluroscein | 0.264 mg/ml | Silicon | 0.1 mg/ml | 6:1 | THF (20%) | 517 | 683 nm |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| | | phthalocyanine bis(dimethylvinyl-silyl-oxide) | | | (0.067 μm) | (0.057%) | (485 nm) |
| 19. Chlorophyll B | 0.087 mg/ml | Silicon 2,3-naphthalo-cyanine bis(dimethyl-vinylsilyloxide) | 0.025 mg/ml | 4:1 | THF (20%) (0.067 μm) | 72 (0.057%) | 783 nm (440 nm) |
| 20. Chlorophyll B | 0.244 mg/ml | Silicon phthalocyanine bis(dimethylvinyl-silyl-oxide) | 0.1 mg/ml | 2:1 | THF (20%) (0.067 μm) | 140 (0.0019%) | 679 nm (440 nm) |
| 21. trans-4-[4-(Dibutyl-amino)styryl]-1-methyl pyridinium iodide | 0.181 mg/ml | Silicon phthalocyanine bis(dimethylpenta-fluorophenyl-silyloxide) + Silicon phthalocyanine bis(dimethylvinyl-silyloxide) | 0.07 mg/ml 0.05 mg/ml | 4:1:1 | THF (20%) (0.067 μm) | 300 (0.0019%) | 681 nm (475 nm) |
| 22. trans-4-[4-(Dibutyl amino) styryl]-1-methyl pyridinium iodide | 0.072 mg/ml | Silicon phthalocyanine bis(trihexylsilyl-oxide) + Silicon phthalocyanine bis(dimethylpenta-fluorophenylsilyl-oxide) + Silicon phthalocyanine bis(dimethylvinyl-silyloxide) | 0.04 mg/ml 0.04 mg/ml 0.03 mg/ml | 4:1:1:1 | THF (20%) (0.067 μm) | 206 (0.0019%) | 681 nm (475 nm) |
| 23. 3-Ethyl-3'-carboxyethylthia-dicarbocyanine iodide | 0.013 mg/ml | Silicon 2,3-naphthalo-cyanine bis(dimethyl-vinylsilyloxide) | 0.025 mg/ml | 1:1 | DMF (70%) (0.067 μm) | 76 (0.057%) | 788 nm (625 nm) |
| 24. 3-Ethyl-3'-ethyl-carboxy-ethyloxathiadicarbocyanine iodide | 0.013 mg/ml | Silicon 2,3-naphthalo-cyanine bis(dimethyl-vinylsilyloxide) | 0.025 mg/ml | 1:1 | DMF (70%) (0.067 μm) | 135 (0.057%) | 788 nm (630 nm) |
| 25. 3,3'-Diethylthia-dicarbocyanine iodide | 0.013 mg/ml | Silicon 2,3-naphthalo-cyanine bis(dimethyl-vinylsilyloxide) | 0.025 mg/ml | 1:1 | DMF (70%) (0.067 μm) | 59 (0.057%) | 787 nm (660 nm) |
| 26. 3,3'-Diethyloxa-dicarbocyanine iodide | 0.012 mg/ml | Silicon 2,3-naphthalo-cyanine bis(dimethyl-vinylsilyloxide) | 0.025 mg/ml | 1:1 | DMF (70%) (0.067 μm) | 57 (0.057%) | 787 nm (590 nm) |
| 27. 1,1'-Dihexyl-3,3,3',3'-tetramethylindodicarbocyanine iodide | 0.094 mg/ml | Silicon 2,3-naphthalo-cyanine bis(dimethyl-vinylsilyloxide) + Silicon naphthalocyanine bis(dimethyl-ethyl-maleimidosilyl-oxide) | 0.025 mg/ml 0.05 mg/ml | 6:1:2 | DMF (50%) (0.431 μm CMLI) | 127 (0.057%) | 788 nm (650 nm) |
| 28. 1,1'-Dihexyl-3,3,3',3'-tetramethylindodicarbocyanine iodide | 0.094 mg/ml | Silicon 2,3-naphthalo-cyanine bis(dimethyl-vinylsilyloxide) + Silicon phthalocyanine bis(dimethylethyl-maleimidosilyl- | 0.025 mg/ml 0.05 mg/ml | 6:1:2 | DMF (50%) (0.431 μm CML) | 193 (0.057%) | 788 nm (635 nm) |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 29. 1,1'-Dihexyl-3,3,3',3'-tetramethylindodicarbocyanine iodide | 0.03 mg/ml | Silicon 2,3-naphthalocyanine bis(dimethylhexylvinylsilyloxide) | 0.05 mg/mL | 1:1 | DMF (50%) (0.431 μm CML) | 275 (0.057%) | 788 nm (650 nm) |
| 30. 1,1'-Dihexyl-3,3,3',3'-tetramethylindodicarbocyanine iodide | 0.1 mg/mL | Silicon 2,3 naphthalocyanine bis(dimethyltriphenylsilyloxide) | 0.2 mg/mL | 1:1 | DMF (50%) (0.431 μm CML) | 163 (0.057%) | 798 nm (650 nm) |
| 31. 1,1'-Dihexyl-3,3,3',3'-tetramethylindodicarbocyanine iodide | 0.09 mg/ml | Silicon naphthalocyanine bis(dimethylretinol) | 0.05 mg/ml | 4:1 | DMF (50%) (0.431 μm CML) | 153 (0.057%) | 790 nm (650 nm) |
| 32. 1,1',3,3,3',3'-Hexamethyl-indotricarbocyanine perchlorate | 0.216 mg/ml | Silicon 2,3-naphthalocyanine bis(dimethylvinylsilyloxide) | 0.1 mg/ml | 4:1 | DMF (50%) (0.431 μm CML) | 0.4 (0.00057%) | 788 nm (635 nm) |
| 33. 1,1'-Dihexyl-3,3,3',3'-tetramethylindodicarbocyanine iodide | 0.512 mg/ml | 1,1',3,3,3',3'-Hexamethyl-indotricarbocyanine perchlorate | 0.1 mg/ml | 4:1 | DMF (50%) (0.431 μm CML) | 0.9 (0.00057%) | 776 nm (635 nm) |
| 34. Lithium tetraacetylide boron complex of 1,1'-Dihexyl-3,3,3',3'-tetramethylindo-dicarbocyanine iodide | 0.16 mg/ml | Silicon 2,3-naphthalocyanine bis(dimethylhexylvinylsilyloxide) | 0.1 mg/ml | 4:1 | DMF (50%) (0.216 μm CML) | 22 (0.00057%) | 788 nm (635 nm) |
| 35. Silicon phthalocyanine bis(dimethylvinylsilyloxide) | 0.334 mg/ml | Silicon 2,3-naphthalocyanine bis(dimethylhexylvinylsilyloxide) | 0.1 mg/ml | 10:1 | DMF (50%) (0.216 μm CML) | 1 (0.00057%) | 800 nm (650 nm) |
| 36. 1,1',3,3,3',3'-Hexamethylindotricarbocyanine perchlorate | 0.23 mg/ml | Silicon 2,3-naphthalocyanine bis(dimethylhexylvinylsilyloxide) | 0.1 mg/ml | 10:1 | DMF (50%) (0.216 μm CML) | 0.4 (0.00057%) | 780 nm (635 nm) |
| 37. 1,1',3,3,3',3'-Hexamethylindotricarbocyanine perchlorate | 0.19 mg/ml | Silicon octaethoxy 2,3-naphthalocyanine bis(dimethylhexylvinylsilyl-oxide) | 0.1 mg/ml | 10:1 | DMF (50%) (0.216 μm CML) | 0.7 (0.00057%) | 780 nm (635 nm) |
| 38. Oxazine 1 perchlorate | 0.01 mg/ml | Silicon 2,3-naphthalocyanine bis(dimethylvinylsilyloxide) | 0.025 mg/ml | 1:1 | DMF (70%) (0.067 μm) | 291 (0.057%) | 788 nm (650 nm) |
| 39. 3,3'-Dipropyl-thiadicarbocyanine iodide | 0.232 mg/ml | Silicon 2,3-naphthalocyanine bis(dimethylvinylsilyloxide) | 0.1 mg/ml | 4:1 | DMF (50%) (0.431 μm CML) | 0.4 (0.00057%) | 788 nm (635 nm) |
| 40. Copper tetra-tert-butyl phthalocyanine | 0.72 mg/ml | Silicon 2,3-naphthalocyanine bis(dimethylhexylvinylsilyloxide) | 0.1 mg/ml | 1:1 | DMF (50%) (0.216 μm CML) | 0.2 (0.00057%) | 788 nm (650 nm) |
| 41. (E,E)-3,5-bis-(4-phenyl-1,3-butadienyl)-4,4-difluoro-4-bora-3a,4a-diazo-s-indacene | 0.16 mg/ml | Silicon 2,3-naphthalocyanine bis(dimethylhexylvinylsilyloxide) | 0.1 mg/ml | 4:1 | DMF (50%) (0.216 μm CML) | 42 (0.00057%) | 785 nm (670 nm) |
| 42. Aluminum tetra-tert-butyl | 0.28 mg/ml | Silicon 2,3- | 0.1 mg/ml | 4:1 | THF (50%) | 0.5 | 788 nm |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| phthalocyanine hydroxide | | naphthalo-cyanine bis(dimethyl-hexylvinyl-silyloxide) | | | (0.216 μm CML) | (0.00057%) | (650 nm) |
| 43. Aluminum tetra-tert-butylphthalocyanine chloride | 0.29 mg/ml | Silicon 2,3-naphthalo-cyanine bis(dimethyl-hexylvinyl-silyloxide) | 0.1 mg/ml | 4:1 | DMF (50%) (0.216 μm CML) | 0.1 (0.00057%) | 788 nm (650 nm) |
| 44. (E,E)-3,5-bis-(4-phenyl-1,3-butadienyl)-4,4-difluoro-4-bora-3a,4a-diazo-s-indacene | 0.14 mg/ml | Aluminum octabutoxy-phthalocyanine triethylsilyloxide | 0.1 mg/ml | 4:1 | THF (50%) (0.216 μm CML) | 1.8 (0.00057%) | 774 nm (650 nm) |
| 45. Iron phthalocyanine bis(tert-butyl isocyanide) | 0.26 mg/ml | Silicon 2,3-naphthalo-cyanine bis(dimethyl-hexylvinyl-silyloxide) | 0.1 mg/ml | 4:1 | THF (50%) (0.216 μm CML) | 0.3 (0.00057%) | 788 nm (670 nm) |
| 46. (E,E)-3,5-bis-(4-phenyl-1,3-butadienyl)-4,4-difluoro-4-bora-3a,4a-diazo-s-indacene | 0.16 mg/ml | Octabutoxy-phthalocyanine | 0.1 mg/ml | 4:1 | THF (50%) (0.216 μm CML) | 0.7 (0.00057%) | 783 nm (670 nm) |
| 47. (E,E)-3,5-bis-(4-phenyl-1,3-butadienyl)-4,4-difluoro-4-bora-3a,4a-diazo-s-indacene | 0.15 mg/ml | Silicon 2,3-naphthalo-cyanine bis(dimethyl-phenylpenta-fluoro-silyloxide) | 0.1 mg/ml | 4:1 | THF (50%) (0.216 μm CML) | 16.9 (0.00057%) | 783 nm (670 nm) |
| 48. (E,E)-3,5-bis-(4-phenyl-1,3-butadienyl)-4,4-difluoro-4-bora-3a,4a-diazo-s-indacene | 0.19 mg/ml | Silicon 2,3-naphthalo-cyanine bis(dimethyl-vinylsilyloxide) | 0.1 mg/ml | 4:1 | THF (50%) (0.216 μm CML) | 31.5 (0.00057%) | 783 nm (670 nm) |
| 49. (E,E)-3,5-bis-(4-phenyl-1,3-butadienyl)-4,4-difluoro-4-bora-3a,4a-diazo-s-indacene | 0.15 mg/ml | Silicon 2,3-naphthalo-cyanine bis(diphenylvinyl-silyloxide) | 0.1 mg/ml | 4:1 | THF (50%) (0.216 μm CML) | 13.1 (0.00057%) | 783 nm (670 nm) |
| 50. (E,E)-3,5-bis-(4-phenyl-1,3-butadienyl)-4,4-difluoro-4-bora-3a,4a-diazo-s-indacene | 0.15 mg/ml | Silicon 2,3-naphthalo-cyanine bis(dimethyl-maleimido-ethoxysilyl-oxide) | 0.1 mg/ml | 4:1 | THF (50%) (0.216 μm CML) | 4.7 (0.00057%) | 783 nm (670 nm) |
| 51. (E,E)-3,5-bis-(4-phenyl-1,3-butadienyl)-4,4-difluoro-4-bora-3a,4a-diazo-s-indacene | 0.14 mg/ml | Silicon 2,3-naphthalo-cyanine bis(dimethylsilyl-oxide-trans-stilbene) | 0.1 mg/ml | 4:1 | THF (50%) (0.216 μm CML) | 11.7 (0.00057%) | 783 nm (670 nm) |
| 52. (E,E)-3,5-bis-(4-phenyl-1,3-butadienyl)-4,4-difluoro-4-bora-3a,4a-diazo-s-indacene | 0.12 mg/ml | Silicon 2,3-naphthalo-cyanine bis(tri-decafluoro-1,1,2,2-tetra-hydrooctyl-1-dimethyl-silyl-oxide) | 0.1 mg/ml | 4:1 | THF (50%) (0.216 μm CML) | 22.3 (0.00057%) | 783 nm (670 nm) |
| 53. (E,E)-3,5-bis-(4-phenyl-1,3-butadienyl)-4,4-difluoro-4-bora-3a,4a-diazo-s-indacene | 0.12 mg/ml | Silicon 2,3-naphthalo-cyanine bis(dimethyl-retinol) | 0.1 mg/ml | 4:1 | THF (50%) (0.216 μm CML) | 16.1 (0.00057%) | 783 nm (670 nm) |
| 54. Germanium tetra-tert-butyl-phthalocyanine dihydroxide | 0.3 mg/ml | Silicon 2,3-naphthalo-cyanine bis(dimethyl-hexylvinyl-silyloxide) | 0.1 mg/ml | 4:1 | THF (50%) (0.216 μm CML) | 1.3 (0.00057%) | 783 nm (670 nm) |
| 55. Germanium tetra-tert-butyl phthalocyanine dichloride | 0.3 mg/ml | Silicon 2,3-naphthalo- | 0.1 mg/ml | 4:1 | THF (50%) (0.216 μm CML) | 0.6 (0.00057%) | 783 nm (670 nm)5 |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| | | cyanine bis(dimethyl-hexylvinyl-silyloxide) | | | CML) | | |
| 56. Silicon phthalocyanine bis (maleimide-fluoroscein) FET COMPOUND | 0.15 mg/ml | Silicon phthalocyanine bis(maleimide-fluoroscein) FET COMPOUND | | | THF (20%) (0.067 μm) | 209 (0.0019%) | 681 nm (470 nm) |
| 57. 3,3'-Diethylthia-tricarbocyanine iodide | 0.57 mg/ml | 5,5'-Dichloro-1,1'-diphenylamino-3,3'-diethyl-10,12-ethylene-thiatricarbocyanine-iodide | 0.1 mg/ml | 4:1 | DMF (50%) (0.216 μm CML) | 0.048 nA (0.00057%) | 832 nm (670 nm) |
| 58. 1,1',3,3,3',3'-Hexamethylindotricarbocyanine perchlorate | 0.61 mg/ml | 5,5'-Dichloro-1,1'-diphenylamino-3,3'-diethyl-10,12-ethylene-thiatricarbocyanine iodide | 0.1 mg/ml | 4:1 | DMF (50%) (0.216 μm CML) | 0.149 nA (0.00057%) | 832 nm (670 nm) |
| 59. 1,1',3,3,3',3'-Hexamethyl-4,4',5,5'-dibenzo-2,2'-indo-tricarbocyanine perchlorate | 0.51 mg/ml | 5,5'-Dichloro-1,1'-diphenylamino-3,3'-diethyl-10,12-ethylene-thiatricarbocyanine iodide | 0.1 mg/ml | 4:1 | DMF (50%) (0.216 μm CML) | 0.046 nA (0.00057%) | 832 nm (670 nm) |
| 60. 1,1'-Dihexyl-3,3,3',3'-tetramethylindodicarbocyanine iodide | 0.23 mg/ml | Silicon 2,3-naphthalo-cyanine bis(dimethyl-hexylvinyl-silyloxide) | 0.1 mg/ml | 4:1 | DMF (50%) (0.216 μm CML) | 14.12 nA (0.00057%) | 783 nm (670 nm) |
| 61. (E,E)-3,5-bis-(4-phenyl-1,3-butadienyl)-4,4-difluoro-4-bora-3a,4a-diazo-s-indacene | 0.16 mg/ml | Silicon 2,3-naphthalo-cyanine bis(dimethyl-hexylvinyl-silyloxide) | 0.1 mg/ml | 4:1 | DMF (50%) (0.216 μm CML) | 5.00 nA (0.00057%) | 783 nm (670 nm) |
| 62. (E,E)-3,5-bis-(4-phenyl-1,3-butadienyl)-4,4-difluoro-4-bora-3a,4a-diazo-s-indacene | 0.26 mg/ml | Silicon octaethoxy 2,3-naphthalocyanine bis(di-methyl-hexylvinylsilyl-oxide) | 0.1 mg/ml | 4:1 | DMF (50%) (0.216 μm CML) | 2.74 nA (0.00057%) | 858 nm (670 nm) |
| 63. (E,E)-3,5-bis-(4-phenyl-1,3-butadienyl)-4,4-difluoro-4-bora-3a,4a-diazo-s-indacene | 0.32 mg/ml | Octabutoxy-phthalocyanine | 0.1 mg/ml | 4:1 | DMF (50%) (0.216 μm CML) | 4.07 nA (0.00057%) | 762 nm (670 nm) |
| 64. (E,E)-3,5-bis-(4-phenyl-1,3-butadienyl)-4,4-difluoro-4-bora-3a,4a-diazo-s-indacene | 0.28 mg/ml | Octabutoxy-naphthalocyanine | 0.1 mg/ml | 4:1 | DMF (50%) (0.216 μm CML) | 1.76 nA (0.00057%) | 772 nm (670 nm) |
| 65. 1,1'-Dihexyl-3,3,3',3'-tetramethylindodicarbocyanine iodide | 0.19 mg/ml | Silicon octaethoxy 2,3-naphthalo-cyanine bis(di-methylhexylvinyl-silyl-oxide) | 0.1 mg/ml | 4:1 | DMF (50%) (0.216 μm CML) | 0.712 nA (0.00057%) | 858 nm (670 nm) |
| 66. 3,3'-Diethylthia-tricarbocyanine iodide | 0.16 mg/ml | Silicon octaethoxy2,3-naphthalo-cyanine bis(di-methylhexylvinyl-silyl-oxide) | 0.1 mg/ml | 4:1 | DMF (50%) (0.216 μm CML) | 0.058 nA (0.00057%) | 858 nm (670 nm) |
| 67. 1,1',3,3,3',3'-Hexamethylindotricarbocyanine perchlorate | 0.15 mg/ml | Silicon octaethoxy 2,3-naphthalo-cyanine bis(di-methylhexylvinyl-silyl-oxide) | 0.1 mg/ml | 4:1 | DMF (50%) (0.216 μm CML) | 0.141 nA (0.00057%) | 858 nm (670 nm) |
| 68. 1,1',3,3,3',3'-Hexamethyl-4,4',5,5'-dibenzo-2,2'-indo-tricarbocyanine perchlorate | 0.19 mg/ml | Silicon octaethoxy 2,3-naphthalo-cyanine bis(di- | 0.1 mg/ml | 4:1 | DMF (50%) (0.216 μm CML) | 0.058 nA (0.00057%) | 858 nm (670 nm) |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) (% SOLID) | INTENSITY | EMISSION MAXIMUM (EXCIT.) |
|---|---|---|---|---|---|---|---|
| 69. (E,E)-3,5-bis-(4-phenyl-1,3-butadienyl)-4,4-difluoro-4-bora-3a,4a-diazo-s-indacene | 0.2 mg/ml | methylhexylvinyl-silyl-oxide) Silicon octaethoxy 2,3-naphthalo-cyanine bis(di-methylhexylvinyl-silyl-oxide) | 0.15 mg/ml | 4:1 | THF (50%) (0.216 μm CML) | 2.720 nA (0.00057%) | 858 nm (670 nm) |
| 70. (E,E)-3,5-bis-(4-phenyl-1,3-butadienyl)-4,4-difluoro-4-bora-3a,4a-diazo-s-indacene | 0.16 mg/ml | Silicon 2,3-naphthalo-cyanine bis(dimethylhexyl-vinylsilyloxide) + Silicon octaethoxy 2,3-naphthalo-cyanine bis(di-methylhexyl-vinylsilyloxide) | 0.1 mg/ml 0.12 mg/ml | 4:1:1 | THF (50%) (0.216 μm CML) | 2.38 nA (0.00057%) | 858 nm (670 nm) |
| 71. Silicon phthalocyanine bis(di-methylvinylsilyloxide) | 0.36 mg/ml | 5,5'-Dichloro-1,1'-diphenyl-amino-3,3'-diethyl-10,12-ethylene-thiatri-carbocyanine perchlorate | 0.1 mg/ml | 4:1 | THF (50%) (0.216 μm CML) | 8.10 nA (0.00057%) | 832 nm (670 nm) |
| 72. Tetrakis(4-cumyl-phenoxy) phthalocyanine | 0.48 mg/ml | Silicon 2,3-naphthalo-cyanine bis(dimethylhexyl-vinylsilyloxide) | 0.1 mg/ml | 4:1 | THF (50%) (0.216 μm CML) | 0.397 nA (0.00057%) | 783 nm (670 nm) |
| 73. Tetrakis(4-cumyl-phenoxy) phthalocyanine | 0.68 mg/ml | 5,5'-Dichloro-1,1'-diphenylamino-3,3'-diethyl-10,12-ethylene-thiatricarbo-cyanine perchlorate | 0.1 mg/ml | 4:1 | THF (50%) (0.216 μm CML) | 0.128 nA (0.00057%) | 832 nm (670 nm) |
| 74. Tetrakis(phenylthio) phthalocyanine | 0.34 mg/ml | Silicon 2,3-naphthalo-cyanine bis(dimethyl-hexylvinyl-silyloxide) | 0.1 mg/ml | 4:1 | THF (50%) (0.216 μm CML) | 0.374 nA (0.00057%) | 788 nm (670 nm) |
| 75. Tetrakis(phenylthio) phthalocyanine | 0.28 mg/ml | 5,5'-Dichloro-1,1'-diphenylamino-3,3'-diethyl-10,12-ethylene-thiatricarbo-cyanine perchlorate | 0.1 mg/ml | 4:1 | THF (50%) (0.216 μm CML) | 0.109 nA (0.00057%) | 832 nm (670 nm) |
| 76. (E,E)-3,5-bis-(4-phenyl-1,3-butadienyl)-4,4-difluoro-4-bora-3a,4a-diazo-s-indacene | 0.24 mg/ml | Tin octabutoxy 2,3-naphthalo-cyanine dichloride | 0.1 mg/ml | 4:1 | THF (50%) (0.216 μm CML) | 1.724 nA (0.00057%) | >900 nm (670 nm) |
| 77. Tetrakis (4-cumylphenoxy) phthalocyanine | 0.36 mg/ml | Tin octabutoxy 2,3-naphthalo-cyanine dichloride | 0.1 mg/ml | 4:1 | THF (50%) (0.216 μm CML) | 0.162 nA (0.00057%) | >900 nm (670 nm) |
| 78. Tetrakis(phenylthio) phthalocyanine | 0.26 mg/ml | Tin octabutoxy 2,3-naphthalo-cyanine dichloride | 0.1 mg/ml | 4:1 | THF (50%) (0.216 μm CML) | 0.061 nA (0.00057%) | >900 nm (670 nm) |
| 79. Germanium tetra-tert-butyl phthalocyanine dihydroxide | 0.42 mg/ml | 5,5'-Dichloro-1,1'-diphenylamino-3,3'-diethyl-10,12-ethylene-thiatricarbo-cyanine perchlorate | 0.1 mg/ml | 4:1 | THF (50%) (0.216 μm CML) | 0.109 nA (0.00057%) | >900 nm (670 nm) |
| 80. Germanium tetra-tert-butyl phthalocyanine dihydroxide | 0.22 mg/ml | Tin octabutoxy 2,3-naphthalo-cyanine dichloride | 0.1 mg/ml | 4:1 | THF (50%) (0.216 μm CML) | 0.045 nA (0.00057%) | >900 nm (670 nm) |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 81. Germanium tetra-tert-butyl phthalocyanine dihydroxide | 0.2 mg/ml | Tin octabutoxy 2,3-naphthalocyanine bis(triethylsilyloxide) | 0.1 mg/ml | 4:1 | THF (50%) (0.216 μm CML) | 0.042 nA (0.00057%) | >900 nm (670 nm) |
| 82. Germanium tetra-tert-butyl phthalocyanine dichloride | 0.42 mg/ml | 5,5'-Dichloro-1,1'-diphenylamino-3,3'-diethyl-10,12-ethylene-thiatricarbocyanine perchlorate | 0.1 mg/ml | 4:1 | THF (50%) (0.216 μm CML) | 0.081 nA (0.00057%) | 832 nm (670 nm) |
| 83. Germanium tetra-tert-butyl phthalocyanine dichloride | 0.22 mg/ml | Tin octabutoxy 2,3-naphthalocyanine dichloride | 0.1 mg/ml | 4:1 | THF (50%) (0.216 μm CML) | 0.052 nA (0.00057%) | >900 nm (670 nm) |
| 84. Germanium tetra-tert-butyl phthalocyanine dichloride | 0.2 mg/ml | Tin octabutoxy 2,3-naphthalocyanine bis(triethylsilyl-oxide) | 0.1 mg/ml | 4:1 | THF (50%) (0.216 μm CML) | 0.050 nA (0.00057%) | >900 nm (670 nm) |
| 85. (E,E)-3,5-bis-(4-phenyl-1,3-butadienyl)-4,4-difluoro-4-bora-3a,4a-diaza-s-indacene | 0.16 mg/ml | Silicon 2,3-naphthalocyanine bis(dimethylhexyl-vinylsilyloxide) + 5,5'-Dichloro-1,1'-diphenyl-amino-3,3'-diethyl-10,12-ethylene-thiatricarbocyanine perchlorate | 0.1 mg/ml 0.072 mg/ml | 4:1:1 | THF (50%) (0.216 μm CML) | 0.315 nA (0.00057%) | 858 nm (670 nm) |
| 86. (E,E)-3,5-bis-(4-phenyl-1,3-butadienyl)-4,4-difluoro-4-bora-3a,4a-diaza-s-indacene | 0.24 mg/ml | 5,5'-Dichloro-1,1'-diphenyl-amino-3,3'-diethyl-10,12-ethylene-thiatricarbocyanine perchlorate | 0.1 mg/ml | 4:1 | THF (50%) (0.216 μm CML) | 2.230 nA (0.00057%) | 832 nm (670 nm) |
| 87. 1,1'-Dihexyl-3,3,3',3'-tetramethyl-indodicarbocyanine iodide | 0.34 mg/ml | 5,5'-Dichloro-1,1'-diphenylamino-3,3'-diethyl-10,12-ethylene-thiatricarbocyanine perchlorate | 0.1 mg/ml | 4:1 | THF (50%) (0.216 μm CML) | 0.545 nA (0.00057%) | 823 nm (670 nm) |
| 88. (E,E)-3,5-bis-(4-phenyl-1,3-butadienyl)-4,4-difluoro-4-bora-3a,4a-diaza-s-indacene | 0.16 mg/ml | Silicon 2,3-naphthalocyanine bis(dimethyl-hexylvinyl-silyloxide) + Silicon 2,3-naphthalocyanine bis(dimethylpenta-fluorophenyl-silyloxide) | 0.07 mg/ml 0.07 mg/ml | 4:1:1 | THF (50%) (0.216 μm CML) | 49 (0.00057%) | 783 nm (670 nm) |
| 89. Silicon phthalocyanine bis(dimethylhexylvinylsilyloxide) | 1.0 mg/ml | Silicon octaethoxy 2,3-naphthalocyanine bis(di-methylhexylvinyl-silyl-oxide) | 1.0 mg/ml | 1.5:1 | THF (50%) (0.216 μm CML) | 0.4 (0.00057%) | 858 nm (670 nm) |
| 90. Silicon phthalocyanine bis(dimethylhexylvinylsilyloxide) | 1.0 mg/ml | Silicon 2,3-naphthalocyanine bis(dimethylhexyl-vinylsilyloxide) + Silicon octaethoxy 2,3-naphthalocyanine bis(dimethylhexyl-vinylsilyl-oxide) | 1.0 mg/ml 1.0 mg/ml | 1.5:1.2:1 | THF (50%) (0.216 μm CML) | 0.4 (0.00057%) | 854 nm (670 nm) |
| 91. Silicon phthalocyanine | 1.0 mg/ml | Silicon 2,3- | 0.1 mg/ml | 9.7:1 | THF (50%) | 155.8 | 785 nm |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| bis(trihexylsilyloxide) | | naphthalocyanine bis(dimethylhexyl-vinylsilyloxide) | | | (0.216 μm CML) | (0.00057%) | (670 nm) |
| 92. Silicon phthalocyanine bis[(3-cyanpropyl) dimethylsilyloxide] | 1.0 mg/ml | Silicon 2,3-naphthalocyanine bis(dimethylhexyl-vinylsilyloxide) | 0.1 mg/ml | 13.5:1 | THF (50%) (0.216 μm CML) | 23.2 (0.00057%) | 785 nm (670 nm) |
| 93. Silicon phthalocyanine bis(dimethylpentafluorophenylsilyl-oxide) | 1.0 mg/ml | Silicon 2,3-naphthalocyanine bis(dimethylhexyl-vinylsilyloxide) | 0.1 mg/ml | 10.1:1 | THF (50%) (0.216 μm CML) | 14.5 (0.00057%) | 785 nm (670 nm) |
| 94. Silicon phthalocyanine dimethylpentafluorosilyloxide trihexylsilyloxide | 1.0 mg/ml | Silicon 2,3-naphthalocyanine bis(dimethylhexyl-vinylsilyloxide) | 0.1 mg/ml | 10:3:1 | THF (50%) (0.216 μm CML) | 70.5 (0.00057%) | 785 nm (670 nm) |
| 95. Silicon phthalocyanine bis[10-carbomethoxydecyl) dimethylsilyloxide] | 1.0 mg/ml | Silicon 2,3-naphthalocyanine bis(dimethylhexyl-vinylsilyloxide) | 0.1 mg/ml | 10.2:1 | THF (50%) (0.216 μm CML) | 200.8 (0.00057%) | 785 nm (670 nm) |
| 96. Silicon phthalocyanine bis(dimethylhexylvinylsilyloxide) | 1.0 mg/ml | Silicon 2,3-naphthalocyanine bis(trihexylsilyl-oxide) | 0.1 mg/ml | 14.7:1 | THF (50%) (0.216 μm CML) | 126.8 (0.00057%) | 780 nm (670 nm) |
| 97. Silicon phthalocyanine [(10-carbomethoxydecyl) dimethylsilyloxide] (dimethylvinylsilyloxide) | 1.0 mg/ml | Silicon 2,3-naphthalocyanine bis(dimethylhexyl-vinylsilyloxide) | 0.1 mg/ml | 12.1:1 | THF (50%) (0.216 μm CML) | 207.7 (0.00057%) | 785 nm (670 nm) |
| 98. Silicon phthalocyanine bis(dimethylhexylsilyloxide) | 1.0 mg/ml | Silicon 2,3-naphthalocyanine bis(dimethyloctyl-decylsilyloxide) | 0.1 mg/ml | 15.3:1 | THF (50%) (0.216 μm CML) | 262.8 (0.00057%) | 780 nm (670 nm) |
| 99. Silicon phthalocyanine [(10-carbomethoxydecyl) dimethylsilyloxide] (dimethylvinylsilyloxide) | 1.0 mg/ml | Silicon 2,3-naphthalocyanine bis(trihexylsilyl-oxide) | 0.1 mg/ml | 14.6:1 | THF (50%) (0.216 μm CML) | 117.2 (0.00057%) | 780 nm (670 nm) |
| 100. Silicon phthalocyanine bis(dimethylhexylvinylsilyloxide) | 1.0 mg/ml | Silicon [di(1,6-diphenyl-2,3-naphthalocyanine)] (2,3-naphtalo-cyanine) phthalocyanine bis(dimethylhexyl-vinylsilyloxide) | 1.0 mg/ml | 1.5:1 | THF (50%) (0.216 μm CML) | 177.6 (0.00057%) | 770 nm (670 nm) |
| 101. Silicon phthalocyanine bis(dimethylhexylvinylsilyloxide) | 1.0 mg/ml | Silicon [di(1,6-diphenyl-2,3-naphthalocyanine)] di(2,3-tert-butylphthalocyanine bis(dimethylhexyl-vinylsilyloxide) | 1.0 mg/ml | 1.6:1 | THF (50%) (0.216 μm CML) | 141.3 (0.00057%) | 760 nm (670 nm) |
| 102. Silicon phthalocyanine bis(dimethylhexylvinylsilyloxide) | 1.0 mg/ml | Silicon [di(2,3-naphthlocyanine)] di(1,4-diphenylthalo cyanine) bis(dimethylhexyl-vinylsilyloxide) | 1.0 mg/ml | 1.4:1 | THF (50%) (0.216 μm CML) | 66.5 (0.00057%) | 780 nm (670 nm) |
| 103. Silicon phthalocyanine bis(dimethylhexylvinylsilyloxide) | 1.0 mg/ml | Silicon [di(1,6-diphenyl-2,3-naphthlocyanine)] diphthalocyanine bis(trihexylsilyl-oxide) | 1.0 mg/ml | 1.5:1 | THF (50%) (0.216 μm CML) | 259.3 (0.00057%) | 760 nm (670 nm) |
| 104. Silicon phthalocyanine bis(dimethylhexylvinylsilyloxide) | 1.0 mg/ml | Silicon [di(1,6-diphenyl-2,3-naphthalocyanine)] di(2,3-dicyanophthalo-cyanine) bis(dimethylhexyl-vinylsilyloxide) | 1.0 mg/ml | 1.5:1 | THF (50%) (0.216 μm CML) | 7.7 (0.00057%) | 843 nm (670 nm) |
| 105. Silicon phthalocyanine bis(dimethylvinylsilyloxide) | 1.0 mg/ml | Silicon 2,3-naphthalocyanine bis(dimethylhexyl- | 0.1 mg/ml | 15:1 | THF (50%) (0.216 μm CML) | 55.5 (0.00057%) | 785 nm (670 nm) |

TABLE 1-continued

| DONOR DYE | LOADING CONC. (mg/ml) | ACCEPTOR DYE | LOADING CONC. (mg/ml) | MOLE DONOR: MOLE ACCEPTOR | SOLVENT SYSTEM (LATEX SIZE) | INTENSITY (% SOLID) | EMISSION MAXIMUM (EXCIT.) |
|---|---|---|---|---|---|---|---|
| 106. Silicon phthalocyanine bis(dimethylhexylvinylsilyloxide) | 10.4 mg/ml | Silicon [di(1,6-diphenylnaphthalo-cyanine)] diphthalocyanine bis(dimethylhexyl-vinylsilyloxide) + Silicon 2,3-naphthalocyanine bis(dimethylhexyl-vinylsilyloxide) | 1.0 mg/ml 0.1 mg/ml | 15:1:0.11 | THF (70%) (0.216 μm CML) | 503 (0.00057%) | 785 nm (670 nm) |
| 107. Silicon phthalocyaine bis(dimethylhexylvinylsilyloxide) | 10.4 mg/ml | Silicon [di(1,6-diphenylnaphthalo-cyanine)] diphthalocyanine bis(dimethylhexyl-vinylsilyloxide) | 1.0 mg/ml | 15:1 | THF (70%) (0.216 μm CML) | 750 (0.00057%) | 760 nm (670 nm) |
| 108. Silicon phthalocyanine bis(dimethylhexylvinylsilyloxide) | 1.2 mg/ml | Silicon 2,3-naphthalocyanine bis(dimethylhexyl-vinylsilyloxide) | 0.1 mg/ml | 15:1 | THF (50%) (0.216 μm CML) | 335 (0.00057%) | 785 nm (670 nm) |
| 109. Silicon phthalocyanine bis(dimethylhexylvinylsilyloxide) | 5.2 mg/ml | Silicon [di(1,6-diphenylnaphthalo-cyanine)] diphthalocyanine bis(dimethylhexyl-vinylsilyloxide) + Silicon [di(1,6-diphenylnaphthalo-cyanine)] dinaphthalocyanine bis(dimethylhexyl-vinylsilyloxide) | 0.5 mg/ml 0.1 mg/ml | 15:1:0.19 | THF (70%) (0.216 μm CML) | 410 (0.00057%) | 798 nm (670 nm) |
| 110. Silicon phthalocyanine bis(dimethylhexylvinylsilyloxide) | 4.8 mg/ml | Silicon [di(1,6-diphenylnaphthalo-cyanine)] dinaphthalocyanine bis(dimethylhexyl-vinylsilyloxide) | 0.5 mg/ml | 15:1 | THF (70%) (0.216 μm CML) | 409 (0.00057%) | 798 nm (670 nm) |

TABLE 2

| HYBRID COMPOUND | LOADING CONC. (mg/ml) | SOLVENT SYSTEM | LATEX SIZE | % SOLID | INTENSITY | EMISSION MAXIMUM | EXCITATION |
|---|---|---|---|---|---|---|---|
| 1. Silicon [di(1,6-diphenylnaphthalocyanine)] diphthalocyanine bis(dimethylhexylvinylsilyl-oxide) | 2.0 mg/ml | THF | 0.216 μm CML | 0.00057% | 50 | 760 nm | 650 nm |
| 2. Silicon [di(1,6-diphenylnaphthalocyanine)] tetrafluorophthalocyanine phthalocyanine bis(dimethylhexylvinylsilyloxide) | 2.0 mg/ml | THF | 0.216 μm CML | 0.00057% | 0.7/0.5 | 765 nm/ 825 nm | 650 nm |
| 3. Silicon [di(1,6-diphenylnaphthalocyanine)] tetrafluorophthalocyanine phthalocyanine bis(dimethylpentafluorophenylsilyloxide) | 1.5 mg/ml | THF | 0.216 μm CML | 0.00057% | 0.5/0.3 | 770 nm/ 839 nm | 650 nm |
| 4. Silicon [di(1,6-diphenylnaphthalocyanine)] diphthalocyanine bis(dimethylpentafluoro-phenylsilyloxide) | 0.1 mg/ml | THF | 0.216 μm CML | 0.00057% | 0.2 | 775 nm | 650 nm |
| 5. Silicon [di(1,6-diphenylnaphthalocyanine)] di(tert-butylphthalocyanine) bis(dimethylhexylvinylsilyloxide) | 1.5 mg/ml | THF | 0.216 μm CML | 0.00057% | 7 | 758 nm | 650 nm |
| 6. Silicon [di(2,3-naphthalocyanine)] di(1,4-diphenylphthalocyanine) bis(dimethylhexylvinylsilyloxide) | 1.0 mg/ml | THF | 0.216 μm CML | 0.00057% | 7 | 779 nm | 650 nm |
| 7. Silicon [di(2,3-naphthalocyanine] di(1,4-diphenylphthalocyanine) bis(dimethylpentafluorophenylsilyloxide) | 2.0 mg/ml | THF | 0.216 μm CML | 0.00057% | 6 | 792 nm | 650 nm |
| 8. Silicon [di(1,6-diphenyl-2,3-naphthalo-cyanine)] di(2,3-tert-butylphthalocyanine) bis(dimethylhexylvinylsilyloxide) | 2.0 mg/ml | THF | 0.216 μm CML | 0.00057% | 43 | 757 nm | 650 nm |
| 9. Silicon [di(1,6-diphenyl-2,3-naphthalo- | 0.4 mg/ml | THF | 0.216 μm CML | 0.00057% | 2 | 770 nm | 660 nm |

TABLE 2-continued

| HYBRID COMPOUND | LOADING CONC. (mg/ml) | SOLVENT SYSTEM | LATEX SIZE | % SOLID | INTENSITY | EMISSION MAXIMUM | EXCITATION |
|---|---|---|---|---|---|---|---|
| cyanine)] di(2,3-tert-butylphthalocyanine) bis(dimethylpentafluorophenylsilyloxide) | | | | | | | |
| 10. Silicon [di(1,6-diphenyl-2,3-naphthalocyanine)] diphthalocyanine bis(trihexylsilyloxide) | 1.5 mg/ml | THF | 0.216 μm CML | 0.00057% | 58 | 757 nm | 650 nm |
| 11. Silicon [di(1,6-diphenyl-2,3-naphthalocyanine)] dinaphthalocyanine bis(dimethylhexylvinylsilyloxide) | 0.2 mg/ml | THF | 0.216 μm CML | 0.00057% | 15 | 798 nm | 350 nm |
| 12. Silicon (1,6-diphenyl-2,3-naphthalocyanine)] triphthalocyanine bis(dimethylhexylvinylsilyloxide) | 0.8 mg/ml | THF | 0.216 μm CML | 0.00057% | 74 | 720 nm | 630 nm |
| 13. Silicon [di(1,6-diphenyl-2,3-naphthalocyanine)] (2,3-naphthalocyanine) phthalocyanine bis(dimethylhexylvinylsilyloxide) | 2.0 mg/ml | THF | 0.216 μm CML | 0.00057% | 34 | 770 nm | 675 nm |
| 14. Silicon [di(2,3-naphthalocyanine)] di(2,3-dicyanophthalocyanine) bis(dimethylhexylvinylsilyloxide) | 0.1 mg/ml | THF | 0.216 μm CML | 0.00057% | 1 | 800 nm | 650 nm |
| 15. Silicon [di(1,6-diphenylnaphthalocyanine)] di(dichlorophthalocyanine | 0.5 mg/ml | THF | 0.216 μm CML | 0.00057% | 8 | 790 nm | 650 nm |
| 16. Silicon [di(1,6-diphenyl-2,3-naphthalocyanine)] diphthalocyanine bis[poly(ethylene glycol) methyl ester] | 0.5 mg/ml | THF | 0.216 μm CML | 0.00057% | 1 | 764 nm | 660 nm |
| 17. Silicon [di(1,6-diphenyl-2,3-naphthalocyanine)] diphthalocyanine dihydroxide | 0.4 mg/ml | THF | 0.216 μm CML | 0.00057% | 2 | 768 nm | 670 nm |
| 18. Silicon [di(1,6-diphenyl-2,3-naphthalocyanine)] diphthalocyanine bis(octyloxide) | 1.0 mg/ml | THF | 0.216 μm CML | 0.00057% | 17 | 766 nm | 650 nm |
| 19. Silicon [di(1,6-diphenyl-2,3-naphthalocyanine)] diphthalocyanine bis(phenoxide) | 0.5 mg/ml | THF | 0.216 μm CML | 0.00057% | 1.0 | 777 nm | 660 nm |
| 20. Silicon trinaphthalocyanine dichlorophthalocyanine bis(dimethylhexylvinylsilyloxide) | 0.5 mg/ml | THF | 0.216 μm CML | 0.00057% | 11 | 782 nm | 660 nm |

EXAMPLE 16

Adsorption of Anti-Human Chorionic Gonadotropin (hCG) Antibody to Latex Particles A typical example of the adsorptions of an antibody to dyed latex particles, prepared as described in Example 10, and of a complementary antibody to undyed latex particles, both of which can be used in a sandwich assay for hCG, is outlined below. Those skilled in the art will recognize that various techniques are available to adsorb or to covalently couple proteins, peptides, ligand analogues nucleotides and nucleic acids to latex particles. A solution of dye latex (0.1 ml, 2% solids, 412 nm; entry 10, Table 1) was added quickly while vortexing to a solution of anti-β hCG monoclonal antibody (0.2 ml, 6.6 mg/ml; Applied Biotech Inc., San Diego, Calif.) in 20 mM sodium borate/150 mM sodium chloride, pH 8.2. A solution of 0.1M potassium citrate, pH 3, (0.04 ml) was added quickly while vortexing to the antibody latex solution at room temperature and the pH of the resulting solution was 3.5. The solution incubated at room temperature for 5 minutes, then a solution of 2M potassium borate, pH 9.7 (0.025 ml) was added quickly while vortexing to bring the pH to about 8.5. This latex antibody conjugate was dialyzed (Spectra-por dialysis tubing, molecular weight cutoff of 300,000, Spectrum, Houston, Tex.) against 4 changes of 2 L each of 20 mM sodium borate/150 mM sodium chloride, pH 8.2 at 4° C. for 4 days. The dialyzed latex conjugate was then removed from the dialysis tubing and the solids concentration was calculated to be 0.4%. This conjugate can be used for immunoassays for hCG in serum. The latex has excitation and emission wavelengths of 650 nm and 780 nm, respectively.

A solution of polystyrene sulfate latex (0.036 ml, 8.4% solids, 1000 nm; Interfacial Dynamics Corp., Inc., Portland Oreg.) was added quickly, at room temperature, while vortexing to a solution consisting of anti-a hCG monoclonal antibody (0.12 ml, 10.3 mg/ml; Applied Biotech Inc. San Diego, Calif.) in 20 mM sodium borate/150 mM sodium chloride, pH 8.2 and 0.1M potassium citrate, pH 3, (0.6 ml). The solution incubated at room temperature for 5 minutes and was subjected to centrifugation in an Eppendorf centrifuge (2000×g for 5 min). The supernatant was removed, the pellet was resuspended in 0.1M potassium phosphate, pH 7, (1.5 ml) and the suspension was subjected to centrifugation as described above. This process was repeated 2 times more and in the final centrifugation, the pellet was resuspended with 0.1M potassium phosphate, pH 7 (0.3 ml) to make 1% solids. This antibody latex is used on a solid phase, such as a membrane, to capture the hCG-dye antibody latex conjugate complex in a reaction mixture in an immunoassay for hCG.

EXAMPLE 17

Immunoassay for hCG

The solid phase anti-a hCG latex solution (0.005 ml, 1% solids; example 16) can be applied to a 2 cm² piece of 0.45 micron nylon membrane (Millipore Corp., Boston, Mass.) which has been treated with a 2% solution of condensed milk to lower non-specific binding interactions. This membrane can be used as the solid phase onto which is captured the hCG dye latex conjugate complex. Thus, an hCG assay can be performed by addition of dye latex conjugate (0.025 ml, example 16) to 0.1 ml samples of serum suspected of containing hCG and also to 0.1 ml serum samples containing known amounts of hCG (10, 100, 300, 500 and 1000 mTU/ml,). The serum samples should be incubated about 10 minutes and then the samples are applied to the solid phase membrane containing the solid phase latex. The membrane should be placed over an absorbent so that the serum sample containing the dye latex conjugates flows through the solid phase latex spot. After the serum solution has passed through the membrane, serum (0.5 ml) not containing the dye latex conjugate is applied to the membrane to remove unbound dye latex conjugate. The latex spots on the membranes are then placed in a front surface fluorescence accessory in a fluorometer and the spot is excited at 650 nm and the fluorescence intensity of the spot on each membrane is measured at 780 nm. The fluorescence intensity as a function of the hCG concentrations of the known samples is plotted. The fluorescence intensities of the unknown hCG serum samples can be compared to the known hCG concentrations from the graph. The assay protocol of this Example may be performed using conjugates comprised of water soluble hybrid phthalocyanine derivatives and, for example, proteins, polypeptides, antibodies, nucleic acids and the like, instead of the dye latex conjugates.

EXAMPLE 18

Fluorometer for Measuring Near Infrared Emitting Dyes

The dye sample (2 ml sample volume in a 10 mm×10 mm quartz cuvette) was excited by a diode laser (Sun Laser SL-6; l=670+/−10 nm, 0.95 mW) which was filtered by a low-pass cutoff filter (Corion LS700, passes wavelengths less than 700 nm) . Fluorescence emission was detected at 90° to the incident diode laser beam. The emitted light was collected and focused on a silicon photodiode (Melles Griot, Cat. #13DS1009) by a condenser consisting of two aspheric lenses (Melles Griot, Cat #01 LAG 119). A high-pass cutoff filter (Schott Glass RG715) in front of the Silicon photodiode blocked scattered laser light at 670 nm but passed emitted light at wavelengths larger than 715 nm. The photocurrent from the silicon photodiode was amplified and displayed by a current amplifier in nanoamps ("nA"), (Melles Griot, Cat. # 13 AMP 003). In some instances, 12 nm band filters were placed in front of the silicon photodiode with center wavelengths at 730 nm, 790 nm, 850 nm, and 900 nm.

EXAMPLE 19

Synthesis of Silicon 2,3-Naphthalocyanine bis (diphenyl-vinylsilyl-oxide)

A suspension of silicon 2,3-naphthalocyanine dihydroxide (39 mg, 0.05 mmol) in dimethylformamide (0.5 ml) containing diphenylvinylchlorosilane (28 $\mu$L, 0.125 mmol) and imidazole (7 mg, 0.1 mmol) was stirred under argon at room temperature for 18 hours. The reaction mixture was evaporated and the residue purified on a silica column equilibrating with hexane and eluting the product with toluene as a long green band. The toluene fraction containing the product was evaporated to afford 5 mg green solid.

EXAMPLE 20

Synthesis of Silicon 2,3-Naphthalocyanine bis (triphenylsilyloxide)

A suspension of silicon 2,3-naphthalocyanine dihydroxide (39 mg, 0.05 mmol) in dimethylformamide (1 ml) containing triphenylchlorosilane (37 mg, 0.125 mmol) and imidazole (7 mg, 0.1 mmol) was stirred under argon at room temperature for 18 hours. The reaction mixture was evaporated and the residue purified on a silica column equilibrating with hexane and eluting the product with toluene as a green band. The toluene fraction containing the product was evaporated to afford 2.5 mg green solid.

EXAMPLE 21

Synthesis of Silicon 2,3-Naphthalocyanine bis (dimethylmaleimidoethoxysilyloxide)

A suspension of silicon 2,3-naphthalocyanine dihydroxide (39 mg, 0.05 mmol) in dimethylformamide (1 ml) containing dichlorodimethylsilane (13.5 $\mu$L, 0.11 mmol) and imidazole (14 mg, 0.2 mmol) was stirred under argon at room temperature for 18 hours. The reaction mixture was then treated with N-(2-hydroxyethyl)maleimide (35 mg, 0.25 mmol) and stirred for an additional 10 hours. The reaction mixture was evaporated and the residue purified on a silica column equilibrating with hexane, then toluene and eluting the product with toluene/10% isopropanol as a green band. The eluate containing the product was evaporated to afford 3.5 mg of green solid.

EXAMPLE 22

Synthesis of Silicon 2,3-Naphthalocyanine bis (dimethylsilyloxide-trans-stilbene)

A suspension of silicon 2,3-naphthalocyanine dihydroxide (39 mg, 0.05 mmol) in dimethylformamide (1 ml) containing dichlorodimethylsilane (13.5 $\mu$L, 0.11 mmol) and imidazole (14 mg, 0.2 mmol) was stirred under argon at room temperature for 2 hours. The reaction mixture was then treated with trans-4-hydroxystilbene (49 mg, 0.25 mmol) and stirred for an additional 5 hours. The reaction mixture was evaporated and the residue purified on a silica column equilibrating with hexane and eluting the product with toluene as a long green band. The toluene fraction containing the product was evaporated to afford 4 mg green solid.

EXAMPLE 23

Synthesis of Silicon 2,3-Naphthalocyanine bis (dimethylhexylvinyl-silyloxide)

A suspension of silicon 2,3-naphthalocyanine dihydroxide (39 mg, 0.05 mmol) in dimethylformamide (1 ml) containing 7-oct-1-enyldimethylchlorosilane (32 $\mu$L, 0.125 mmol) and imidazole (7 mg, 0.1 mmol) was stirred under argon at room temperature for 18 hours. The reaction mixture was evaporated and the residue purified on silica column equilibrating with hexane and eluting the product with toluene as a green band. The toluene fraction containing the product was evaporated and the residue treated with hexane to afford a dark green solid and light green supernatant. The mixture was centrifuged, the supernatant removed and the solid treated with more hexane and centrifuged. The supernatant was again removed and the solid dried under vacuum to yield 7.3 mg of product.

EXAMPLE 24

Synthesis of Silicon 2,3-Naphthalocyanine bis (tridecafluoro-1,1,-2,2-tetrahydrooctyl-1-dimethylsilyloxide)

A suspension of silicon 2,3-naphthalocyanine dihydroxide (39 mg, 0.05 mmol) in dimethylformamide (1 ml)

containing (tridecafluoro-1,1,2,2-tetrahydrooctyl)-1-dimethylchlorosilane (37 μL, 0.1 mmol) and imidazole (7 mg, 0.1 mmol) was stirred under argon at room temperature for 2 hours. The reaction mixture was evaporated and the residue purified on a silica column equilibrating with hexane and eluting with hexane/20% toluene followed by hexane/40% toluene to afford the product as a green band. The product eluate was evaporated and the residue treated with hexane to afford a green solid. The mixture was centrifuged, the supernatant removed and the solid treated with more hexane and recentrifuged. The supernatant was again removed and the green solid dried under vacuum to yield 7.5 mg of product.

EXAMPLE 25

Synthesis of Silicon 2,3-Naphthalocyanine bis (dimethyl-retinol)

A suspension of silicon 2,3-naphthalocyanine dihydroxide (39 mg, 0.05 mmol) in dimethylformamide (1 ml) containing dichlorodimethylsilane (13.5 μL, 0.11 mmol) and imidazole (14 mg, 0.2 mmol) was stirred under argon at room temperature. After 20 minutes, the reaction mixture was treated with all-trans-retinol (72 mg, 0.25 mmol) and stirred for an additional 1 hour. The reaction mixture was evaporated and the residue purified on a silica column equilibrating with hexane and eluting the product with toluene as a long green band. The toluene fraction containing the product was evaporated and the residue treated with hexane to yield a dark green solid and light green supernatant. The mixture was centrifuged, the hexane removed and the solid dried under vacuum to yield 10 mg of final product.

EXAMPLE 26

Synthesis of Silicon (IV) 5,9,14,18,23,27,32,36-octaethoxy-2,3-naphthalocyanine dichloride (abbreviated as: Silicon octaethoxy-2,3-naphthalocyanine dichloride))

4,9-Diethoxy-1,3-diiminobenz[f]isoindoline (0.6 g) was added under argon to freshly distilled quinoline (12 ml). After stirring for 10 minutes, silicon tetrachloride (4.0 ml) was added and the reaction mixture was heated at 190° C. for 1 hour. The reaction mixture was cooled to room temperature, and water (120 ml) was added slowly to hydrolyze the unreacted silicon tetrachloride. The blue-black precipitate was filtered off and washed sequentially with methanol (5 ml) and acetone (5 ml).

UV-vis (methylene chloride) ($\lambda_{max}$nm)): 768, 869.

EXAMPLE 27

Synthesis of Silicon (IV) 5,9,14,18,23,27,32,36-octaethoxy-2,3-naphthalocyanine dihydroxide (abbreviated as: Silicon octaethoxy-2,3-naphthalocyanine dihydroxide)

A suspension of silicon octaethoxy-2,3-naphthalene dichloride (1.96 g) in pyridine (15 ml) containing water (15 ml) was refluxed for 18 hours. The suspension was cooled, the black precipitate filtered and washed with water (10 ml). The precipitate was dried under vacuum and weighed (1.37 g, purple powder).

UV-vis (methylene chloride) ($\lambda_{max}$(nm)): 766, 867.

EXAMPLE 28

Synthesis of Silicon (IV) 5,9,14,18,27,32,36-octaethoxy-2,3-naphthalocyanine bis (7-oct-1-enyl dimethyl silyloxide) (abbreviated as: Silicon octaethoxy-2,3-naphthalocyanine bis (dimethylhexylvinylsilyloxide))

A suspension of silicon IV octaethoxy-2,3-naphthalocyanine dihydroxide (1.0 g) in dimethylformamide (20 ml) containing 7-oct-1-enyldimethylchlorosilane (0.6 ml) and imidazole (140 mg) was stirred under argon at room temperature for 24 hours. The reaction mixture was evaporated with a rotary evaporator, chromatographed on a silica gel(70–230 mesh, 60 Å,) column (2×50 cm)equilibrated in hexane. The product was eluted sequentially with hexane and hexane-toluene(1:1)), vacuum dried, and weighed (46 mg).

UV-vis (tetrahydrofuran) ($\lambda_{max}$(nm), $\epsilon(M^{-1}cm^{-1})$): 855, 370000.

Infrared Spectrum(KBr): 3074, 2958, 2924, 2854, 1589, 1417, 1373, 1348, 1262, 1238, 1194, 1161, 1111, 1044, 1025, 933, 909, 844, 799, 760 cm$^{-1}$.

$^1$H-NMR (500 MHz, CDCl$_3$): δ 9.0 (m, 2,5-Nc), 7.9 (m, 3,4-Nc), 5.3 (m, —CH$_2$), 4.6 (m, vinyl —CH$_2$), 3.5 (m, vinyl CH), 1.8 (m, —CH$_3$), 1.3 (m, δ —CH$_2$), 0.5 (m, δ —CH$_2$), 0.1 (m, γ —CH$_2$), -0.8 (m, α —CH$_2$), -1.7 (m, α —CH$_2$), -2,3 (s, —CH$_3$).

EXAMPLE 29

Synthesis of Silicon Phthalocyanine bis (dimethylmaleimidofluorescein)

Fluorescein ATP (0.5 mg, 1.05 μmol) was treated with a solution of 0.12M potassium carbonate in 80% methanol (52 μL). After 5 minutes, the hydrolysis solution was quenched by the addition of 0.5M potassium phosphate/0.1M potassium borate, pH 7.0 in 1N HCl (10 μL). The quenched hydrolysis solution was evaporated to dryness, redissolved in dimethylformamide (100 μL) and the resulting solution added to silicon phthalocyanine bis (dimethylmaleimidosilyloxide) in a 1.0 ml serum vial. The reaction mixture was then stirred at room temperature for 1 hour. The crude product was then chromatographed on two 3"×3" silica plates using toluene/20% dimethylformamide. After elution, the plates were dried under vacuum and rechromatographed for a better separation. The product band was scraped off, and treated with dimethylformamide (5 ml), vortexed 30 seconds and filtered from the silica. The filtrates were evaporated to give 0.55 mg of greenish fluorescent solid.

EXAMPLE 30

Synthesis of Tin(IV)5,9,14,18,23,27,32,36-octabutoxy-2,3-naphthalocyanine bis (triethylsilyloxide))

A mixture of triethylsilanol (77 μL), sodium (3.5 mg), and xylenes (5 ml) was refluxed under argon for 1 hour. A solution of Tin(IV) octabutoxy-2,3-naphthalocyanine dichloride (74 mg) in xylenes (5 ml) was added to the solution formed and the mixture was refluxed for 20 minutes. The resultant was washed twice with water (25 ml each time), dried (MgSO$_4$), and evaporated to a dark red solid with a rotary evaporator. This solid was chromatographed on a silica gel(70–230 mesh, 60 Å,) column (2×50 cm) equilibrated in hexane and eluted sequentially with toluene and toluene-10% isopropanol. The product was vacuum dried, and weighed (17 mg).

UV-vis(tetrahydrofuran) ($\lambda_{max}$(nm), $\epsilon(M^{-1}cm^{-1})$): 900, 174000.

EXAMPLE 31

Synthesis of Tin(IV) 2,3-naphthalocyanine bis (triethylsilyloxide)

A mixture of triethylsilanol (77 μL), sodium (3.5 mg), and xylenes (8 ml) was refluxed under argon for 1 hour. Tin(IV)

2,3-naphthalocyanine dichloride (45 mg) was added to the solution formed, and the mixture was refluxed for 5 days. The suspension was filtered, and the solid was washed sequentially with xylenes and water, vacuum dried, and weighed (41 mg). The solid was chromatographed on a silica gel (70–230 mesh, 60 Å,) column (2×50 cm) equilibrated with methylene chloride and eluted sequentially with methylene chloride—20% tetrahydrofuran, methylene chloride—50% tetrahydrofuran and finally tetrahydrofuran. The product was triturated with hexane (2 ml), vacuum dried, and weighed (26 mg).

UV-vis(tetrahydrofuran) ($\lambda_{max}$(nm), $\epsilon(M^{-1}cm^{-1})$): 700; 746; 786, 253000.

Fluorescence (tetrahydrofuran) ($\lambda_{max}$(nm)): 820.

EXAMPLE 32

Synthesis of Tin(IV)2,3-naphthalocyanine bis(7-oct-1-enyldimethylsilyloxide) (abbreviated as: Tin(IV)2,3-naphthalocyanine bis (dimethylhexylvinylsilyloxide))

A mixture of 7-oct-1-enyldimethylsilanol (186 mg), sodium (7 mg), and xylenes (10 ml) was refluxed under argon for 4 hours. Tin(IV)2,3-naphthalocyanine dichloride (90 mg) was added to the solution formed and the mixture was refluxed for 4 days. The suspension was filtered and the solid was washed sequentially with xylenes (5 ml) and water (5 ml). The organic layer of the filtrate was separated, dried ($MgSO_4$), and evaporated with a rotary evaporator. The residue was triturated twice with hexane (2 ml each time) to afford a bright green solid which was vacuum dried and weighed (8.5 mg).

UV-vis (tetrahydrofuran) ($\lambda_{max}$(nm), $\epsilon(M^{-1}cm^{-1})$): 670, 7200; 732, 69900; 786, 84900.

EXAMPLE 33

Synthesis of Tin (IV)5,9,14,18,23,27,32,36-octabutoxy-2,3-naphthalocyanine dichloride Tin tetrachloride (234 µL) was added to a mixture of octabutoxy-2,3-naphthalocyanine (310 mg) in dry dimethylformamide (15 ml) under an argon atmosphere and the mixture refluxed with stirring for 6 hours. The resultant was allowed to cool, the suspension was filtered, and the dark red solid was washed sequentially with dimethylformamide (5 ml) and water (5 ml), vacuum dried and weighed (288 mg).

EXAMPLE 34

Synthesis of Tin(IV)5,9,14,18,23,27,32,36-octabutoxy-2,3-naphthalocyanine bis(7-oct-1-enyldimethylsilyloxide (abbreviated as: Tin(IV) Octabutoxy-2,3-naphthalocyanine bis (dimethylhexylvinylsilyloxide))

A mixture of 7-oct-1-enyldimethylsilanol (186 mg), sodium (7 mg), and xylenes (10 ml) was refluxed under argon for 5 hours. Tin(IV) octabutoxy-2,3-naphthalocyanine dichloride (37 mg) was added to the solution formed, and the mixture was refluxed for 2 days. The resultant was washed with water (10 ml), dried ($MgSO_4$), and evaporated to a dark red solid with a rotary evaporator. This solid was chromatographed on a silica gel (70–230 mesh, 60 Å,) column (2×50 cm) equilibrated in hexane and eluted sequentially with toluene and toluene—10% isopropanol. The product was vacuum dried, and weighed (17 mg).

UV-vis (tetrahydrofuran) ($\lambda_{max}$(nm), $\epsilon(M^{-1}cm^{-1})$): 785; 893, 227000.

Fluorescence(tetrahydrofuran) ($\lambda_{max}$(nm)): 789

EXAMPLE 35

Synthesis of 7-oct-1-enyldimethylsilanol

A solution of 7-oct-1-enyldimethylchlorosilane (2.56 ml) in ether (2 ml) was added dropwise over 1 hour to a stirring mixture of triethylamine (1.5 ml), water (0.18 ml) and ether (15 ml) in an ice/water bath. The resultant was stirred a further 1 hour in the ice/water bath and filtered washing the filtered solid with ether (10 ml). The filtrate was evaporated with a rotary evaporator and the residue partitioned between hexane (30 ml) and water (30 ml). The organic layer was separated, dried ($MgSO_4$) and filtered through silica gel (70–230 mesh, 60 Å), washing with hexane (100 ml). The filtrate was evaporated with a rotary evaporator to afford a colorless oil which was vacuum dried and weighed (1.06 g).

EXAMPLE 36

Synthesis of 2,3,20,21-tetrabromo)-9,14,27,32-tetrabutoxy-2,3-naphthalocyanine 1,4-dibutoxynaphthalene-2,3-dicarbonitrile (161 mg) and 2,3-dibromo-6,7-dicyanonaphthalene (168 mg) were added to a refluxing solution of lithium metal (35 mg) in 1-butanol (2 ml) under an argon atmosphere. The reaction solution was maintained at reflux for 2 hours, cooled, and stirred into glacial acetic acid (10 ml). After 30 minutes, the solvent was evaporated with a rotary evaporator and the residue dissolved in methylene chloride (10 ml). The solution was washed twice with 1N hydrochloric acid (10 ml each time), followed by water (10 ml), dried ($MgSO_4$) and evaporated with a rotary evaporator. The residue was chromatographed on a silica gel (70–230 mesh, 60 Å,) column (2×50 cm) equilibrated in hexane and eluted sequentially with hexane—10% toluene, hexane—20% toluene, hexane—30% toluene, hexane—40% toluene and finally hexane—50% toluene. The solid product was triturated with hexane (2 ml), vacuum dried, and weighed (8 mg).

UV-vis(tetrahydrofuran) ($\lambda_{max}$(nm)): 743, 839.

Fluorescence(tetrahydrofuran) ($\lambda_{max}$(nm)): 789.

EXAMPLE 37

Synthesis of $2^1,2^6,7^1,7^6/12^1,12^6$-tetrabutoxydinaphtho[b,g/l]-7,12/17-octafluorodibenzo[g,l/q ]-5,10,15,20-tetraazoporphyrin (abbreviated as: Di(1,6-dibutoxy-2,3-naphthalocyanine) di(tetrafluorophthalocyanine)

1,4-Dibutoxynaphthalene-2,3-dicarbonitrile (161 mg) and tetrafluorophthalonitrile (100 mg) were added to a refluxing solution of lithium metal (35 mg) in 1-butanol (2 ml) under an argon atmosphere. The reaction solution was maintained at reflux for 1 hour, cooled, and stirred into glacial acetic acid (10 ml). After 30 minutes the solvent was evaporated with a rotary evaporator and the residue dissolved in methylene chloride (10 ml). The solution was washed twice with 1N hydrochloric acid (10 ml each time), followed by water (10 ml), dried ($MgSO_4$) and evaporated with a rotary evaporator. The residue was chromatographed twice on a silica gel (70–230 mesh, 60 Å, 2×50 cm),column equilibrated in hexane and eluted sequentially with hexane—10% toluene, hexane—20% toluene, hexane—30% toluene, and finally hexane—40 % toluene. The product was vacuum dried and weighed (10 mg).

UV-vis (tetrahydrofuran) ($\lambda_{max}$(nm), $\epsilon(M^{-1}cm^{-1})$): 679, 25800; 752, 88200; 789, 76500.

Fluorescence (tetrahydrofuran) ($\lambda_{max}$(nm)) 815.

EXAMPLE 38

Synthesis of $2^1,2^6,12^1,12^6$-tetraphenylydinaphthor[b,l]-7,17-octafluorodibenzo[g,q]-5,10,15,20-tetraazoporphyrin (abbreviated as: Di(1,6-diphenyl-2,3-naphthalocyanine) di(tetrafluorophthalocyanine))

1,4-diphenylnaphthalene-2,3-dicarbonitrile (165 mg) and tetrafluorophthalonitrile (100 mg) were added to a refluxing solution of lithium metal (35 mg) in 1-butanol (2 ml) under an argon atmosphere. The reaction solution was maintained at reflux for 1.5 hours, cooled, and stirred into glacial acetic acid (10 ml). After 30 minutes, the solvent was evaporated with a rotary evaporator and the residue dissolved in methylene chloride (10 ml). The solution was washed twice with 1N hydrochloric acid (10 ml each time), followed by water (10 ml), dried (MgSO$_4$), and evaporated with a rotary evaporator. The residue was chromatographed on a silica gel (70–230 mesh, 60 Å,) column (2×50 cm) equilibrated in hexane and eluted sequentially with hexane—10% toluene, hexane—200 toluene, hexane—30% toluene, hexane—40% toluene and finally hexane—50% toluene. The bright green product was vacuum dried and weighed (7 mg).

UV-vis (tetrahydrofuran) ($\lambda_{max}$(nm), $\epsilon$(M$^{-1}$cm$^{-1}$)): 747, 86800.

Fluorescence(tetrahydrofuran) ($\lambda_{max}$(nm)): 760.

EXAMPLE 39

Synthesis of Dibutoxy-1,3-diiminobenz[f]lisoindoline

Anhydrous ammonia was slowly bubbled through a stirred mixture of 1,4-dibutoxynaphthalene-2,3-dicarbonitrile (1.61 g), 25% sodium methoxide in methanol (1.14 ml), and dry 1-butanol (10 ml) for 30 minutes. With continued ammonia introduction, the mixture was refluxed for 30 minutes. After the resultant had cooled, the solvent was removed under vacuum with a rotary evaporator. The residue was chromatographed on a silica gel (70–230 mesh, 60 Å,) column (2×50 cm), equilibrated in hexane and eluted sequentially with toluene, toluene—1% isopropanol, toluene—2% isopropanol, toluene—5% isopropanol, toluene—10% isopropanol and finally toluene—20% isopropanol. The yellow product was treated with ether (10 ml), collected by filtration, washed with ether (10 ml), vacuum dried and weighed (517 mg).

$^1$H-NMR (500 MHZ, CDCl$_3$) δ 8.22 (m, 5,8 —H), 7.65 (m, 6,7 —H), 4.23 (m, γ —CH$_2$), 1.97 (m, β —CH$_2$), 1.61 (m, α —CH$_2$), 1.04 (t, —CH$_3$).

EXAMPLE 40

Synthesis of 4,9-diethoxy-1,3-diiminobenz[f]isoindoline

Anhydrous ammonia was slowly bubbled through a stirred mixture of 1,4-diethoxynaphthalene-2,3-dicarbonitrile (1.33 g), 25% sodium methoxide in methanol (1.14 ml), and dry ethanol (10 ml) for 20 minutes. With continued ammonia introduction, the mixture was refluxed for 2 hours. After the resultant had cooled, the solvent was removed under vacuum with a rotary evaporator. The residue was treated with methylene chloride (10 ml) and the product was collected by filtration, washed sequentially with water (5 ml) and methylene chloride (5 ml), vacuum dried and weighed (766 mg).

EXAMPLE 41

Synthesis of $[2^1,2^6,12^1,12^6$-tetraphenyldinaphtho[b,1/]-7,17-dibenzo[g,q]-5,10,15,20-tetraazoporphyrinato]silicon dihydroxide (abbreviated as: Silicon [di(1,6-diphenyl-2,3-naphthalocyanine)] diphthalocyanine dihydroxide)

Silicon tetrachloride (231 μL) was added to a mixture of diphenyl-1,3-diiminobenz[f]isoindoline (470 mg) and 1,3-diiminoisoindoline (97 mg) in freshly distilled quinoline (5 ml) under an argon atmosphere and the mixture heated with stirring at 200° C. for 40 minutes. The resultant was allowed to cool to 160° C., treated with water (5 ml) and refluxed for 5 minutes. The mixture was cooled, treated with ether (30 ml) and filtered washing the solid sequentially with ether (10 ml) and water (10 ml). The organic layer of the filtrate (which was dark green) was separated from the aqueous layer, washed with water (15 ml), dried (MgSO$_4$) and evaporated with a rotary evaporator. The residue was chromatographed three times on a silica gel (70–230 mesh, 60 Å,) column (2×50 cm) equilibrated in hexane and eluted sequentially with hexane, hexane—10% methylene chloride, hexane—20% methylene chloride, and finally hexane—50% methylene chloride. The product was vacuum dried and weighed (55.5 mg).

UV-vis (tetrahydrofuran) ($\lambda_{max}$(nm), $\epsilon$(M$^{-1}$cm$^{-1}$)): 640; 680; 714, 67900; 742.

Fluorescence (tetrahydrofuran) ($\lambda_{max}$(nm)): 750.

EXAMPLE 42

Synthesis of $[2^1,2^6,7^6,/12^1,12^6$, -tetraethoxydinaphtho[b,g/l]-7,12/17-dibenzo[g,l/q]-5,10,15,20-tetraazoporphyrinato]silicon dihydroxide] (abbreviated as: Silicon [di(1,6-diethoxy-2,3-naphthalocyanine)]diphthalocyanine dihydroxide)

Silicon tetrachloride (137 μL) was added to a mixture of 4,9-diethoxy-1,3-diiminobenz[f]isoindoline (227 mg) and 1,3-diiminoisoindoline (58 mg) in freshly distilled quinoline (3 ml) under an argon atmosphere and the mixture heated with stirring at 200° C. for two hours. The resultant was allowed to cool 160° C., treated with water (3 ml) and refluxed for 5 minutes. The mixture was cooled, treated with ether (10 ml), and the dark blue solid product filtered off, washing the solid sequentially with ether (10 ml) and water (10 ml), vacuum dried and weighed (175 mg).

UV-vis (tetrahydrofuran) ($\lambda_{max}$(nm)): 600, 632, 666, 700, 724, 788.

EXAMPLE 43

Synthesis of $[2^1,2^6,7^1,7^{6\ b\ /121},12^6$, -tetraethoxydinaphtho[b,g/l]-7,12/17-dibenzo[g,l/q]-5,10,15,20-tetraazoporphyrinato]silicon bis(7-oct-1-enyldimethylsilyloxide (abbreviated as: Silicon [di (1,6-diethoxy-2,3-naphthalocyanine)] diphthalocyanine bis (dimethylhexylvinylsilyloxide))

A mixture of silicon [di(1,6-diethoxy-2,3-naphthalocyanine)] diphthalocyanine dihydroxide (85 mg), 7-oct-1-enyldimethylchlorosilane (256 μL), imidazole (68 mg), and dimethylformamide (2 ml) was stirred at room temperature for 24 hours. The resultant was concentrated under vacuum with a rotary evaporator. The residue was chromatographed on a silica gel (70–230 mesh, 60 Å,)

column (2×50 cm) equilibrated in hexane and eluted sequentially with toluene and toluene—1% isopropanol. The product was vacuum dried and weighed (32 mg).

UV-vis (tetrahydrofuran) ($\lambda_{max}$(nm)): 601, 633, 667, 702, 731, 822, 904.

EXAMPLE 44

Synthesis of [$2^1,2^6,12^1,12^6$-tetraphenyldinaphtho [b,l]-7,17-dibenzo [g,q]-5,10,15,20-tetraazoporphyrinato] silicon bis(7-oct-1-enyldimethylsilyloxide) (abbreviated as: Silicon [di(1,6-diphenyl-2,3-naphthalocyanine)]) diphthalocyanine bis(dimethylhexylvinylsilyloxide) (FIG. 9).

A mixture of silicon [di(1,6-diphenyl-2,3-naphthalocyanine)] diphthalocyanine dihydroxide (30 mg), 7-oct-1-enyldimethylchlorosilane (115 µL), imidazole (30 mg) and dimethylformamide (650 µL) was stirred at room temperature for 30 minutes. The resultant was concentrated under vacuum on the rotary evaporator. The residue was chromatographed on a silica gel (70–230 mesh, 60 Å,) column (2×50 cm) equilibrated in hexane and eluted sequentially with hexane and toluene. The product was vacuum dried and weighed (38 mg).

$^1$H-NMR (500 MHZ, CDCl$_3$) δ 8.31, 8.25 (m, 2,5-Nc, 10,13-Nc), 7.94 (m, Ar-Nc), 7.95, 7.74 (3,4-Nc, 11,12-Pc), 0.68 (m, ε —CH$_2$), 0.21 (m, δ —CH$_2$), -0.11 (m, γ —CH$_2$), -1.22 (m, β—CH$_2$), -2.14 (m, α—CH$_2$), -2.76 (s, —CH$_3$).

UV-vis (tetrahydrofuran) ($\lambda_{max}$(nm), ε(M$^{-1}$ cm$^{-1}$)): 644; 684; 718, 81100; 748.

Fluorescence(tetrahydrofuran) ($\lambda_{max}$(nm)): 754.

EXAMPLE 45

Synthesis of Tetrafluoro-1,3-diiminobenz[f] isoindoline

Anhydrous ammonia was slowly bubbled through a stirred mixture of tetrafluorophthalonitrile (2.0 g), 25% sodium methoxide in methanol (2,3 ml), and dry 1-butanol (10 ml) for 20 minutes. With continued ammonia introduction, the mixture was refluxed for 1 hour. After the resultant had cooled, the solvent was removed under vacuum with a rotary evaporator. The residue was treated with ether (50 ml) and the product was collected by filtration, washed sequentially with water (10 ml), and ether (10 ml), vacuum dried and weighed (0.45 g).

EXAMPLE 46

Synthesis of 4,7-diphenyl-1,3-diiminobenz[f] isoindoline

Anhydrous ammonia was slowly bubbled through a stirred mixture of 1,4-diphenylnaphthalene-2,3-dicarbonitrile (4.3 g), 25% sodium methoxide in methanol (3.0 ml), and dry 1-butanol (25 ml) for 30 minutes. With continued ammonia introduction, the mixture was refluxed for 1.5 hours. After the resultant had cooled, the solvent was removed under vacuum with a rotary evaporator. The residue was treated with methylene chloride (50 ml) and the product was collected by filtration, washed sequentially with water (10 ml) and methylene chloride (10 ml), vacuum dried and weighed (3.68 g).

EXAMPLE 47

Synthesis of [$2^1,2^6,12^1,12^6$-tetraphenyldinaphtho[b,l]-7,17-octafluorodibenzo[g,q]-5,10,15,20-tetraazoporphyrinato]silicon dihydroxide (abbreviated as: Silicon[di(1,6-diphenyl-2 3-naphthalocyanine)]di(tetrafluoro phthalocyanine) dihydroxide)

Silicon tetrachloride (86 µL) was added to a mixture of diphenyl-1,3-diiminobenz[f]isoindoline (174 mg) and tetrafluoro-1,3-diiminoisoindoline (54 mg) in freshly distilled quinoline (1 ml) under an argon atmosphere and the mixture heated with stirring at 200° C. for 1 hour. The resultant was allowed to cool to 160° C., treated with water (1 ml) and refluxed for 5 minutes. The mixture was cooled, treated with ether (10 ml) and filtered washing the solid sequentially with water (2 ml) and ether (5 ml). The organic layer of the filtrate was separated, washed with water (5 ml), dried (MgSO$_4$) and evaporated with a rotary evaporator. The residue was chromatographed on a silica gel (70–230 mesh, 60 Å, 2×50 cm) column equilibrated in methylene chloride and eluted with methylene chloride. The product was vacuum dried and weighed (18 mg).

UV-vis (tetrahydrofuran) ($\lambda_{max}$(nm)): 727, 759, 809, 835.

Fluorescence (tetrahydrofuran) ($\lambda_{max}$(nm)): 685, 760, 840.

EXAMPLE 48

Synthesis of [$2^1,2^6,12^1,12^6$-tetraphenyldinaphtho[b,l]$17^1,7^6$-diethoxynaphtho[g]-17-benzo[q]-5,10,15,20-tetraazoporphyrinato]silicon dihydroxide (abbreviated as: Silicon[di(1,6-diphenyl-2,3-naphthalocyanine)]1,6-diethoxyphthalocyanine) phthalocyanine dihydroxide)

Silicon tetrachloride (172 µL) was added to a mixture of diphenyl-1,3-diiminobenz[f]isoindoline (347 mg), diethoxy-1,3-diiminobenz[f]isoindoline (71 mg) and 1,3-diiminoisoindoline (36 mg) in freshly distilled quinoline (2 ml) under an argon atmosphere and the mixture heated with stirring at 200° C. for 1 hour. The resultant was allowed to cool to 160° C. , treated with water (2 ml) and refluxed for 5 minutes. The mixture was cooled, treated with ether (10 ml) and filtered washing the solid sequentially with water (5 ml) and ether (5 ml). The organic layer of the filtrate was separated, washed with water (10 ml), dried (MgSO$_4$) and evaporated with a rotary evaporator. The residue was chromatographed on a silica gel (70–230 mesh, 60 Å, 2×50 cm) column equilibrated in methylene chloride and eluted with methylene chloride. The product was vacuum dried and weighed (6 mg).

UV-vis (methylene chloride) ($\alpha_{max}$(nm) ): 649, 693, 724, 758, 827.

Fluorescence (tetrahydrofuran) ($\alpha_{max}$(nm)): 750.

EXAMPLE 49

Synthesis of [$2^1,2^6,12^1,12^6$-tetralphenyldinaphtho[b,l]-7-tetrafluoronaphtho[-17-benzo[q]-5,10,15,20-tetraazoporphyrinato]silicon dihydroxide (abbreviated as: Silicon[di(1,6-diphenyl-2,3-naphthalocyanine)](tetrafluoro phthalocyanine) phthalocyanine dihydroxide)

Silicon tetrachloride (172 µL) was added to a mixture of diphenyl-1,3-diiminobenz[f]isoindoline (347 mg), tetrafluoro-1,3-diiminobenz[f]isoindoline (54 mg) and 1,3-diiminoisoindoline (36 mg) in freshly distilled quinoline (2 ml) under an argon atmosphere and the mixture heated with stirring at 200° C. for 1 hour. The resultant was allowed to cool to 160° C., treated with water (2 ml) and refluxed for 5 minutes. The mixture was cooled, treated with ether (10 ml) and filtered washing the solid sequentially with water (5 ml) and ether (5 ml). The organic layer of the filtrate was separated, washed with water (10 ml), dried (MgSO$_4$) and evaporated with a rotary evaporator. The residue was chromatographed on a silica gel (70–230 mesh, 60 Å, 2×50 cm)

column equilibrated in methylene chloride and eluted with methylene chloride. The product was vacuum dried and weighed (21 mg).

UV-vis (tetrahydrofuran) ($\lambda_{max}$(nm)): 646, 689, 720, 753, 790.

Fluorescence (tetrahydrofuran) ($\lambda_{max}$(nm)): 760.

EXAMPLE 50

Synthesis of [$2^1,2^6,12^1,12^6$-tetraphenyldinaphtho[b,1]7-tetrafluoronaphthro[g]-17-benzo[q]-5,10,15,20-tetraazoporphyrinato]silicon bis (7-oct-1-enyldimethylsilyloxide(abbreviated as: Silicon [di (1,6-diphenyl-2,3-naphthalocyanine)](tetrafluoro phthalocyanine) phthalocyanine bis (dimethylhexylvinylsilyloxide))

A mixture of silicon [di(1,6-diphenyl-2,3-naphthalocyanine)](tetrafluoro phthalocyanine) phthalocyanine dihydroxide (10.5 mg), 7-oct-1-enyl dimethylchlorosilane (38 µL), imidazole (10 mg) and dimethylformamide (200 µL) was stirred at room temperature for 30 minutes. The resultant was concentrated under vacuum on the rotary evaporator. The residue was chromatographed on a silica gel (70–230 mesh, 60 Å, 2×50 cm) column equilibrated in hexane and eluted with toluene, The product was vacuum dried and weighed (4 mg).

UV-vis(tetrahydrofuran) ($\lambda_{max}$(nm)): 732, 757, 794, 816.

Fluorescence(tetrahydrofuran) ($\lambda_{max}$(nm)): 763, 830.

EXAMPLE 51

Synthesis of [$2^1,2^6,12^1,12^6$-tetraphenyldinaphtho[b,1]-7-tetrafluoronaphtho[g]-17-benzo[q]-5,10,15,20-tetraazoporphyrinato]silicon bis(dimethylpentafluoro phenylsilyloxide) (abbreviated as: Silicon [di(1,6-diphenyl-2,3-naphthalocyanine)](tetrafluoro phthalocyanine) phthalocyanine bis (dimethylpentafluorophenylsilyloxide))

A mixture of silicon [di(1,6-diphenyl-2,3-naphthalocyanine)](tetrafluoro phthalocyanine) phthalocyanine dihydroxide (10.5 mg), chlorodimethylpentafluorophenylsilane (28 µL), imidazole (10 mg) and dimethylformamide (200 µL) was stirred at room temperature for 30 minutes. The resultant was concentrated under vacuum on the rotary evaporator. The residue was chromatographed on a silica gel (70–230 mesh, 60 Å, 2×50 cm) column equilibrated in hexane and eluted with hexane—500 toluene to afford two product fractions A and B which were vacuum dried and weighed (2.8 mg and 5.5 mg, respectively).

A. UV-vis(tetrahydrofuran) ($\lambda_{max}$(nm)): 650, 726, 762, 796, 824.

Fluorescence(tetrahydrofuran) ($\lambda_{max}$(nm)): 770.

B. UV-vis (tetrahydrofuran) ($\lambda_{max}$(nm):651, 726, 763, 796, 824.

Fluorescence (tetrahydrofuran) ($\lambda_{max}$(nm)) 770.

EXAMPLE 52

Synthesis of [$2^1,2^6,12^1,12^6$-tetraphenyldinaphtho[b,1]-7,17-dibenzo[g,q]-5,10,15,20-tetraazoporphyrinato]silicon bis (dimethylpentafluorophenylsilyloxide) (abbreviated as: Silicon [di(1,6-diphenyl-2,3-naphthalocyanine)] diphthalocyanine bis (dimethylpentafluorophenylsilyloxide))

A mixture of silicon [di(1,6-diphenyl-2,3-naphthalocyanine)]diphthalocyanine dihydroxide (20 mg), chlorodimethylpentafluorophenylsilane (58 µL), imidazole (20 mg) and dimethylformamide (450 µL) was stirred at room temperature for 1 hour. The resultant was concentrated under vacuum on the rotary evaporator. The residue was treated with hexane (5 ml) and the green solid product collected by filtration, washed with hexane (2 ml), vacuum dried and weighed (26 mg) .

UV-vis (tetrahydrofuran) ($\lambda_{max}$(nm):648, 691, 724, 759.

Fluorescence (tetrahydrof uran) ($\lambda_{max}$(nm)):768.

EXAMPLE 53

Synthesis of [$2^1,2^6,12^1,12^6$-tetraphenyldinaphtho[b,1]-7,17-dibenzo[g,q]-5,10,15,20-tetraaza (21H), (23H), porphyrin (abbreviated as: di(1,6-diphenyl-2,3-napthalocyanine)di(2,3-tert-butylphthalocyanine)

A mixture of 1,4-diphenylnaphthalene dicarbonitrile (495 mg), 4-tert-butylphthalonitrile (92 mg), and lithium butoxide (4.0 ml) was refluxed in an oil bath for 1.5 hours and cooled. Cold glacial acetic acid (20 ml) was added to the suspension formed and vacuum dried. The green residue was resuspended in dichloromethane and the solution centrifuged at 3000 rpm for 15 minutes. The supernatant was washed with 1N HCL (2×20 ml) followed by water (1×10 ml). The organic layer was dried under vacuum. The crude product was chromatographed on a silica gel (70–230 mesh, 60 Å, 2×50 cm) column equilibrated in hexane. The product was eluted sequentially with hexane and toluene, vacuum dried and weighed (4.2 mg).

UV-vis (tetrahydrofuran) ($\lambda_{max}$(nm), $\epsilon(M^{-1}\ cm^{-1})$): 668, 43297; 688, 86914; 726, 92715; 758, 64329.

Fluorescence (tetrahydrofuran) ($\lambda_{max}$(nm)): 732.

EXAMPLE 54

Synthesis of 5-tert-butyl-1,3-diiminoisolindoline

Anhydrous ammonia was slowly bubbled through a stirred mixture of 4-tert-butylphthalonitrile (1.8 g), 25% sodium methoxide in methanol (2,3 ml), and dry 1-pentanol (20 ml) for 30 minutes. With continued ammonia introduction, the mixture was refluxed for 1.5 hours. After the resultant had cooled, the solvent was removed with a rotary evaporator. The residue was treated with methylene chloride (20 ml) and the product was collected by filtration, washed sequentially with methylene chloride (20 ml), ether (10 ml), vacuum dried and weighed (0.4 g).

EXAMPLE 55

Synthesis of 6,7-dibromo-1,3-diiminobenz[f] isoindoline

Anhydrous ammonia was slowly bubbled through a stirred mixture of 6,7-dibromonaphthalene-2,3-dicarbonitrile (0.5 g), 25% sodium methoxide in methanol (0.3 ml), and dry 1-pentanol (10 ml) for 50 minutes. With continued ammonia introduction, the mixture was refluxed for 2.5 hours. After the resultant had cooled, the orange-yellow solid was collected by filtration and washed with ether (20 ml), vacuum dried and weighed (0.6 g).

EXAMPLE 56

Synthesis of Silicon [di(1,6-diphenyl-2,3-naphthalocyanine) di-tert-butylphthalocyanine] dihydroxide Silicon tetrachloride (57 µL) was added to a mixture of diphenyl-1,3-diiminobenz[f]isoindoline (172 mg) and 5-tert-butyl-1,3-diiminoisoindoline (50 mg) in freshly distilled quinoline (1 ml) under an argon atmosphere and the mixture heated with stirring at 210° C. for 1 hour. The resultant was allowed to cool, treated with water (2 ml) and refluxed for 5 minutes. The mixture was cooled, treated with ether (10 ml) and filtered washing the solid with ether (30 ml). The organic layer of the filtrate was separated, washed twice with water (20 ml each time), dried ($Na_2SO_4$) and the ether evaporated with a rotary evaporator. The residue was chromatographed on a silica gel (70–230 mesh, 60 Å, 2×50 cm), column equilibrated with hexane. The product was eluted with methylene chloride, vacuum dried and weighed (11 mg, green solid).

UV-vis (methylene chloride) ($\lambda_{max}$(nm) ): 656, 670, 694, 730, 758.

Fluorescence (methylene chloride) ($\lambda_{max}$(nm): 767.

EXAMPLE 57

Synthesis of Silicon [di(1,6-diphenyl-2,3-naphthalocyanine)]di-tert-butylphthalocyanine bis (dimethylhexylvinylsilyloxide)

A mixture of silicon [di(1,6-diphenyl-2,3-naphthalocyanine)] di(2,3-tert-butylphthalocyanine) dihydroxide (320 mg), 7-oct-1-enyldimethylchlorosilane (200 μL), imidazole (136 mg) and dimethylformamide (6 ml) was stirred at room temperature for 12 hours. The resultant was concentrated under vacuum on the rotary evaporator. The residue was chromatographed on a silica gel (70–230 mesh, 60 Å, 2×50 cm) column equilibrated and eluted with hexane. The blue product was vacuum dried and weighed (150 mg).

UV-vis (methylene chloride) (λmax(nm) ): 632, 676, 702, 750.

Fluorescence (methylene chloride) ($\lambda_{max}$(nm) ): 716.

EXAMPLE 58

Synthesis of Silicon (IV)2,3,11,12,20,21,29,30-octabromo-2,3-naphthalocyanine dihydroxide (abbreviated as: silicon octabromo-2,3-naphthalocyanine dihydroxide)

Silicon tetrachloride (114 μL) was added to a mixture of 6,7-dibromo-1,3-diiminobenz[f]isoindoline (433 mg) and 5-tert-butyl-1,3-diiminoisoindoline (100 mg) in freshly distilled quinoline (2 ml) under an argon atmosphere and the mixture heated with stirring at 210° C. for 2 hours. The resultant was allowed to cool, treated with water (2 ml) and refluxed for 15 minutes. The mixture was cooled, treated with ether (4 ml) and filtered washing the solid three times with ether (2 ml each time). The solid was vacuum dried and weighed (0.57 g, dark green solid).

EXAMPLE 59

Synthesis of Silicon (IV)2,3,11,12,20,21,29,30-octabromo-2,3-naphthalocyanine bis (7-oct-1-enyldimethyl silyloxide) (abbreviated as: silicon octabromo-2,3-naphthalocyanine bis (dimethylhexylvinylsilyloxide))

A mixture of silicon octabromo-2,3-naphthalocyanine dihydroxide (500 mg), 7-oct-1-enyl dimethylchlorosilane (256 μL), imidazole (68 mg) and dimethylformamide (5 ml) was stirred at room temperature for 12 hours. The resultant was concentrated under vacuum with a rotary evaporator. The residue was chromatographed on a silica gel (70–230 mesh, 60 Å, 2×50 cm)column equilibrated in hexane. The product was eluted with toluene, vacuum dried and weighed (300 mg).

UV-vis (tetrahydrofuran) ($\lambda_{max}$(nm)): 694, 702 sh.

Fluorescence (tetrahydrofuran) ($\lambda_{max}$(nm)) 706.

EXAMPLE 60

Synthesis of Silicon (IV) 1,4,8,11,15,18,22,25-octaethoxyphthalocyanine dichloride (abbreviated as: silicon octaethoxyphthalocyanine dichloride)

Silicon tetrachloride (600 μL) was added to a mixture of 4,7-diethoxy-1,3-diiminoisoindoline (1.0 g) in freshly distilled quinoline (10 ml) under an argon atmosphere and the mixture heated with stirring at 200° C. for 1.5 hours. The resultant was allowed to cool and treated with water (10 ml)followed by methylene chloride (10 ml). The organic layer was separated and evaporated with a rotary evaporator. The black residue was treated with ether (5 ml) and filtered. The filtrate was dried ($Na_2SO_4$) and the solvent evaporated with a rotary evaporator, vacuum dried and weighed(300 mg, dark green solid).

UV-vis (tetrahydrofuran) ($\lambda_{max}$(nm)): 742.

UV-vis (methylene chloride) ($\lambda_{max}$(nm)): 764.

IR (KBr): 3435, 3060, 2983, 2932, 2228, 1727, 1603, 1504, 1317, 1256, 1218, 1068, 810 $cm^{-1}$.

EXAMPLE 61

Synthesis of 4,7-diethoxy-1,3-diiminoisoindoline

Anhydrous ammonia was slowly bubbled through a stirred mixture of 1,4-diethoxy-2,3-phthalonitrile (1.0 g), 25% sodium methoxide in methanol (1.2 ml), and dry 1-pentanol (20 ml) for 45 minutes. With continued ammonia introduction, the mixture was refluxed for 3 hours. After the resultant had cooled, the solvent was removed with a rotary evaporator. The residue was dried under vacuum and weighed (1.4 g, green solid).

EXAMPLE 62

Synthesis of 5,9,14,18,23,27,32,36,-octamethoxy 2,3-naphthalocyanine (abbreviated as: octamethoxy-2,3-naphthalocyanine)

1,4-dimethoxynaphthalene-2,3-dicarbonitrile (820 mg) suspended in 25% sodium methoxide in methanol (7 ml) was refluxed for 1.5 hours, cooled, and stirred into glacial acetic acid (50 ml). After 30 minutes, the solvent was evaporated with a rotary evaporator and the residue dissolved in methylene chloride (100 ml). The solution was washed sequentially with 10% hydrochloric acid (100 ml), brine (100 ml) and evaporated with a rotary evaporator. The residue was chromatographed on a silica gel (70–230 mesh, 60 Å, 2×50 cm) column equilibrated in toluene. The product was eluted with toluene, vacuum dried and weighed (52 mg, red-brown solid).

UV-vis (tetrahydrofuran) ($\lambda_{max}$(nm)): 837.

EXAMPLE 63

Synthesis of Germanium (IV)2,3,9/10,16/17,23/24-tetra-tert-butylphthalocyanine dichloride (abbreviated as: Germanium tetra-tert-butylphthalocyanine dichloride)

Germanium tetrachloride (1.5 ml) was added to a mixture of 5-tert-butyl-1,3-diiminoisoindoline (500 mg) and tributylamine(3.4 ml) in 1,2,3,4-tetrahydronaphthalene (7 ml) under an argon atmosphere and the mixture refluxed for 3.5 hours. The resultant was allowed to cool, treated sequentially with water (20 ml) and methylene chloride (20 ml). The organic layer was separated, washed with water (10 ml), dried (MgSO$_4$) and evaporated with a rotary evaporator. The residue was chromatographed on a silica gel (70–230 mesh, 60 Å, 2×50 cm) column equilibrated in toluene. The product was eluted sequentially with toluene and toluene:isopropanol (9:1), vacuum dried and weighed (310 mg).

UV-vis(tetrahydrofuran) ($\lambda_{max}$(nm)): 680.

Fluorescence (tetrahydrofuran) ($\lambda_{max}$(nm)): 718, 750.

EXAMPLE 64

Effect of Human Serum and Blood on the Fluorescence Intensities of Various Dye Systems in Latex with Different Stokes Shifts and Excitation and Emission Wavelengths Donor and acceptor dye pairs or a hybrid phthalocyanine derivative were incorporated into 0.2 micron latex (CML from IDC, Portland, Oreg.) using the tetrahydrofuran solvent system method as indicated in Table 3 and in Example 10. The latex particles were diluted to various solids concentrations as indicated in the Table into either a buffer containing 5 mM potassium phosphate, 1 mM potassium borate, and 5 mg/ml bovine serum albumin, pH 7, neat human serum or neat human blood. The excitation and emission wavelengths and the corresponding Stokes shift are as indicated in Table 6.

The results show that the fluorescence intensities measured in neat human serum and blood are greatly affected when the excitation wavelength is in a region where human serum and blood absorb. Conversely, the fluorescence intensities of latex measured in human serum and blood are not affected when the excitation wavelength is above 646 nm.

TABLE 3

| Dye System (Donor/Acceptor) | Excitation (nm) | Emission (nm) | Stokes Shift | Fluorescence Intensity* | Latex Solids (%) |
|---|---|---|---|---|---|
| trans-4-[4-(Dibutylamino)styryl]-1-methyl pyridinium Iodide/Silicon phthalocyanine bis(dimethylvinylsilyloxide) | 475 | 680 | 205 | | |
| Buffer | | | | 369 | 0.0019 |
| Serum | | | | 28 | 0.0019 |
| Whole Blood | | | | 48 | 0.0019 |
| Meso-tetra-2-aminophenyl porphine/Silicon phthalocyanine bis(dimethylvinylsilyloxide) | 420 | 680 | 260 | | |
| Buffer | | | | 257 | 0.0010 |
| Serum | | | | 72 | 0.0010 |
| Whole Blood | | | | 11 | 0.0010 |
| (E,E)-3,5-bis-(4-phenyl-1,3-butadienyl)-4,4-difluoro-4-bora-3a,4a-diazo-s-indacene/Silicon 2,3-naphthalocyanine bis (dimethyhexylvinylsilyloxide) | 670 | 780 | 110 | | |
| Buffer | | | | 21 | 0.0005 |
| Serum | | | | 20 | 0.0005 |
| Whole Blood | | | | 22 | 0.0005 |
| 1,1'-Dihexyl-3,3,3',3'-tetramethylindodicarbocyanine Iodide/Silicon 2,3-naphthalocyanine bis (dimethyhexylvinylsilyloxide) | 650 | 780 | 130 | | |
| Buffer | | | | 29 | 0.0005 |
| Serum | | | | 30 | 0.0005 |
| Whole Blood | | | | 31 | 0.0005 |
| Silicon phthalocyanine bis-(dimethyhexylvinylsilyloxide)/Silicon [di(1,6-diphenylnaphthalocyanine)] diphthalocyanine bis (dimethyhexylvinylsilyloxide) | 670 | 760 | 90 | | |
| Buffer | | | | 503 | 0.0005 |
| Serum | | | | 483 | 0.0005 |
| Whole Blood | | | | 488 | 0.0005 |
| Hybrid Compound | | | | | |

TABLE 3-continued

| Dye System (Donor/Acceptor) | Excitation (nm) | Emission (nm) | Stokes Shift | Fluorescence Intensity* | Latex Solids (%) |
|---|---|---|---|---|---|
| Silicon [di(1,6-diphenyl-naphthalocyanine)] diphthalocyanine bis (dimethyhexylvinylsilyloxide) | 646 | 760 | 114 | | |
| Buffer | | | | 50 | 0.0007 |
| Serum | | | | 45 | 0.0007 |
| Whole Blood | | | | 47 | 0.0007 |

*Fluorescence intensities are not corrected.

EXAMPLE 65

Effect of Axial Ligand on the Quenching of Silicon [di(1,6-diphenylnaphthalocyanine)] diphthalocyanines Silicon [di(1,6-diphenylnaphthalocyanine)] diphthalocyanine dihydroxide and Silicon [di(1,6-diphenylnaphthalocyanine)]diphthalocyanine bis [dimethylhexylvinylsilyloxide] were incorporated into 0.2 micron CML latex (IDC Corporation, Portland Oreg.) at various dye concentrations as indicated in the Table below using the THF solvent system. The fluorescent latexes were diluted to 0.00057% solids in either 5 mM potassium phosphate, 1 mM potassium borate buffer, pH 7 or in tetrahydrofuran. The fluorescence intensities were measured by excitation at 646 nm. Emission was set at 760 nm. The results are presented below in Table 4.

The results show that the dihydroxy hybrid derivative, which has no axial ligand, has a large degree of quenching, even at 0.1 mg/ml dye loading while the bis dimethylhexylvinylsilyloxide hybrid derivative (with the axial ligand) has very little quenching. The results indicate that axial ligands are important for phthalocyanine derivatives to attain maximum fluorescence intensities in particles.

EXAMPLE 66

Comparison of Quenching in Latex for a Hybrid Phthalocyanine Derivative and a Naphthalocyanine Derivative, Both with Axial Ligands Silicon [di(1,6-diphenylnaphthaolcyanine)] diphthalocyanine bis[dimethylhexylvinylsilyloxide] (hybrid phthalocyanine derivative) and silicon 2,3-naphthalocyanine bis [dimethylhexylvinylsilyloxide] (naphthalocyanine derivative) were incorporated into 0.2 micron CML latex (IDC Corporation, Portland Oreg.) at various dye concentrations as indicated in the Table below using the tetrahydrofuran solvent system. The fluorescent latexes were diluted to 0.00057% solids in either 5 mM potassium phosphate, 1 mM potassium borate buffer, pH 7 or in tetrahydrofuran. The fluorescence intensities were measured at excitation and emission wavelengths as indicated in the Table below.

The results show that the hybrid phthalocyanine derivative is much more resistant to quenching than the naphthalocyanine derivative. The results show the special properties of the hybrid phthalocyanine derivatives for attaining improved fluorescence intensities in latex.

TABLE 4

| Concentration of dye per ml of 2% solid (mg) | Fluorescence Intensity of Latex containing Silicon [di(1,6-diphenyl-naphthalocyanine)] diphthalocyanine dihydroxide | Percent Quench of Silicon [di(1,6-diphenyl-naphthalocyanine)] diphthalocyanine dihydroxide | Fluorescence Intensity of Latex containing Silicon [di(i,6-diphenyl-naphthalocyanine)] diphthalocyanine bis [dimethyl hexylvinyl silyloxide] | Percent Quench of Silicon [di(i,6-diphenyl-naphthalocyanine)] diphthalocyanine bis [dimethyl hexyl-vinylsilyl oxide] |
|---|---|---|---|---|
| 0.1 | 89 | 1 | 0 | 4 |
| 0.2 | 75 | 2 | 6 | 7 |
| 0.3 | 80 | 2 | 0 | 10 |
| 0.4 | 78 | 3 | 2 | 13 |
| 0.6 | 82 | 2 | 3 | 16 |
| 0.8 | 84 | 1 | 5 | 19 |

TABLE 5

| Silicon 2,3-naphthalocyanine bis(dimethyl-hexylvinylsilyl-oxide) concentration (mg/mL) | Fluorescence Intensity of Latex (Ex. 350 nm Em. 780 nm) | Percent Quench (Ex. 350 nm Em. 780 nm) | Fluorescence Intensity of Latex (Ex. 650 nm Em. 780 nm) | Percent Quench (Ex. 650 nm Em 780 nm) |
|---|---|---|---|---|
| 0.1 | 11 | 0 | 1 | 15 |
| 0.3 | 34 | 13 | 3 | 30 |
| 0.5 | 41 | 19 | 4 | 34 |
| 0.7 | 63 | 26 | 6 | 41 |
| 0.9 | 31 | 32 | 3 | 46 |
| 1.0 | 31 | 28 | 3 | 42 |
| 2.0 | 33 | 36 | 3 | 47 |
| Silicon [di(1,6-diphenylnaphthalocyanine)] diphthalocyanine bis[dimethyl-hexylvinylsilyl-oxide) concentration (mg/ml) | | | | |
| 0.1 | 11 | 0 | 6 | 0 |
| 0.3 | 31 | 0 | 16 | 0 |
| 0.5 | 56 | 0 | 28 | 0 |
| 0.7 | 60 | 0 | 30 | 0 |
| 0.9 | 78 | 0 | 39 | 0 |

TABLE 5-continued

| Silicon 2,3-naphthalocyanine bis(dimethyl-hexylvinylsilyl-oxide) concentration (mg/mL) | Fluorescence Intensity of Latex (Ex. 350 nm Em. 780 nm) | Percent Quench (Ex. 350 nm Em. 780 nm) | Fluorescence Intensity of Latex (Ex. 650 nm Em. 780 nm) | Percent Quench (Ex. 650 nm Em 780 nm) |
|---|---|---|---|---|
| 1.0 | 82 | 0 | 41 | 0 |
| 2.0 | 113 | 0 | 58 | 13 |

EXAMPLE 67

Incorporation and Characterization of Hybrid Phthalocyanine and Phthalocyanine Derivatives into Particles using Tetrahydrofuran and Dimethylformamide Solvent Systems Hybrid phthalocyanine and phthalocyanine derivatives were incorporated into carboxyl-modified latex (CML, Interfacial Dynamics Corp. Inc., Portland, Oreg.) using the procedures indicated below for the dyes and using dye concentrations as indicated in Table 6. The fluorescence intensities of the latex solutions were measured at the excitation and emission wavelengths and at the latex concentrations (% solids) as indicated in Table 6 for each of the solvent systems used.

a. 50% Tetrahydrofuran Solvent System

Tetrahydrofuran, THF, (0.19 ml) was added, dropwise over a 5 minute period, to a stirring solution of 0.67 ml of 1.5% solids of latex particles at room temperature. The latex suspension was stirred at room temperature for an additional 30 minutes to swell the latex. The dye solution (0.47 ml), which consists of two or three dyes, each at an appropriate concentration in tetrahydrofuran, was added dropwise over 5 minutes to the stirred latex solution, to give the loading dye concentration (in a 1.33 ml volume) as indicated in Table 6. The latex-dye solution was stirred at room temperature for 30 minutes in the dark. The latex solution was then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the % solids of the solution was calculated from the final volume after dialysis and the starting solids concentration.

b. 70% Tetrahydrofuran Solvent System

Tetrahydrofuran (0.19 ml) was added, dropwise over a 5 minute period, to a stirring solution of 0.4 ml of 2.5% solids of latex particles at room temperature. The latex suspension was stirred at room temperature for an additional 30 minutes to swell the latex. The dye solution (0.74 ml), which consists of two or three dyes, each at an appropriate concentration in tetrahydrofuran, was added dropwise over 5 minutes to the stirred latex solution, to give the loading dye concentration (in a 1.33 ml volume) as indicated in Table 6. The latex-dye solution was stirred at room temperature for 30 minutes in the dark. The latex solution was dialyzed and analyzed according to the procedures outlined in the preceding 50% tetrahydrofuran solvent system method.

c. 50% Dimethylformamide Solvent System

Dimethylformamide, DMF, (0.19 ml) was added, dropwise over a 5 minute period, to a stirring solution of 0.67 ml of 1.5% solids of latex particles at room temperature. The latex suspension was stirred at room temperature for an additional 30 minutes to swell the latex. The dye solution (0.47 ml), which consists of two or three dyes, each at an appropriate concentration in dimethylformamide, was added dropwise over 5 minutes to the stirred latex solution, to give the loading dye concentration (in a 1.33 ml volume) as indicated in Table 6. The latex-dye solution was stirred at room temperature for 30 minutes in the dark. The latex solution was then transferred to dialysis tubing (Spectra-por, 12–14,000 molecular weight cutoff, Spectrum, Houston, Tex.) and the dye-latex solution was dialyzed against water for 12–15 hours at 4° C. The dye-latex solution was removed from dialysis and the % solids of the solution was calculated from the final volume after dialysis and the starting solids concentration.

d. 70% Dimethylformamide Solvent System

Dimethylformamide (0.19 ml) was added, dropwise over a 5 minute period, to a stirring solution of 0.4 ml of 2.5% solids of latex particles at room temperature. The latex suspension was stirred at room temperature for an additional 30 minutes to swell the latex. The dye solution (0.74 ml), which consists of two or three dyes, each at an appropriate concentration in dimethylformamide, was added dropwise over 5 minutes to the stirred latex solution, to give the loading dye concentration (in a 1.33 ml volume) as indicated in Table 6. The latex-dye solution was stirred at room temperature for 30 minutes in the dark. The latex solution was then dialyzed and analyzed according to the proceedures outlined in the preceding 50% dimethylformamide solvent system method.

TABLE 6

| Dye Systems | Loading conc. mg/ml | Molar Ratio | Emission (excit.) | % Solid (latex size) | Fluorescence Intensity of particles made in various dye loading solvent system | | | |
|---|---|---|---|---|---|---|---|---|
| | | | | | 50% THF | 70% THF | 50% DMF | 70% DMF |
| 1. Silicon phthalocyanine bis(dimethylvinylsilyloxide) + Silicon 2,3-naphthalocyanine bis(dimethylhexylvinylsilyloxide) | 0.066/ 0.1 | 1:1 | 785 nm (670 nm) | 0.00057% (0.216 μm) | 21.6 | Not performed | 0.4 | Not performed |
| 2. Silicon phthalocyanine bis(dimethylhexylvinylsilyloxide) + Silicon 2,3-naphthalocyanine bis(dimethylhexylvinylsilyloxide) | 0.08/ 0.1 | 1:1 | 785 nm (670 nm) | 0.00057% (0.216 μm) | 37.8 | 39.1 | 13.5 | 12.7 |
| 3. Silicon phthalocyanine bis(dimethylhexylvinylsilyloxide) + Silicon [di(1,6-diphenyl-2,3-naphthalocyanine)] diphthalocyanine bis(dimethylhexylvinylsilyloxide) | 0.35/ 0.5 | 1:1 | 760 nm (670 nm) | 0.00057% (0.216 μm) | 99.5 | 118.0 | 22.7 | 6.6 |
| 4. Silicon phthalocyanine | 0.35/ | 1:1: | 785 nm | 0.00057% | 86.9 | 105.9 | 18.5 | 7.7 |

TABLE 6-continued

| Dye Systems | Loading conc. mg/ml | Molar Ratio | Emission (excit.) | % Solid (latex size) | Fluorescence Intensity of particles made in various dye loading solvent system | | | |
|---|---|---|---|---|---|---|---|---|
| | | | | | 50% THF | 70% THF | 50% DMF | 70% DMF |
| bis(dimethylhexylvinylsilyloxide) + Silicon [di(1,6-diphenyl-2,3-naphthalocyanine)] diphthalocyanine bis(dimethylhexylvinylsilyloxide) + Silicon 2,3-naphthalocyanine bis(dimethylhexylvinylsilyoxide) | 0.5/ 0.1 | 0.023 | (670 nm) | (0.216 μm) | | | | |

EXAMPLE 68

Synthesis of 4,7-diphenyl-1,3-diiminoisoindoline

Anhydrous ammonia was slowly bubbled through a stirred mixture of 3,6-diphenylphthalonitrile (5.9 g), [synthesized according to J. Am. Chem. Soc. 75, 4338 (1953) and J. Org. Chem., USSR (English Translation) 8, 341 (1972)], 25% sodium methoxide in methanol (1.35 ml), and dry 1-butanol (20 ml) for 1 hour. With continued ammonia introduction, the mixture was refluxed for 1.5 hours. After the resultant had cooled the product was collected by filtration, washed sequentially with 1-butanol (10 ml) and ether (10 ml), vacuum dried and weighed (0.62 g).

EXAMPLE 69

Synthesis of [2,12-di-(2,3)-naphtho[b,l]-$7^1,7^4,17^1$, $17^4$-tetraphenyldibenzo[g,q]-5,10,15,20-tetraazoporphyrinato]silicon dihydroxide (abbreviated as: Silicon [di(2,3-naphthalocyanine) [di(1,4-diphenylphthalocyanine) dihydroxide))

Silicon tetrachloride (69 μL) was added to a mixture of 4,7-diphenyl-1,3-diiminoisoindoline (119 mg) and 1,3-diiminobenz[f]isoindoline (39 mg) in freshly distilled quinoline (1 ml) under an argon atmosphere and the mixture heated with stirring at 200° C. for 1 hour. The resultant was allowed to cool to 160° C., treated with water (1 ml) and refluxed for 5 minutes. The mixture was cooled, treated with ether (10 ml) and filtered, washing the solid sequentially with water (5 ml) and ether (5 ml). The organic layer of the filtrate was separated from the aqueous layer washed sequentially with 1N hydrochloric acid (10 ml) and water (10 ml), dried (MgSO$_4$) and evaporated with a rotary evaporator. The residue was chromatographed on a silica gel (70–230 mesh, 60 Å, 2×50 cm) column equilibrated in methylene chloride. The product was eluted with methylene chloride—1% isopropanol, vacuum dried and weighed (43 mg).

UV-vis (tetrahydrofuran) ($\lambda_{max}$(nm)): 690, 736, 758

Fluorescence (tetrahydrofuran) ($\lambda_{max}$(nm)): 774

EXAMPLE 70

Synthesis of [2,12-di-(2,3)-naphtho[b,l]-$7^1,7^4,17^1$, $17^4$-tetraphenyldibenzo[g,q]-5,10,15,20-tetraazoporphyrinato]silicon bis (7-oct-1-enyldimethylsilyloxide), (abbreviated as: Silicon (di (2,3-naphthalocyanine)]di(1,4-diphenylphthalocyanine)bis (dimethylhexylvinylsilyloxide))

A mixture of silicon [di(2,3-napthalocyanine)]di(1,4-diphenylphthalocyanine) dihydroxide (10.6 mg). 7-oct-1-enyldimethylchlorosilane (41 μL), imidazole (11 mg) and dimethylformamide (200 μL) was stirred at room temperature for 30 minutes. The resultant was concentrated under vacuum on the rotary evaporator. The residue was chromatographed on a silica gel (70–230 mesh, 60 Å, 2×50 cm) column equilibrated in hexane. The product was eluted with toluene, vacuum dried and weighed (3 mg).

UV-vis (tetrahydrofuran) ($\lambda_{max}$(nm)): 667, 745

Fluorescence (tetrahydrofuran) ($\lambda_{max}$(nm)): 774

EXAMPLE 71

Synthesis of [2,12-di-(2,3)-naphtho[b,l]-$7^1,7^4,17^1$, $17^4$-tetraphenyl dibenzo[g,q]-5,10,15,20-tetraazoporphyrinato]silicon bis (dimethylpentafluorophenylsilyloxide), (abbreviated as: Silicon[di(2,3-naphthalocyanine]di(1,4-diphenylphthalocyanine)bis (dimethylpentafluorophenylsilyloxide))

A mixture of silicon [di(2,3-naphthalocyanine)]di(1,4-diphenylphthalocyanine) dihydroxide (10 mg), chlorodimethylpentafluorophenylsilane (28 μL), imidazole (10 mg) and dimethylformamide (200 μL) was stirred at room temperature for 10 minutes. The resultant was concentrated under vacuum on the rotary evaporator. The residue was chromatographed on a silica gel (70–230 mesh, 60 Å, 2×50 cm) column equilibrated in hexane. The product was eluted with toluene, vacuum dried and weighed (3 mg).

UW-vis (tetrahydrofuran) ($\lambda_{max}$(nm)): 701, 754

Fluorescence (tetrahydrofuran) ($\lambda_{max}$(nm)): 789

EXAMPLE 72

Synthesis of [$2^1,2^6,12^1,12^6$,-tetraphenyldinaphtho[b, l]-$7^{2/3},17^{2/3}$-di(tert-butyl)dibenzo[g,q]-5,10,15,20-tetraazoporphyrinato]silicon dihydroxide (abbreviated as: Silicon [di(1,6-diphenyl-2,3-naphthalocyanine)]di 2,3-tert-butylphthalocyanine) dihydroxide))

Silicon tetrachloride (344 μL) was added to a mixture of diphenyl-1,3-diiminobenz[f]isoindolmine (869 mg) and 5-tert-butyl-1,3-diiminoisoindoline (100.5 mg) in freshly distilled quinoline (2 ml) under an argon atmosphere and the mixture heated with stirring at 200° C. for 1 hour. The resultant was allowed to cool to 150° C., treated with water (3 ml) and refluxed for 10 minutes. The mixture was cooled, treated with ether (30 ml) and filtered, washing the solid sequentially with ether (20 ml) and water (20 ml). The organic layer of the filtrate was separated from the aqueous layer, washed sequentially with 1N hydrochloric acid (2×10 ml) and water (10 ml), dried (MgSO$_4$) and evaporated with a rotary evaporator. The residue was chromatographed three times on a silica gel (70–230 mesh, 60 Å, 2×50 cm) column equilibrated in hexane. The product was eluted sequentially with methylene chloride and methylene chloride—1% isopropanol, vacuum dried and weighed (55 mg).

UV-vis (tetrahydrofuran) ($\lambda_{max}$(nm)): 646, 684, 720, 743

Fluorescence (tetrahydrofuran) ($\lambda_{max}$(nm)): 750

EXAMPLE 73

Synthesis of [$2^1,2^6,12^1,12^6$-tetraphenyldinaphtho[b,l]-$7^{2/3},17^{2/3}$-di (tert-butyl)dibenzo[g,q]-5,10,15,20-tetraazoporphyrinato]silicon bis (7-oct-1-enyldimethylsilyloxide) (abbreviated as: Silicon[di (1,6-diphenyl-2,3-naphthalocyanine)]di(2,3-tert-butylphthalocyanine bis (dimethylhexylvinylsilyloxide))

A mixture of Silicon di(1,6-diphenyl-2,3-naphthalocyanine)] di (2,3-tert-butylphthalocyanine) dihydroxide (2.8 mg) and dimethylformamide (500 μL) was stirred at room temperature for 10 minutes. The resultant was concentrated under vacuum on the rotary evaporator. The residue was chromatographed on a silica gel (70–230 mesh, 60 Å, 2×50 cm) column equilibrated in hexane. The product was eluted sequentially with hexane and toluene, vacuum dried and weighed (16.5 mg).

UV-vis (tetrahydrofuran) ($\lambda_{max}$(nm):648, 688, 726, 750

Fluorescence (tetrahydrofuran) ($\lambda_{max}$(nm):756

EXAMPLE 74

Synthesis of [$2^1,2^6,12^1,12^6$-tetraphenyldinaphtho[b,l]-$7^{2/3},17^{2/3}$-di (tert-butyl)dibenzo[g,q]-5,10,15,20-tetraazoporphyrinato]silicon bis (dimethylpentafluorophenylsilyloxide) (abbreviated as: Silicon [di(1,6-diphenyl-2,3-naphthalocyanine)] di(2,3-tert-butylphthalocyanine) bis (dimethylpentafluorophenylsilyloxide))

A mixture of Silicon [di(1,6-diphenyl-2,3-naphthalocyanine)] di(2,3-tert-butylphthalocyanine) dihydroxide (21.8 mg), chlorodimethylpentafluorophenylsilane (56.5 μL), imidazole (20.4 mg) and dimethylformamide (500 μL) was stirred at room temperature for 10 minutes. The resultant was concentrated under vacuum on the rotary evaporator. The residue was chromatographed on a silica gel (70–230 mesh, 60 Å)column (2×50 cm) equilibrated in hexane. The product was eluted sequentially with hexane and toluene, vacuum dried and weighed (25 mg).

UV-vis (tetrahydrofuran) ($\lambda_{max}$(nm)): 652, 694, 730, 760

Fluorescence (tetrahydrofuran) ($\lambda_{max}$(nm)): 769

EXAMPLE 75

Synthesis of [$2^1,2^6,12^1,12^6$-tetraphenyldinaphtho[b,l]-7-(2,3)-naphtho[g]-17-benzo[q]-5,10,15,20-tetraazoporphyrinato]silicon dihydroxide (abbreviated as: Silicon[di(1,6-diphenyl-2 3-naphthalocyanine)] (2,3-naphthalocyanine) phthalocyanine dihydroxide)

Silicon tetrachloride (172 μL) was added to a mixture of diphenyl-1,3-diiminobenz[f]isoindoline (347 mg), 1,3-diiminobenz[f]isoindoline (49 mg) and 1,3-diiminoisoindoline (36 mg) in freshly distilled quinoline (2 ml) under an argon atmosphere and the mixture heated with stirring at 200° C. for 1 hour. The resultant was allowed to cool to 170° C., treated with water (2 ml) and refluxed for 5 minutes. The mixture was cooled, treated with ether (20 ml) and filtered, washing the solid sequentially with water (5 ml) and ether (10 ml). The organic layer was separated from the aqueous layer, washed with 1N hydrochloric acid (2×10 ml), (filtering again to effect separation) and water (10 ml), dried (MgSO$_4$) and evaporated with a rotary evaporator. The residue was chromatographed on a silica gel (70–230 mesh, 60 Å)column (2×50 cm) equilibrated in hexane. The product was eluted sequentially with toluene, toluene—5% methylene chloride, toluene—10% methylene chloride, toluene—20% methylene chloride and finally toluene—50% methylene chloride. The product was then re-chromatographed on silica gel (GF,1000μ, 20×20 cm) plates eluting sequentially (air drying the plates between each elution) with toluene—5% methylene chloride, toluene—10% methylene chloride, toluene—20% methylene chloride and finally toluene—50% methylene chloride. The plates were eluted in the latter solvent ten times to effect separation of the desired product from by-products. The green product was vacuum dried and weighed (9 mg).

UV-vis (tetrahydrofuran) ($\lambda_{max}$(nm)): 670, 714, 750

Fluorescence (tetrahydrofuran) ($\lambda_{max}$(nm)): 762

EXAMPLE 76

Synthesis of [$2^1,2^6,12^1,12^6$-tetraphenyldinaphtho[b,l]-7-(2,3)-naphtho[g]-17-benzo[q]-5,10,15,20,-tetraazoporphyrinato]silicon bis(7-oct-1-enyldimethylsilyloxide) (abbreviated as: Silicon[di (1,6-diphenyl-2,3-naphthalocyanine)] (2,3-napthalocyanine) phthalocyanine bis (dimethylhexylvinylsilyloxide))

A mixture of [di(1,6-diphenyl-2,3-naphthalocyanine)] (2,3 -naphthalocyanine) phthalocyanine dihydroxide (9 mg), 7-oct-1-enyldimethylchlorosilane (33.5 μL), imidazole (9 mg) and dimethylformamide (200 μL) was stirred at room temperature for 10 minutes. The resultant was concentrated under vacuum on the rotary evaporator. The residue was chromatographed on a silica-gel (GF,1000μ, 20×20 cm) plate eluting with hexane—50% methylene chloride. The product was triturated twice with hexane (1 ml), vacuum dried and weighed (9 mg).

UV-vis (tetrahydrofuran) ($\lambda_{max}$(nm)): 674, 718, 756

Fluorescence (tetrahydrofuran) ($\lambda_{max}$(nm)): 763

EXAMPLE 77

Synthesis of [$2^1,2^6$-diphenylnaphtho[b,]-7,12,17-tribenzo[g,l,q]-5,10,15,20-tetraazoporphyrinato] silicon dihydroxide (abbreviated as: Silicon (1,6-diphenyl-2,3-naphthalocyanine) triphthalocyanine dihydroxide)

Silicon tetrachloride (687 μL) was added to a mixture of diphenyl-1,3-diiminobenz[f]isoindoline (347 mg) and 1,3-diiminoisoindoline (726 mg) in freshly distilled quinoline (5 ml) under an argon atmosphere and the mixture heated with stirring at 200° C. for 1 hour. The resultant was allowed to cool to 170° C., treated with water (5 ml) and refluxed for 5 minutes. The mixture was cooled, treated with ether (20 ml) and filtered, washing the solid sequentially with water (10 ml) and ether (10 ml). The organic layer was separated from the aqueous layer, washed sequentially with 1N hydrochloric acid (50 ml), (re-filtering to effect separation) and water (50 ml), dried (MgSO$_4$) and evaporated with a rotary evaporator. The filtered solids were treated with acetone (20 ml) and re-filtered washing with acetone (10 ml). The filtrate was dried (MgSO$_4$) and evaporated with a rotary evaporator. The residues from the ether and acetone evaporations were combined and chromatographed on a silica gel (70–230 mesh, 60 Å)column(2×50 cm) equilibrated in hexane. The product was eluted sequentially with methylene chloride, toluene and toluene—1% isopropanol. The product was then re-chromatographed on silica gel (GF, 1000μ, 20×20 cm)plates eluting with methylene chloride , air drying the plates and re-eluting with toluene—1% isopropanol. The blue-green product was vacuum dried and weighed (60 mg).

UV-vis (tetrahydrofuran) ($\lambda_{max}$(nm)): 622, 658, 688, 698

EXAMPLE 78

Synthesis of [2$^1$,2$^6$,12$^1$,12$^6$-tetraphenyldinaphtho[b, l]-7, 17-dibenzo[g,q]-5,10,15,20-tetraazoporphyrinato] silicon bis(trihexylsilyloxide) (abbreviated as: Silicon [di(1,6-diphenyl-2,3-naphthalocyanine)] diphthalocyanine bis (trihexylsilyloxide))

A mixture of Silicon [di(1,6-diphenyl-2,3-naphthalocyanine)] diphthalocyanine dihydroxide (8 mg), chlorotrihexylsilane (55 μL), imidazole (10 mg) and dimethylformamide (200 μL) was stirred at room temperature for 10 minutes. The resultant concentrated under vacuum on the rotary evaporator. The residue was chromatographed on a silica gel (70–230 mesh, 60 Å)column (2×50 cm) equilibrated in hexane. The product was eluted sequentially with hexane and toluene, vacuum dried and weighed (4.5 mg).

UV-vis (tetrahydrofuran) ($\lambda_{max}$(nm)): 644, 684, 718, 748

Fluorescence (tetrahydrofuran) ($\lambda_{max}$(nm)): 752

EXAMPLE 79

Synthesis of [2$^1$,2$^6$-diphenylnaphtho[b]-7,12,17-tribenzo[g,l,q]-5,10,15,20-tetraazoporphyrinato] silicon bis(7-oct-1-enyldimethylsilyloxide) (abbreviated as: Silicon(1,6-diphenyl-2,3-naphthalocyanine) triphthalocyanine bis (dimethylhexylvinylsilyloxide))

A mixture of Silicon (1,6-diphenyl-2,3-naphthalocyanine) triphthalocyanine dihydroxide (23.3 mg), 7-oct-1-enyldimethylchlorosilane (115.2 μL), imidazole (30.6 mg) and dimethylformamide (500 μL) was stirred at room temperature for 10 minutes. The resultant was concentrated under vacuum on the rotary evaporator. The residue was treated with hexane (2 ml), filtered from yellow insoluble solid and the filtrate evaporated. The residue was chromatographed on a silica gel (GF, 1000μ, 20×20 cm) plate eluting with hexane, air drying the plate and re-eluting with hexane—50% methylene chloride. The product was vacuum dried and weighed (0.8 mg).

NMR(500 MHZ, CDCl$_3$) δ 9.54(m,2H), 9.47(d,2H) 8.41 (d,2H), 8.37(m,2H), 8,25(m,2H), 8.19(dd,2H), 8.09(dd,2H), 8.02(m,10H), 5.65(m,2H), 4.90(m,4H), 1.67(m,4H), 0.76 (m,4H), −0.11(m,4H), −1.25 (m,4H), −2.17 (m,4H), −2.79 (s,12H).

UV-vis (tetrahydrofuran) ($\lambda_{max}$(nm)): 624, 660, 692

Fluorescence (tetrahydrofuran) ($\lambda_{max}$(nm)): 710

EXAMPLE 80

Synthesis of [2$^1$,2$^6$,12$^1$,12$^6$-tetraphenyldinaphtho[b, l]-7, 17-dibenzo[g,q]-5,10,15,20-tetraazoporphyrinato]silicon bis (7-oct-1-enyldimethylsilyloxide) (abbreviated as: Silicon[di (1,6-diphenyl-2,3-naphthalocyanine)] di(2,3-naphthalocyanine) bis(dimethylhexylvinylsilyloxide) )

A mixture of Silicon[di(1,6-diphenyl-2,3-naphthalocyanine)] di(2,3-naphthalocyanine) dihydroxide (6 mg), 7-oct-1-enyldimethylchlorosilane (21 μL), imidazole (5.7 mg) and dimethylformamide (200 μL) was stirred at room temperature for 10 minutes. The resultant was concentrated under vacuum on the rotary evaporator. The residue was chromatographed on a silica gel (GF, 1000μ, 20×20 cm) plate eluting sequentially (air drying the plate between each elution) with hexane—20% toluene, hexane—50 % toluene and toluene. The green product was triturated three times with hexane (1 ml), vacuum dried and weighed (5.4 mg).

NMR (500 MHZ, CDCl$_3$) δ 8.75 (b,4H), 8.38(m,8H) 8.15(m,4H), 8.03(m,16H), 7.80(m,8H), 5.40(m,2H), 4.70 (m,4H), 1.38(m,4H), 0.59(m,4H), 0.16(m,4H), −0.05(m, 4H), −1.08(m,4H), −1.97(m,4H), −2.58(s,12H).

UV-vis (tetrahydrofuran) ($\lambda_{max}$(nm)): 668,696,746,784

Fluorescence (tetrahydrofuran) ($\lambda_{max}$(nm)) 792

EXAMPLE 81

5,6-dicyano-1,3-diiminoisoindoline

Anhydrous ammonia was slowly bubbled through a stirred mixture of benzene-1,2,4,5-tetracarbonitrile (1.78 g), and dry methanol (40 ml) for 1 hour. The product was collected by filtration, washed sequentially with methanol (10 ml) and ether (10 ml), vacuum dried and weighed (2.07 g).

EXAMPLE 82

Synthesis of [2$^1$,2$^6$,12$^1$,12$^6$-tetraphenyldinaphtho[b, l]-7$^2$,7$^3$,17$^2$,17$^3$-tetracyanodibenzo[g,q]-5,10,15,20-tetraazoporphyrinato] silicon dihydroxide Silicon tetrachloride (115 μL) was added to a mixture of diphenyl-1,3-diiminobenz[f]isoindoline (174 mg)and 5,6-dicyano-1,3-diiminoisoindoline (98 mg) in freshly distilled quinoline (2 ml) under an argon atmosphere and the mixture heated with stirring 200° C. for 1 hour. The resultant was allowed to cool to 170° C. treated with water (2 ml) and refluxed for 5 minutes. The mixture was cooled, treated with ether (20 ml) and filtered, washing the solid sequentially with water (10 ml) and ether (10 ml). The filtered dark green insoluble solid was treated with acetone (20 ml), filtered, treated with methylene chloride (20 ml) and re-filtered washing with methylene chloride (20 ml). The acetone/methylene chloride filtrate was dried (MgSO$_4$) and evaporated with a rotary evaporator. The residue was chromatographed on a silica gel (70–230 mesh, 60 Å)column (2×50 cm) equilibrated in hexane. The product was eluted sequentially with methylene chloride and methylene chloride—1% isopropanol, vacuum dried and weighed (63 mg).

IR (KBr) 2233 cm$^{-1}$ (CN)

UV-vis (tetrahydrofuran) ($\lambda_{max}$(nm)): 627, 686, 746, 826

Fluorescence (tetrahydrofuran) ($\lambda_{max}$(nm)): 831

EXAMPLE 83

Synthesis of [2$^1$,2$^6$,12$^1$,12$^6$-tetraphenyldinaphtho[b, l]-7$^2$,7$^3$,17$^2$,17$^3$-tetraacyanodibenzo[g,q]-5,10,15,20-tetraazoporphyrinato]silicon bis(7-oct-1-enyldimethylsilyloxide) (abbreviated as: Silicon [di (1,6-diphenyl-2,3-naphthalocyanine)] di(2,3-dicyanophthalocyanine) bis (dimethylhexylvinylsilyloxide))

A mixture of Silicon [di(1,6-diphenyl-2,3-naphthalocyanine)] di(2,3-dicyanophthalocyanine) dihydroxide (21.6 mg), 7-oct-1-enyldimethylchlorosilane (77 μL), imidazole (20.4 mg) and dimethylformamide (500 μL) was stirred at room temperature for 10 minutes. The resultant was concentrated under vacuum on the rotary evaporator. The residue was chromatographed on a silica gel (GF, 1000μ, 20×20 cm) plate eluting with hexane, air drying the plate and re-eluting with methylene chloride. The product was vacuum dried and weighed (4 mg).

NMR (500 MHZ, CDCl$_3$) δ 8.65 (s,4H), 8.38(m,4H) 8.16(m,4H), 8.02(m,4H), 7.94(m,8H), 7.87(m,4H), 5.51(m, 2H), 4.81(m,4H), 1.55(m,4H), 0.71(m,4H), 0.24(m.4H), −0.06(m,4H), −1.19(m,4H), −2.07(m,4H), −2.71(s,2H)

UV-vis (tetrahydrofuran)($\lambda_{max}$(nm)): 631, 693, 752, 835

Fluorescence (tetrahydrofuran) ($\lambda_{max}$(nm)): 839

EXAMPLE 84

Synthesis of [2,7/12-di-(2,3)-naphtho[b,g/l]-$7^2,7^3$, $12^2 12/17^2,17^3$ tetracyanodibenzo[g,/q]-5,10,15,20-tetraazoporphyrinato] silicon dihydroxide (abbreviated as: Silicon [di(2,3-naphthalocyanine)] di(2,3-dicyanophthalocyanine) dihydroxide)

Silicon tetrachloride (330 μL) was added to a mixture of 1,3-diiminobenz[f]isoindoline (195 mg) and 5,6-dicyano-1,3-diiminoisoindoline (195 mg) in freshly distilled quinoline (4 ml) under an argon atmosphere and the mixture heated with stirring at 200° C. for 1 hour. The resultant was allowed to cool to 160° C., treated with water (4 ml) and refluxed for 10 minutes. The mixture was cooled, treated with ether (20 ml) and filtered, washing the solid sequentially with water (10 ml), ether (10 ml), and acetone (10 ml). The solid was vacuum dried and weighed (560 mg).

EXAMPLE 85

Synthesis of [2,7/12-di-(2,3)-naphtho[b,g/l]-$7^2,7^3$, $12^2,12^3/17^2,17^3$ tetracyanodibenzo[g,l/q]-5,10,15, 20-tetraazoporphyrinato] silicon bis(7-oct-1-enyldimethylsilyloxide) (abbreviated as: Silicon [di (2,3-naphthalocyanine)] di(2,3-dicyanophthalocyanine) bis (dimethylhexylvinylsilyloxide))

A mixture of Silicon[di(2,3-naphthalocyanine)] di(2,3-dicyanophthalocyanine) dihydroxide (155 mg), 7-oct-1-enyldimethylchlorosilane (770 ml), imidazole (204 mg) and dimethylformamide (2 ml) was stirred at room temperature for 30 minutes. The resultant was concentrated under vacuum on the rotary evaporator. The residue was chromatographed on two silica gel (GF, 2000μ, 20×20 cm) plates eluting with hexane, air drying the plate and re-eluting with methylene chloride. The product was vacuum dried and weighed (3.1 mg).

NMR (500 MHZ, CDCl$_3$) δ 10.3(s,4H), 9.94(s,4H), 8.65 (m,4H), 7.98(m,4H), 5.80(m,1H), 5.59(m,1H), 4.92 (m,4H), 1.56(m,4H), 0.71(m,4H), 0.26(m,4H), −0.05(m,4H), −0.96 (m,4H), −1.83(m,4H), −2.44,(s, 12H)

UV-vis (tetrahydrofuran) ($\lambda_{max}$(nm)): 649, 704,731,788

Fluorescence (tetrahydrofuran) ($\lambda_{max}$(nm)): 795

EXAMPLE 86

Synthesis of [2,7/12-di-(2,3)-naphtho[b,g/l]-$7^2,7^3$, $12^2,12^3/17^2,17^3$ tetracyanodibenzo[g,l/q]-5,10,15, 20-tetraazoporphyrinato] silicon bis (dimethylpentafluorophenylsilyloxide) (abbreviated as: Silicon [di(2,3-naphthalocyanine)] di(2,3-dicyanophthalocyanine) bis (dimethylpentafluorophenylsilyloxide))

A mixture of Silicon [di(2,3-naphthalocyanine)] di(2,3-dicyanophthalocyanine) dihydroxide (155 mg), chlorodimethylpentafluorophenylsilane (565 μL), imidazole (204 mg) and dimethylformamide (2 ml) was stirred at room temperature for 1 hour. The resultant was concentrated under vacuum on the rotary evaporator. The residue was chromatographed on two silica gel (GF, 1000μ, 20×20 cm) plates eluting with hexane, air drying the plate and re-eluting with methylene chloride, vacuum dried and weighed (3 mg).

UV-vis (tetrahydrofuran) ($\lambda_{max}$(nm)): 656,712, 740, 800

Fluorescence (tetrahydrofuran) ($\lambda_{max}$(nm)): 807

EXAMPLE 87

Synthesis of 5,6-dichloro-1,3-diiminoisoindoline

Anhydrous ammonia was slowly bubbled through a stirred mixture of 4,5-dichlorphthalonitrile (1.0 g), 8% sodium butoxide in 1-butanol (500 μL), 1,4-dioxane (1 ml), and dry 1-butanol (10 ml) for 60 minutes. With continued ammonia introduction, the mixture was refluxed for 2 hours. After the resultant had cooled, the product was collected by filtration, washed with methylene chloride (20 ml), vacuum dried and weighed (0.63 g).

EXAMPLE 88

Synthesis of [$2^1,2^6,12^1,12^6$-tetraphenyldinaphtho[b, 1]-$7^2, 7^3,17^2,17^3$-tetrachlorodibenzo[g,q]-5,10,15,20-tetraazoporphyrinato] silicon dihydroxide (abbreviated as: Silicon [di(1,6-diphenyl-2,3-naphthalocyanine)] di(2,3-dichlorophthalocyanine) dihydroxide)

Silicon tetrachloride (500 μL) was added to a mixture of 5,6-dichloro-1,3-diiminoisoindoline (308 mg) and 4,7-diphenyl-1,3-diiminobenz[f]isoindoline (900 mg) in freshly distilled quinoline (14 ml) under an argon atmosphere and the mixture heated with stirring at 210° C. for 1 hour. The resultant was allowed to cool to 160° C., treated with water (3 ml) and refluxed for 10 minutes. The mixture was cooled, treated with ether (50 ml) and filtered, washing the solid sequentially with water (50 ml) and ether (100 ml). The organic layer of the filtrate was separated from the aqueous layer, washed sequentially with 1N hydrochloric acid (50 ml) and water (100 ml) and evaporated with a rotary evaporator. The residue was chromatographed on a silica gel (70–230 mesh, 60 Å)column (2×50 cm) equilibrated in hexane. The product was eluted with toluene—10% isopropanol, vacuum dried and weighed (340 mg).

UV-vis (tetrahydrofuran) ($\lambda_{max}$(nm)): 716, 766, 694.

EXAMPLE 89

Synthesis of [$2^1,2^6,12^1,12^6$-tetraphenyldinaphtho[b, 1]-$7^2,7^3,17^2,17^3$-tetrachlorodibenzo[g,q]-5,10,15,20-tetraazoporphyrinato]silicon bis (7-oct-1-enyldimethylsilyloxide), (abbreviated as: Silicon [di (1,6-diphenyl-2,3-naphthalocyanine)]di(2,3-dichlorophthalocyanine)bis (dimethylhexylvinylsilyloxide))

A mixture of silicon [di(1,6-diphenyl-2,3-naphthalocyanine)]di(2,3-dichlorophthalocyanine) dihydroxide (340 mg), 7-oct-1-enyldimethylchlorosilane (1.1 ml), imidazole (325 mg) and dimethylformamide (7 ml) was stirred at room temperature for 48 hours. The resultant was concentrated under vacuum on the rotary evaporator. The residue was chromatographed on a silica gel (70–230 mesh, 60 Å) column(2×50 cm) equilibrated in hexane. The product was eluted with toluene, vacuum dried and weighed (75 mg).

UV-vis (tetrahydrofuran) (λmax(nm)): 720,770,698.
Fluorescence (tetrahydrofuran) ($\lambda_{max}$(nm)): 781

EXAMPLE 90

Synthesis of [$2^1,2^6,12^1,12^6$-tetraphenyldinaphtho[b, 1]-7,17-dibenzo(g,q]-5,10,15,20-tetraazoporphyrinato]silicon bis (octyloxide) (abbreviated as: Silicon di[(1,6-diphenyl)-2,3-naphthalocyanine)]diphthalocyanine bis (octyloxide)

A mixture of Silicon di(1,6-diphenyl)-2,3-naphthalocyanine]diphthalocyanine dihydroxide (49 mg) and 1-octanol (1 ml) was refluxed with stirring on an oil bath at 235° C. for 3 hours. The resultant was concentrated under vacuum on the rotary evaporator (using a water bath at 60° C.). The residue was chromatographed on two silica gel (GF, 1000μ20×20 cm) plates eluting with methylene chloride three times (air drying the plates between each elution). The product was vacuum dried and weighed (19 mg), UV-vis (tetrahydrofuran) ($\lambda_{max}$(nm)): 642, 682, 716, 746
Fluorescence (tetrahydrofuran) ($\lambda_{max}$(nm)): 751

EXAMPLE 91

Synthesis of [$2^1,2^6,12^1,12^6$-tetraphenyldinaphtho[b, 1]-7,17-dibenzo(g,g]-5,10,15,20-tetraazoporphyrinato]silicon bis (octyloxide) (abbreviated as: Silicon di[(1,6-diphenyl)-2,3-naphthalocyanine]diphthalocyanine bis (phenoxide)

A mixture of Silicon di[(1,6-diphenyl)-2,3-naphthalocyanine]diphthalocyanine dihydroxide (49 mg), and phenol (1 g) was refluxed with stirring on an oil bath at 220° C. for 2 hours. The resultant was allowed to cool and chromatographed on a silica gel (70–230 mesh, 60 Å) column (2×50 cm) equilibrated in hexane. The product was eluted with hexane—50% methylene chloride, vacuum dried and weighed (13 mg).

UV-vis (tetrahydrofuran) ($\lambda_{max}$(nm)): 654, 704, 732, 768
Fluorescence (tetrahydrofuran) ($\lambda_{max}$(nm)): 776

EXAMPLE 92

Synthesis of [$2^1,2^6,12^1,12^6$-tetraphenyldinaphtho[b, 1]-7,17-dibenzo(g,q]-5,10,15,20-tetraazoporphyrinato]silicon bis [poly(ethylene glycol)methyl ether] (abbreviated as: Silicon[di(1,6-diphenyl-2,3 naphthalocyanine)]diphthalocyanine bis [poly(ethylene glycol) methyl ether])

A mixture of Silicon[di(1,6-diphenyl-2,3-naphthalocyanine)]diphthalocyanine dihydroxide (49 mg), poly(ethyleneglycol)methyl ether (400 mg), and 1,2,4-trimethylbenzene (5 ml) was refluxed with stirring on an oil bath at 220° C. for 3 days using a Dean-Stark trap. The resultant was concentrated under vacuum on the rotary evaporator. The residue was chromatographed on a silica gel (70–230 mesh, 60 Å)column(2×50 cm) equilibrated in methylene chloride and eluted sequentially with methylene chloride—1% isopropanol, methylene chloride—5% isopropanol, methylene chloride—20% isopropanol, methylene chloride—50% isopropanol and finally methylene chloride—50% methanol. The product was vacuum dried and weighed (145 mg).

UV-vis (tetrahydrofuran) ($\lambda_{max}$(nm)): 648, 692, 726,758
Fluorescence (tetrahydrofuran) ($\lambda_{max}$(nm)): 765

EXAMPLE 93

Synthesis of [$2^1,2^6,12^1,12^6$-tetraphenyldinaphtho[b, 1]-7,17-dibenzo(g,q]-5,10,15, 20-tetraazoporphyrinato]silicon bis [(4-octyl)phenoxide](abbreviated as: Silicon[di(1,6-diphenyl-2,3 naphthalocyanine)]diphthalocyanine bis [(4-octyl)phenoxide])

A mixture of Silicon [di(1,6-diphenyl-2,3-naphthalocyanine)]diphthalocyanine dihydroxide (42 mg), 4-octylphenol (41 mg) and 1,2,4 - trimethylbenzene (5 ml) was refluxed with stirring on an oil bath at 200° C. for 16 hours. The resultant was concentrated under vacuum on the rotary evaporator. The residue was chromatographed on a silica gel (70–230 mesh, 60 Å)column (2×50 cm) equilibrated in hexane and eluted with hexane—50% methylene chloride. The product was vacuum dried and weighed (49 mg).

UV-vis (tetrahydrofuran) ($\lambda_{max}$(nm)): 644, 684, 716, 746
Fluorescence (tetrahydrofuran)($\lambda_{max}$(nm)): 751

EXAMPLE 94

Silicon 2,3-naphthalocyanine bis (dimethyloctadecylsilyloxide)

A mixture of Silicon 2,3-naphthalocyanine dihydroxide (155 mg), chlorodimethyloctadecylsilane (1.04 g), imidazole (204 mg) and dimethylformamide (5 μL) was stirred at room temperature for 1 hour. The resultant was concentrated under vacuum on the rotary evaporator. The residue was chromatographed on a silica gel (70–230 mesh, 60 Å)column(2×50 cm) equilibrated in hexane. The product was eluted sequentially with hexane and methylene chloride, vacuum dried and weighed (180 mg).

UV-vis (tetrahydrofuran) (λmax(nm)):686, 732, 770
Fluorescence (tetrahydrofuran) ($\lambda_{max}$(nm)): 776

EXAMPLE 95

Synthesis of [$2^1,2^6,12^1,12^6$-tetraphenyldinaphtho[b, 1]-7,17-dibenzo(g,q]-5,10,15,20-tetraazoporphyrinato]silicon bis[poly(ethylene glycol) (abbreviated as: Silicon di[(1,6-diphenyl)-2, 3-naphthalocyanine]diphthalocyanine bis [poly (ethylene glycol)])

A mixture of Silicon di[(1,6-diphenyl)-2,3 naphthalocyanine]diphthalocyanine dihydroxide (49 mg), poly(ethylene glycol) (1 g), and 1,2,4-trimethylbenzene (5 ml) was refluxed with stirring on an oil bath at 210° C. for 3 days using a Dean-Stark trap. The resultant was concentrated under vacuum on the rotary evaporator. The residue was chromatographed on a silica gel(70–230 mesh, 60 Å)column (2×50 cm) equilibrated in methylene chloride and eluted sequentially with methylene chloride—1% isopropanol, methylene chloride—5% isopropanol, methylene chloride—20% isopropanol and finally methylene chloride—50% isopropanol. The product was then re-chromatographed on silica gel GF, 1000μ, 20×20cm) plates eluting sequentially (air drying the plates between each elution) with methylene chloride, methylene chloride-10% methanol and finally tetrahydrofuran. The product was vacuum dried and weighed (152 mg). NMR (500 MHZ, CDCl$_3$) δ 68.30(m,4H), 8.25 (m,4H), 8.00(m,24H,) 7.77(m, 4H) 3.63(m,ICH$_2$'s)

UV-vis (tetrahydrofuran) ($\lambda_{max}$(nm)): 648, 692, 720, 754
Fluorescence (tetrahydrofuran) ($\lambda_{max}$(nm)): 760

EXAMPLE 96

Synthesis of [$2^1,2^6,12^1,12^6$-tetraphenyldinaphtho[b, 1]17,17-dibenzo[g,q]-5,10,15,20-tetraazoporphyrinato]silicon [poly(ethylene glycol)] acetylthiopropionyl poly(ethylene glycol)] (abbreviated as: Silicon di[(1,6-diphenyl)-2,3-naphthalocyaninel diphthalocyanine rpoly(ethylene glycol)] fpoly(ethylene glycol)acetylthiopropionatel)

A mixture of acetylthiopropionic acid, (15 mg), 1,1'-carbonyldiimidazole (16 mg) and dimethylformamide (1 ml)

was stirred at room temperature for 40 minutes. A portion of this solution ( 100 μL) was added to Silicon di[(1,6-diphenyl)-2,3-naphthalocyanine]diphthalocyanine bis [poly (ethylene glycol)] (49.5 mg) and the mixture stirred at room temperature for 3 days. The resultant was concentrated under vacuum on the rotary evaporator. The residue was chromatographed on a silica gel (GF, 1000μ, 20×20 cm) plate eluting with tetrahydrofuran, vacuum dried and weighed (3 mg).

UV-vis (tetrahydrofuran)($\lambda_{max}$(nm)): 644, 690, 718, 750

Fluorescence (tetrahydrofuran) ($\lambda_{max}$(nm)): 754

EXAMPLE 97

Synthesis of [$2^1,2^6,12^1,12^6$-tetraphenyldinaphtho[b, l]-$7^2,7^3,17^2,17^3$-tetracarboxydibenzo[g,q]-5,10,15, 20-tetraazoporphyrinato]silicon dihydroxide (abbreviated as: Silicon di[(1,6-diphenyl)2,3-naphthalocyanin]di(2,3-dicarboxyphthalocyanine) dihydroxide)

A mixture of Silicon di[(1,6-diphenyl)-2,3-naphthalocyanine]di(2,3-dicyanophthalocyanine) dihydroxide (36 mg) and concentrated sulfuric acid (200 μL) was heated with stirring at 50° C. for 48 hours. The cooled mixture was then carefully treated with water (150L) and heated with stirring at 100° C. for 20 hours. The cooled mixture was then treated with water (1 ml) and the dark precipitate collected by filtration washing with water (1 ml). The solid was then treated with 1N potassium carbonate solution (1 ml) and refluxed with stirring for 1 hour. The cooled mixture was acidified to pH 2 by dropwise addition of 6N hydrochloric acid and the fine dark green solid product filtered, washing with water (1 ml). The solid was vacuum dried and weighed (20 mg).

UV-vis (tetrahydrofuran) ($\lambda_{max}$(nm)): 636, 658, 716, 788.

Fluorescence (tetrahydrofuran) ($\lambda_{max}$(nm)): 791.

EXAMPLE 98

Synthesis of [$2^1,2^6,12^1,12^6$-tetraphenyldinaphtho[b, l]-$7^2,7^3,17^2,17^3$-tetracarboxydibenzo[g,q]-5,10,15, 20-tetraazoporphyrinato]silicon bis [poly (ethylene glycol) methyl ether](abbreviated as: Silicon di[(1, 6-diphenyl) 2,3-naphthalocyanine]di (2,3-dicarboxyphthalocyanine) bis [poly(ethylene lycol) methyl ether])

A mixture of Silicon di[(1,6-dipheny)-2,3-naphthalocyanine]di (2,3-dicarboxyphthalocyanine) dihydroxide (10 mg), poly(ethylene glycol)methyl ether (80 mg) and 1,2,4-trimethylbenzene (1 ml) was refluxed with stirring on an oil bath at 220° C. for 3 days using a Dean-Stark trap. The resultant was concentrated under vacuum on the rotary evaporator. The residue was chromatographed on a silica gel (GF, 1000μ20×20 cm) plate eluting with methylene chloride—10% methanol, air drying the plate and re-eluting with methylene chloride—10 % methanol. The green product was vacuum dried and weighed (8 mg).

IR (KBr)1712 cm$^{-1}$ (COOH)

UV-vis (tetrahydrofuran) ($\lambda_{max}$(nm):648, 702, 726, 792.

UV-vis (water) ($\lambda_{max}$(nm) ) 712, 816.

Fluorescence (tetrahydrofuran) ($\lambda_{max}$(nm)): 800.

EXAMPLE 99

Synthesis of Silicon (IV)2,3-naphthalocyanine bis (tert-butyldimethylsilyloxide)

A mixture of silicon naphthalocyanine dihydroxide, tert-butyldimethylchlorosilane (390 mg), imidazole (180 mg) and dimethylformamide (5 ml) was stirred at 150° C. for 30 minutes. The resultant was chromatographed on a silica gel (70–230 mesh, 60 Å)column (2×50 cm) equilibrated in hexane. The product was eluted sequentially with hexane and toluene, vacuum dried and weighed (6 mg).

UV-vis (tetrahydrofuran) ($\lambda_{max}$(nm)): 772,730, 686.

Fluorescence (tetrahydrofuran) ($\lambda_{max}$(nm)): 775.

$^1$H-NMR (500 MHZ, CDCl$_3$) δ 10.14 (s,8H), 8.67(m,8H), 7.90(m,8H), −1.20(s,18H), −2.60(s,12H)

EXAMPLE 100

Synthesis of Silicon(IV) phthalocyanine bis(tert-butyl-dimethylsilyloxide)

A mixture of Silicon(IV) phthalocyanine dihydroxide (200 mg), tert-butyldimethylchlorosilane (525 mg), imidazole (272 mg) and dimethylformamide (5 ml) was stirred at 150° C. for 30 minutes. The resultant was chromatographed on a silica gel (70–230 mesh, 60 Å)column (2×50 cm) equilibrated in hexane. The product was eluted sequentially with hexane and toluene, vacuum dried and weighed (12 mg).

UV -vis (tetrahydrofuran) ($\lambda_{max}$(nm)) 666,636,600.

Fluorescence (tetrahydrofuran) ($\lambda_{max}$(nm)): 671.

$^1$H-NMR (500 MHZ, CDCl$_3$) δ 9.65(m,8H), 8.33(m,8H), −1.45(s,18H),−2.98(s,12H)

EXAMPLE 101

Synthesis of [$2^1,2^2$-dichlorobenzo[b]-7,12,17-tri(2, 3-naphtho) [g,l,q]-5,10,15,20,-tetraazoporphyrinato] silicon dihydroxide (abbreviated as: Silicon [tri(2,3-naphthalocyanine)12,3-dichlorophthalocyanine dihydroxide)

Silicon tetrachloride (600 μL) was added to a mixture of 5,6-dichloro 1,3-diiminoisoindoline (100 mg) and 1,3-diiminobenz[f]isoindoline(466 mg) in freshly distilled quinoline (4 ml) under an argon atmosphere and the mixture heated with stirring at 210° C. for 2 hours. The resultant was allowed to cool, treated with water (20 ml) and refluxed for 20 minutes. The mixture was cooled, treated with ether (10 ml) and filtered, the solid was washed sequentially with water (2×20 ml), ether (3×20 ml), methylene chloride (10 ml) and acetone (20 ml). The solid was vacuum dried and weighed (0.83 g). The crude product was used without purification for the next step.

EXAMPLE 102

Synthesis of [$2^1$, $2^2$-dichlorobenzo[b]-7,12,17-tri(2, 3-naphtho)[g,l,q]-5,10,15,20,-tetraazoporphyrinato] silicon bis(7-oct-1-enyldimethylsilyloxide) (abbreviated as: Silicon[tri(2,3-naphthalocyanine)] 2,3-dichlorophthalocyanine bis (dimethylhexylvinylsilyloxide))

A mixture of silicon[tri(2,3-naphthalocyanine)2,3-dichlorophthalocyanine dihydroxide (400 mg) and 7-oct-1-enyldimethylchlorosilane (1.5 ml) was stirred at room temperature for 15 hours. The resultant was concentrated under vacuum on the rotary evaporator. The residue was chromatographed on a silica gel (70–230 mesh, 60 Å) column (2×50 cm) equilibrated in hexane. The product was eluted with toluene, vacuum dried and weighed (35 mg).

UV-vis (tetrahydrofuran) ($\lambda_{max}$(nm)ε(M$^{-1}$cm$^{-1}$)) 770, 728, 688, 654, 182000.

Fluorescence (tetrahydrofuran) ($\lambda_{max}$(nm)): 774, 727.

EXAMPLE 103

Synthesis of [$2^1,2^2$-dichlorobenzo[b]-7,12,17-tri(2, 3-naphtho) [g,l,q]-5,10,15,20,-tetraazoporphyrinato] silicon bis [dimethylpentafluorophenylsilyloxide)] (abbreviated as: Silicon [tri (2,3-naphthalocyanine)] 2,3-dichlorophthalocyanine bis (dimethylpentafluorophenylsilyloxide))

A mixture of silicon [tri(2,3-naphthalocyanine)]2,3-dichlorophthalocyanine dihydroxide (400 mg), chlorodimethylpentafluorophenylsilane (1.0 ml), imidazole 270 mg) and dimethylformamide (5 ml) was stirred at room temperature for 16 hours. The reaction mixture was filtered, washing the solid with dimethylformamide(4×2 ml). The filtrate was evaporated under vacuum on the rotary evaporator. The residue was dissolved in toluene and filtered. The filtrate was concentrated under vacuum on the rotary evaporator. The residue was chromatographed on a silica gel (70–230 mesh, 60 Å)column (2×50 cm) equilibrated in hexane. The product was eluted sequentially with hexane and toluene, vacuum dried and weighed (34 mg).

UV-vis (tetrahydrofuran) ($\lambda_{max}$(nm)$\epsilon$(M$^{-1}$cm$^{-1}$):780, 736, 696, 662; 142000.

Fluorescence (tetrahydrofuran) ($\lambda_{max}$(nm)): 735, 784 nm.

EXAMPLE 104

Synthesis of [$2^1,2^6,12^1,12^6$-tetraphenyldinaphtho[b, 1]-7, 17-di (2,3-naphtho) [-g,q]-5,10,15,20-tetraazoporphyrinato]silicon bis (7-oct-1-enyldimethylsilyloxide) (abbreviated as: Silicon [di (1,6-diphenylnaphthalocyanine)]dinaphthalocyanine bis (dimethylhexylvinylsilyloxide))

A mixture of silicon[di(1,6-diphenylnaphthalocyanine)] di-2,3-naphthalocyanine dihydroxide (25 mg) and 7-oct-1-enyldimethychlorosilane(60 μL), imidazole (16 mg) and dimethylformamide (4 ml) was stirred at room temperature for 3 days. The resultant was concentrated under vacuum on the rotary evaporator. The residue was chromatographed on a silica gel (70–230 mesh, 60 Å) column (2×50 cm) equilibrated in hexane. The product was eluted sequentially with hexane and toluene, vacuum dried and weighed (15 mg). This compound has also been isolated as a by-product during the chromatographic purification in Example 75.

UV-vis (tetrahydrofuran) ($\lambda_{max}$(nm)$\epsilon$(M$^{-1}$cm$^{-1}$): 786, 440000.

Fluorescence (tetrahydrofuran) ($\lambda_{max}$(nm)): 792.

$^1$H-NMR(500 MHZ, CDCl$_3$): δ −2.9(S,1211);−2.0(m,4H) 1.07(m,4H), −0.06(m,4H),0.17(m,4H), 0.6(m,4H), 1.4(m, 4H), 4.7(m,4H), 5.3(m,2H), 7.8(m,8H), 8.03(m,16H),8.15 (m,4H), 8.38(m,8H), 8.8 (m,4H).

EXAMPLE 105

Synthesis of [$2^1,2^6,12^1,12^6$-tetraphenyldinaphtho[b, 1]-7,17-di(2,3-naphtho)[g,q]-5,10,15,20-tetraazoporphyrinato]silicon dihydroxide (abbreviated as:Silicon[di(1,6-diphenylnapththalocyanine)]dinaphthalo cyanine dihydroxide))

Silicon tetrachloride (600 μL)was added to a mixture of 4,9-diphenyl 1,3-diiminobenz[f]isoindoline (1.0 g) and 1,3 diiminobenz[f]isoindoline (50 mg) in freshly distilled quinoline (7 ml) under an argon atmosphere and the mixture heated with stirring at 210° C. for 2 hours. The resultant was allowed to cool, treated with water (10 ml) and refluxed for 15 minutes. The mixture was cooled, treated with ether (20 ml) and filtered. The organic layer of the filtrate was washed with 1N hydrochloric acid (2×20ml). The solid was washed with methylene chloride (5×20ml). The organic phases were combined and evaporated with a rotary evaporator. The residue was chromatographed on a silica gel (70–230 mesh, 60 Å) column (2×50 cm) equilibrated in methylene chloride. The product was eluted with toluene—10% isopropanol, vacuum dried and weighed (25 mg).

UV-vis (methylene chloride) ($\lambda_{max}$(nm): 794.

EXAMPLE 106

Synthesis of Silicon (IV) phthalocyanine bis(7-oct-1-enyl dimethylsilyloxide (abbreviated as: Silicon phthalocyanine bis(dimethylhexylvinyloxide))

A mixture of silicon phthalocyanine dihydroxide 500 mg), 7-oct-1-enyldimethylchlorosilane (2.5 ml), imidazole (680 mg)and dimethylformamide(10 ml) was stirred at room temperature for 48 hours. The resultant was evaporated under vacuum on the rotary evaporator. The residue was dissolved in toluene (20 ml) and filtered. The solid washed with toluene(40 ml). The filtrate was concentrated under vacuum on the rotary evaporator and was chromatographed on a silica gel (70–230 mesh, 60 Å)column (2×50 cm) equilibrated in hexane. The product was eluted sequentially with hexane and toluene, vacuum dried and weighed (324 mg).

UV-vis (tetrahydrofuran) ($\lambda_{max}$(nm)$\epsilon$(M$^{-1}$cm$^{-1}$): 668, 636,660, 283000

Fluorescence (tetrahydrofuran) ($\lambda_{max}$(nm)): 673 $^{1H-NMR}$ (500 MHZ, CDCl$_3$): δ −2.8 (s, 12H), −2.27 (m, 4H), −1.33 (m,4H), −0.20(m,4H), 0.31 (m,4H), 0.84(m,4H), 1.54 (m,4H), 1.80 (m,4H), 4.94 (m,4H), 5.75 (m,2H), 8.3 (m,8H), 9.65 (m,8H)

EXAMPLE 107

Synthesis of Silicon (IV) phthalocyanine (10-carbomethoxy decyldimethylsilyloxide) (dimethylvinylsilyloxide)

A mixture of silicon(IV) phthalocyanine dihydroxide (500 mg), imidazole (300 mg), dimethylformamide (6 ml) and a mixture of (10-carbomethoxydecyldimethylchlorosilane (590 mg) and chlorodimethylvinylsilane (250 mg) was added and the reaction mixture stirred at room temperature for 24 hours. The resultant was concentrated under vacuum on the rotary evaporator. The residue was chromatographed on a silica gel (70–230 mesh, 60 Å)column (2×50 cm) equilibrated in hexane. The products (a) Silicon (IV) phthalocyanine bis(10-carbomethoxy decyldimethyl silyloxide) (100 mg) and (b) silicon(IV) phthalocyanine (10-carbomethoxydecyldimethylsilyloxide) (dimethylvinylsilyloxide) (68 mg) were eluted with toluene.

(a) UV-vis (tetrahydrofuran) ($\lambda_{max}$(nm): 666,638,602.

Fluorescence (tetrahydrofuran) ($\lambda_{max}$(nm)): 671.

$^{-1}$H-NMR(500 MHZ, CDCl$_3$): δ −2.90(s,12H),2.27(m, 4H) −1.35(m,4H), −0.22(m,4H), 0.25(m,4H), 1.18 (m, 4H), 1.0(m,4H), 0.70 m,4H)1.65(m,4H), 2,35(m,4H), 3.7(s,6H), 8.33(m,8H), 9.64(m,8H).

(b) UV-vis (tetrahydrofuran) ($\lambda_{max}$(nm)): 668, 636,602.

Fluorescence (tetrahydrofuran) ($\lambda_{max}$(nm)): 673.

$^1$H-NMR(500 MHZ, CDCl$_3$): δ −2.9 (s,6H), −2.75 (s,6H) −2.27(m,4H), −1.36(m,4H), −0.015(m,4H), 0.027 (m,4H), 0.07 m,4H),0.10 (m,4H), 1.21 (m,4H), 1.65 (m,3H), 2,33 (m,3H);3.0(m,1H), 3.4(m,1H), 3.6(s), 3.7(s), 4.26(m,1H) ;8.33(m,8H), 9.6(m,8H).

EXAMPLE 108

Synthesis of Sulfo[$2^1,2^6,12^1,12^6$-tetraphenyldinaphtho[b,l]-7,17-dibenzo[g,q]-5,10,15, 20-tetraazoporphyrinato]silicon dihydroxide (abbreviated as: Sulfo Silicon di[(1,6-diphenyl)-2 3-naphthalocyaninel diphthalocyanine dihydroxide)

A mixture of Silicon di[(1,6-diphenyl)-2,3-naphthalocyanine]diphthalocyanine)dihydroxide (0.2 g) and chloroform (2 ml) was stirred at room temperature for 10 minutes under an argon atmosphere. The mixture was then cooled in an ice-bath and chlorosulfonic acid (2 ml) was added. The mixture was stirred in the ice-bath for 15 minutes and then at room temperature for 20 minutes. The mixture was then refluxed for 2 hours, cooled and poured onto crushed ice (100 g). The resulting green mixture was extracted with chloroform (2×30 ml). The combined organic layers were washed with water (20 ml), dried (MgSO$_4$) and evaporated with a rotary evaporator. The brown residue was treated with 6N potassium hydroxide (3 ml) with swirling and after 5 minutes the mixture was partitioned between water (40 ml) and ether (20 ml). The aqueous layer was acidi[ied with 1N hydrochloric acid (15 ml), washed with ether (40 ml) and evaporated with a rotary evaporator. The residue was vacuum dried and weighed (8 mg).

UV-vis (methanol) (($\lambda_{max}$(nm)): 650, 658, 692, 726, 748 (sh).

UV-vis(water) (($\lambda_{max}$(nm)): 654, 662, 732, 758 (sh)

Fluorescence (water) (($\lambda_{max}$(nm)): 773.

IR(KBr) (cm$^1$):3153, 1720, 1405, 1225, 1182, 1037, 1014, 622.

EXAMPLE 109

Synthesis of Acetylthiopropionic Acid

To a stirred solution of 3-mercaptopropionic acid (7 ml), and imidazole (5.4 g) in tetrahydrofuran (700 ml) was added, dropwise, over 15 minutes, under argon, a solution of 1-acetylimidazole (9.6 g) in tetrahydrofuran (100 ml). The solution was allowed to stir a further 3 hours at room temperature after which time the tetrahydrofuran was removed under vacuum. The residue was treated with ice-cold water (18 ml) and the resulting solution acidified with ice-cold concentrated hydrochloric acid (14.5 ml) to pH 1.5–2.0 The mixture was extracted with diethyl ether (2×50 ml), the ether was washed with water (2×50 ml) and dried over MgSO$_4$ and evaporated. The residual crude yellow oily solid product (10.5 g) was recrystallized from chloroform-hexane to afford 4.8 g (41% yield) acetylthiopropionic acid as a white solid with a melting point of 44°–45° C.

EXAMPLE 110

Synthesis of [$2^1,2^6,12^1,12^6$-tetraphenyldinaphtho[b, l]7,17-dibenzo[g,q]-5,10,15,20-tetraazoporphyrinato]silicon [poly(ethylene glycol)] thiopropionyl poly(ethylene glycol)](abbreviated as: Silicon di[(1,6-diphenyl)-2,3-naphthalocyaninel diphthalocyanine rpoly(ethylene glycol)]poly (ethylene glycol)thiopropionate])

A solution of silicon di[(1,6-diphenyl)-2,3-naphthalocyanine]diphthalocyanine[poly(ethyleneglycol thiopropionate] in 0.12M potassium carbonate in 80% methanol (1 ml) was allowed to stand at room temperature for 5 minutes. The pH of the solution was then adjusted to 7 by dropwise addition of a solution of 0.5M potassium phosphate pH 7 which was made 1N in hydrochloric acid. The thiol content of the solution was estimated by Ellman's method using dithionitrobenzoic acid. The title compound in solution is capable of being conjugated to ligand analogues, proteins, polypeptides and nucleic acids containing for example, maleimide or alkyliodide functional groups.

EXAMPLE 111

Synthesis of 2(2-amino-4-thiolbutanoic acid thiolactone)-bromoacetamide(abbreviated as: bromoacetyl-HCTL)

Bromoacetic acid (1.0 g), homocysteine thiolactone hydrochloride (1.1 g) and pyridine (1.2 ml) were dissolved in anhydrous dimethylformamide (36 ml) and 1-(3-dimethylaminopropyl)-3-ethylcarbodiimide hydrochloride (1.52 g) was added. The reaction was stirred at room temperature for 18 hours. The solvents were removed under vacuum, ethanol (10 ml) was added to dissolve the residue and then the ethanol was removed under vacuum Ethanol (10 ml) was again added to dissolve the residue and was again removed under vacuum. Water (20 ml) was added to the oil and the aqueous solution was extracted 3 times with methylene chloride (45 ml). The combined organic extracts were dried over anhydrous magnesium sulfate. The solution was filtered and the solvent was removed under vacuum to give a clear oil. Diethyl ether (5 ml) was added and the resulting precipitate was collected and washed on a fritted funnel. The precipitate was dried under vacuum and 1.0 g of the title compound was recovered.

EXAMPLE 112

Synthesis of [2-naphtho[b]-7,12,17-tribenzo[g,l,q]-5,10,15,20-tetraazoporphyrinato]silicon dihydroxide (abbreviated as: Silicon (IV) [tri (phthalo) naphthalocyanine]hydroxide Silicon tetrachloride (912 $\mu$L) was added to a mixture of 1,3-diiminoisoindoline (1.0 g) and 1,3-diiminobenz[f] isoindoline (0.25 g) in freshly distilled quinoline (3 ml) under an argon atmosphere and the mixture heated with stirring at 210° C. for 2 hours. The resultant was allowed to cool, treated with water (25 ml) and refluxed for 15 minutes. The mixture was cooled, the solid filtered, washing the solid sequentially with water (3×10 ml) and ether (5×10 ml). The solid was vacuum dried and weighed (1.5 g).

EXAMPLE 113

Synthesis of [2-naphtho[b]-7,12,17-tribenzo[g,l,q]-5,10,15,20-tetraazoporphyrinato]silicon bis (7-oct-1-enyldimethyl silyloxide) (abbreviated as: Silicon [tri(phthalo)naphthalocyanine] bis (dimethvlhexylvinylsilyloxide))

A mixture of Silicon (IV) [tri(phthalo)naphthalocyanine dihydroxide (1.0 g). 7-oct-1-enyldimethylchlorosilane (3.0 ml), imidazole (0.68 g) and dimethylformamide (10 ml) was stirred at room temperature for 24 hours. The resultant was concentrated under vacuum on the rotary evaporator. The residue was chromatographed on a silica gel (70–230 mesh 60 Å°) column (2×50 cm) equilibrated in hexane. The product was eluted sequentially with hexane and hexane—3% toluene, vacuum dried and weighed (11 mg).

UV-vis(methylene chloride) (($\lambda_{max}$(nm)): 716, 704, 684, 648, 618

Fluorescence (methylene chloride) ( ($\lambda_{max}$(nm)): 710

$^1$H-NMR(500 MHz, CDCl$_3$): δ −2.8(s,12H), −2.2(m,4H), −1.23(m,4H), −0.16(m,4H), 0.27(m,4h), 0.78(m,4H), 1.7(m, 4H), 4.9(m,4H), 5.7(m,2H), 7.94(m,2H), 8.3(m,6H), 8.7(m, 2H), 9.6(m,6H), 10.1(S,2H).

EXAMPLE 114

Synthesis of Sulfo[2$^1$,2$^6$,12$^1$,12$^6$-tetraphenyldinaphtho[b,l]7,17-dibenzo[g,q]-5,10,15, 20-tetraazoporphyrinato]silicon[N-(2-butyrothiolactone)amidomethoxide]hydroxide (abbreviated as Sulfo silicon di[(1,6-diphenyl)-2,3-naphthalocyanine]-diphthalocyanine[-2-butyrothiolactone)amidomethoxide]hydroxide A mixture of sulfo silicon di[(1,6-diphenyl)-2,3-naphthalocyanine]diphthalocyanine dihydroxide (200 mg), bromoacetyl homocysteine thiolactone (7 mg) and powdered potassium carbonate (180 mg), in dimethylformamide (2 ml) was stirred under argon at room temperature for 24 hours. The solvent was evaporated with a rotary evaporator, the residue treated with ethanol (2 ml) and filtered washing with ethanol (2 ml). The filtrate was evaporated, and the product vacuum dried and weighed ( 200 mg). This product was used without further purification in the next step.

EXAMPLE 115

Synthesis of Sulfo[2$^1$,2$^6$,12$^1$,12$^6$-tetraphenyldinaphtho[b,l]7,17-dibenzo[g,q]-5,10,15, 20-tetraazoporphyrinato]silicon[N-(cysteine) amidomethoxide]hydroxide (abbreviated as: Sulfo silicon di[(1,6-diphenyl)-2,3-naphthalocyanine] diphthalocyanine[N-(cysteine)amidomethoxide] hydroxide)

A solution of sulfo silicon di[(1,6-diphenyl-2,3-naphthalocyanine]diphthalocyanine[N-(2-butyrothiolactone)amidomethoxide]hydroxide(10mg) in water (182 ml) was treated with 1N potassium hydroxide solution (46 ml) and allowed to stand at room temperature for 10 minutes. The pH of the solution was then adjusted to 7 by dropwise addition of a solution of 0.5M potassium phosphate pH 7 which was made 1N in hydrochloric acid. The thiol content of the solution was estimated by Ellman's method using dithionitrobenzoic acid. The title compound in solution is capable of being conjugated to ligand analogues, proteins, polypeptides and nucleic acids containing, for example, maleimide or alkyl iodide functional groups.

EXAMPLE 116

Synthesis of Silicon tetra-tert-butylphthalocyanine bis [(4-aminobutyl) dimethylsilyloxide]

To a stirred solution of silicon tetra-tert-butyl phthalocyanine dihydroxide (800 mg) in pyridine (140 ml) was added 4-aminobutyldimethylmethoxysilane (950 µL). The solution was heated to reflux and pyridine allowed to distill off until 50 ml of distillate had been collected. The solution was allowed to cool and the residual pyridine removed under vacuum. The residue was chromatographed on a silica gel (70–230 mesh, 60 Å, 3×50 cm) column equilibrated in methylene chloride. The product was eluted sequentially with methylene chloride, tetrahydrofuran and finally tetrahydrofuran—2% triethylamine. The dark blue product was vacuum dried and weighed (355 mg).

UV-vis (tetrahydrofuran) ($\lambda_{max}$(nm)): 606, 644, 672.

EXAMPLE 117

Synthesis of Sulfo[2$^1$,2$^6$,12$^1$,12$^6$-tetraphenyldinaphtho[b,l]-7,17-dibenzo[g,q]-5,10,15, 20-tetraazoporphyrinato]silicon dihydroxide (abbreviated as: Sulfo Silicon di[(1,6-diphenyl)-2,3-naphthalocyanine] diphthalocyanine dihydroxide)

Silicon di[(1,6-diphenyl)-2,3-naphthalocyanine] diphthalocyanine dihydroxide (110 mg) was dissolved in (1 ml) concentrated sulfuric acid, and 10 minutes later chlorosulfonic acid (150 ml) was added. The reaction mixture was then heated in an oil bath (100°–130° C.) for 2.5 hours. The reaction mixture was allowed to cool to room temperature and poured onto crushed ice (30 g). The pH of the green solution was adjusted with solid potassium carbonate to pH=9.0. The solvent was evaporated with a rotary evaporator. The residue was dissolved in 200 mM potassium phosphate buffer (pH=7.0) and applied to a C$_{18}$-column (12 cm×2.5 cm) that was equilibrated in 200 mM potassium phosphate buffer (pH=7.0). The column was washed with 200 mM potassium phosphate buffer (pH =7.0) (50 ml) water (300 ml), and the product was eluted with a mixture of water and methanol 2:1 (v/v). The solvent was evaporated with a rotary evaporator. The residue was vacuum dried and weighed (137 mg).

UV-vis (Water) ($\lambda_{max(nm)}$) 658, 698, 732, 756(sh).

UV-vis (Methanol) ($\lambda_{max(nm)}$) in neoH=648, 688, 724, 742(sh)

IR(KBr) (cm$^{-1}$) 3629, 3465, 3065, 2593, 1721, 1622, 1521, 1422, 1353, 1335, 1284, 1194, 1088, 1039, 1013, 941, 906, 821, 760, 651, 620.

$^1$H-NMR (500 MHZ, DMSO-d$_6$) δ=−2.4(s, OH), 8.1(m, Ar—H).

EXAMPLE 118

Synthesis of Sulfo[2$^1$,2$^6$,12$^1$,12$^6$-tetraphenyldinaphtho[b,l]-7,17-dibenzo[g,q]-5,10,15, 20-tetraazoporphyrinato]silicon bis (4-Aminobutyl dimethylsilane) (abbreviated as: Sulfo Silicon di[(1, 6-diphenyl-2,3-naphthalocyanine) phthalocyanine] bis (4-Aminobutyl dimethylsilane)

To a suspension of sulfo silicon di[(1,6-diphenyl-2–3-naphthalocyanine)phthalocyanine] dihydroxide (32 mg) in pyridine (20 ml) was added 4-aminobutyldimethylmethoxysilane (50 ml), and the reaction mixture was heated in an oil bath (140° C.) for 3 hours. The reaction mixture was allowed to cool to room temperature, and DMF(5 ml) was added followed by 4-aminobutyl-dimethylmethoxy-silane (100 ml). The reaction mixture was then refluxed for 16 hours. After cooling the solvent was evaporated with a rotary evaporator. The residue was dissolved in methanol (2 ml) and applied on a C$_{18}$ column. The column was washed with (200 mM) potassium phosphate buffer pH=7.0 (20 ml), water (200 ml), water/methanol=3:1 (v/v) (40 ml), water/methanol=2:1 (v/v) (40 ml). The product was eluted with 95% methanol, the solvent was evaporated with a rotary evaporator, and the product was dried under vacuum and weighed (32 mg).

UV-vis (Water) ($\lambda_{max(nm)}$) 658, 696(sh), 730.

UV-vis (Methanol) ($\lambda_{max(nm)}$) 648, 686, 722, 748(sh)

EXAMPLE 119

Synthesis of Sulfo[2$^1$,2$^6$,12$^1$,12$^6$-tetraphenyldinaphtho[b,l]-7,17-dibenzo[g,q]-5,10,15, 20-tetraazoporphyrinato]silicon bis (3-aminopropyldiisopropylsilyloxide) (abbreviated as: Sulfo Silicon di[(1,6-diphenyl-2,3-naphthalocyanine) phthalocyanine] bis- (3-aminopropyldiisopropylsilyloxide)

A mixture of sulfo silicon di[(1,6-diphenyl)-2–3-naphthalocyanine]phthalocyanine dihydroxide (50 mg)

3-amino-propyldiisopropylmethoxysilane (190 microliters) in toluene (2 ml) was refluxed for 16 hours. After cooling to room temperature the solvent was evaporated with a rotary evaporator. The green oily residue was applied to a $C_{18}$ column. The column was washed with (200 mM) phosphate buffer (pH=7.0) (50 ml), water (200 ml), water/methanol [(3:1;(v/v) (20 ml)], water/methanol 2:1 (v/v). The product was eluted with 95% methanol. The solvent was evaporated with a rotary evaporator, and the residue was vacuum dried and weighed (40.0 mg).

UV-vis (Methanol) ($\lambda_{max(nm)}$): 648, 686, 724, 744(sh).

EXAMPLE 120

Synthesis of Sulfo[$2^1,2^6,12^1,12^6$-tetraphenyldinaphtho[b,l]-7,17-dibenzo[g,q]-5,10,15, 20-tetraazoporphyrinato]silicon bis-[(10-carbomethoxy decyl) dimethylsilyloxide] (abbreviated as: Sulfo Silicon di[(1,6-diphenyl)-2,3-naphthalocyanine]diphthalocyanine bis-[(10-carbomethoxydecyl) dimethylsilyloxide]

A mixture of imidazole (33 mg) and (10-carbomethoxydecyl) dimethylchlorosilane in (1.0 ml) pyridine was stirred for 1 hour at room temperature, and sulfo silicon di[(1,6-diphenyl)-2-3-naphthalocyanine] diphthalocyanine dihydroxide (20 mg) in pyridine (3 ml) was added. After stirring the reaction mixture for 16 hours, the pyridine was evaporated with a rotary evaporator. The residue was triturated with (2 ml) (200 mM) potassium phosphate buffer, PH=7.0 (2 ml) (200 mM) and applied to $C_{18}$ column (equilibrated with (200 mM) potassium phosphate buffer pH=7.0). The column was washed with potassium phosphate buffer (60 ml) (200 mM) (pH 7.0), water (210 ml), water/MeOH [(1:1;(v/v) (40 ml)], and water/MeOH [(1:2; (v/v) (35 ml)]. The product was then eluted with 95% methanol, the solvent was evaporated with a rotary evaporator. The residue was vacuum dried and weighed (8 mg)

UV-vis (Water) ($\lambda_{max(nm)}$) 658, 694, 730, 750, (sh)

UV-vis (Methanol) ($\lambda_{max(nm)}$) 650, 690, 726, 746(sh)

IR(KBr) (cm$^{-1}$) 2924,2854,1744.

Fluorescence (methanol) λmax(nm):752

Fluorescence (water) λmax(nm): 761

EXAMPLE 121

Synthesis of Sulfor[$2^1,2^6,12^1,12^6$-tetraphenyldinaphtho[b,l]-7,17-dibenzo[g,q]-5,10,15, 20-tetraazoporphyrinato]silicon bis (7-oct-1-enyldimethylsilyloxide) (abbreviated as: Sulfo Silicon di[(1,6-diphenyl)-2,3-naphthalocyanine] diphthalocyanine bis (7-oct-1-enyldimethylsilyloxide)

A mixture of sulfa silicon di[(1,6-diphenyl)-2-3-naphthalocyanine]diphthalocyanine dihydroxide (10 ml) and imidazole (41 mg) in dimethylformamide (2 ml) was stirred at room temperature for 10 minutes and 7-oct-1-enyldimethylchlorosilane was added. The mixture was stirred for 14 hours at room temperature and the solvent was removed with a rotary evaporator. The residue was triturated with (2 ml) (200 mM) potassium phosphate buffer pH=7.0 and applied to a $C_{18}$ column (equilibrated with 200 mM potassium phosphate buffer, pH=7.0). The column was washed with potassium phosphate buffer (40 ml), water (150 ml) and water/methanol (2:1 (v/v)). The product was eluted with 95% methanol, and the solvent was evaporated with a rotary evaporator. The residue was vacuum dried and weighed (9 mg).

$^1$H-NMR (500 MHZ, DMSO) δ -2.8(s,12H), -2.1(m,4H), -1.3(m,4H), -0.23(m,4H), 0.06(m,4H), 0.5(m,4H), 1.3(m, 4H), 4.7(m,4H), 5.4(m, 2H), 8.0(Ar—H)

EXAMPLE 122

Synthesis of Sulfo silicon naphthalocyanine bis( 4-aminobutyldimethyl silyloxide A mixture of sulfa silicon naphthalocyanine dihydroxide triethyl ammonium salt (30 mg) and pyridine was stirred at room temperature for 10 minutes, and then N,N-Diisopropylethylamine (10 ml) followed by 4-aminobutyldimethylmethoxysilane (380 microliters) were added. The reaction mixture was heated in an oil bath for 2 hours at 130° C. After cooling to room temperature the solvent was removed with a rotary evaporator and the residue was triturated with 200 mM potassium phosphate buffer pH=7.0 (2 ml) and applied to a $C_{18}$ column (1.5×23 cm filled with $C_{18}$ to 7.0 cm height). The column was washed with 200 mM potassium phosphate buffer (40 ml), water (80 ml), water/methanol (2:1) (40 ml), water/methanol (2:1) (70 ml), and the major green fraction was eluted with water/methanol (1:3) (40 ml). The solvent was removed with a rotary evaporator and the residue was vacuum dried and weighed (14 mg).

IR(KBr) (cm $^{-1}$) 3069, 2964, 1631, 1528, 1362, 1252, 1184, 1091, 1067, 1035, 844, 798, 761, 728, 691, 615.

$^1$H-NMR (500 MHZ, DMSO) δ -2.5(S,12H), -1.9(m, 4H), -1.0(m,4H), 0.4 (m, 4H), 2.0 (m, 4H)

EXAMPLE 123

Synthesis of Sulfo silicon naphthalocyanine bis [10-(carbomethoxy)decyldimethylsiloxide]

To a stirred solution of imidazole (109 mg) in pyridine (2 ml) was added 10-(carbomethoxy) decyldimethylchlorosilane (513 microliters), and the mixture stirred for 20 min. at room temperature. Sulfo silicon naphthalocyanine dihydroxide (60 mg) (neat) was then added followed by pyridine (1 ml) and 10-(carbomethoxy) decyldimethylchlorosilane (0.6 ml). The reaction mixture was allowed to stir 14 hours, and the solvent evaporated with a rotary evaporator. The residue was suspended in 40 mM potassium phosphate buffer (pH 7.0) (2 ml) and chromatographed on a $C_{18}$ column. After washing the column with 200 mM potassium phosphate buffer (40 ml) and water (300 ml), the product was eluted with water/methanol (1:1). The solvent was evaporated with a rotary evaporator. The residue was vacuum dried and weighed (55 mg).

EXAMPLE 124

Synthesis of sulfo silicon naphthalocyanine bis(3-aminopropyldiisopropylsilane)

A mixture of sulfo silicon napthalocyanine (50 mg) and 3-aminopropyldiisopropylethoxysilane (200 ml) in toluene (3 ml) is refluxed for 16 hours. The reaction mixture is allowed to cool to room temperature and the solvent is evaporated with a rotary evaporator. The residue can be purified on a $C_{18}$ column, with (200 mM) potassium phosphate buffer, (pH=7.0) water and 95% methanol.

EXAMPLE 125

Synthesis of 1,4-diphenylnaphthalene -2,3-di-carbonitrile

In a dry 2L 3-necked round bottom flask equipped with a magnetic stirring bar, dropping funnel, gas inlet tube attached to an argon gas cylinder, was placed tetrahydro-1, 4-diphenyl-1,4-epoxy-napthalene-2,3-dicarbonitrile (20 g) and dry tetrahydrofuran (450 ml) while purging the flask with argon gas. The mixture was stirred for 20 minutes. The flask was cooled to −78° C. (acetone/dry ice) and Lithium bis(trimethylsilyl)-amide (150 ml, 1.0M THF) was added dropwise over 2 hours. The mixture was allowed to stir at this temperature, and saturated ammonium chloride (300 ml) was added. The mixture was allowed to warm to room temperature, and the white solid was filtered off. The organic layer of the filtrate was separated. The aqueous layer was washed with ether (100 ml). The combined organic layers were dried (magnesium sulfate). After the magnesium sulfate was filtered off, the solvent was evaporated with a rotary evaporator, the residue triturated with ether, and the solid filtered, dried under vacuum and weighed (17 g.)

IR(KBr) (cm$^{31}$ $^1$) 3059, 2232, 1608, 1494, 1446, 1400, 1378, 1183, 1077, 1029, 1001, 931, 796, 783, 757, 706, 681, 657, 620, 517, 437.

$^1$H-NMR (500 MHZ, DMSO) δ 7.5(m,4H), 7.6(m,8H), 7.8(m,2H).

EXAMPLE 126

Synthesis of Sulfo[$2^1,2^6,12^1,12^6$-tetraphenyldinaphtho[b,l]-7,17-dibenzo[g,q]-5,10,15, 20-tetraazoporphyrinato]silicon bis[N-succinamido) aminobutyldimethyl silyloxide A mixture of sulfo silicon di[(1,6-diphenyl)-2,3-napthalocyanine]diphthalocyanine bis (4-aminobutyldimethylsilyloxide) (20 mg) and succinic anhydride (50 mg) in dimethylformamide (4 ml) is refluxed for 2 hours. The reaction mixture is allowed to cool to room temperature and the solvent is evaporated with a rotary evaporator. The residue can be purified on a C$_{18}$ column, with (200 mM) potassium phosphate buffer, (pH 7.0), water and methanol.

EXAMPLE 127

Synthesis of Sulfo[$2^1,2^6,12^1,12^6$-tetraphenyldinaphtho[b,l]-7,17-dibenzo[g,q]-5,10,15, 20-tetraazoporphyrinato]silicon bis[4[ (acetylthiopropionamido)butyl] dimethylsilyloxidel (Abbreviated as: Sulfo Silicon di[(1,6-diphenyl)-2, 3-naphthalocyaninel diphthalocyanine bis ((acetylthiopropionamido)butyl silyloxide)

A mixture of sulfo silicon di[(1,6-diphenyl)-2,3-napthalocyanine]diphthalocyanine bis (4-aminobutyldimethylsilyloxide)in dimethylformamide and a solution of acetylthioproponic acid and 1,1'-Carbonyldiimidazole in dimethylformamide is stirred at room temperature for 1 hour. The solvent is evaporated with a rotary evaporator. The residue can be purified on a C$_{18}$ column, with (200 mM) potassium phosphate buffer (pH 7.0) water and methanol.

EXAMPLE 128

Synthesis of Sulfo[$2^1,2^6,12^1,12^6$-tetraphenyldinaphtho[b,l]-7,17-dibenzo[g,q]-5,10,15, 20-tetraazoporphyrinato]silicon bis[4[ (thiopropionamido)butyl]dimethylsilyloxide] (Abbreviated as: Sulfo Silicon di[(1,6-diphenyl)-2, 3-naphthalocyanine] diphthalocyanine bis ((thiopropionamido)butyl dimethyl silyloxide)

A mixture of sulfo silicon di[(1,6-diphenyl-2,3-naphthalocyanine] diphthalocyanine bis ((acetylthiopropionamido)butyl dimethyl silyloxide) in 50% (v/v) aqueous methanol (20 mM) and potassium carbonate at 200 mM is stirred at room temperature for 20 min. The mixture is neutralized to pH 7 with 1N hydrochloric acid and the solvent is evaporated with a rotary evaporator. The residue can be purified on a C$_{18}$ column, with (200 mM) potassium phosphate buffer (pH 7.0), water and methanol.

EXAMPLE 129

Preparation of a Conjugate of Sulfonated Hybrid Phthalocyanine Derivative and an Antibody A monoclonal antibody against human chorionic gonadotropin (Calbiochem, San Diego, Calif.) at 10 mg/ml in 50 mM potassium phosphate, 150 mM sodium chloride, pH 7.0, is reacted with SMCC (Pierce Chemical Co., Rockford, Ill.) at 0.6 mM at room temperature for 1.5 h. The antibody-maleimide is purified on a column of Sephadex G-25 equilibrated in 50 mM potassium phosphate, 150 mM sodium chloride, pH 7.0. The purified antibody-maleimide (2.5 ml) at 5 mg/ml is reacted with an excess of sulfo silicon di[(1,6-diphenyl-2,3-naphthalocyanine] diphthalocyanine bis ((thiopropionamido)butyl dimethylsilyloxide) (2.5 ml) at 0.6 mM at room temperature for 3 h. A solution of N-ethyl maleimide in water is then added to a final concentration of 3 mM and the solution is stirred for an additional 30 min. The antibody-hybrid phthalocyanine derivative is purified on a Sephadex G-25 column equilibrated in 50 mM potassium phosphate, 150 mM sodium chloride, 10 mg/ml bovine serum albumin, pH 7.0.

EXAMPLE 130

Preparation of a Conjugate of Sulfonated Hybrid Phthalocyanine Derivative and a Ligand Analogue In one embodiment the ligand analogue is morphine. Morphine-HCTL (see U.S. Pat. No. 5,089,391, example 4, incorporated by reference) is hydrolyzed in 0.12M potassium carbonate/40% (v/v) aqueous methanol at 20 mM at room temperature for 5 min. The solution is then adjusted to pH 7.0 with 1N hydrochloric acid and diluted to 5 mM with 50 mM potassium phosphate, pH 7.0. A homo bifunctional cross linker, (bis-maleimidohexane, Pierce Chemical Co., Rockford, Ill.) in 50 mM potassium phosphate, pH 7.0, is added to a final concentration of 50 mM. The solution is stirred at room temperature for 1 h and the morphine-maleimide derivative is purified on a reversed phase C$_{18}$, column using a linear gradient of 50 mM potassium phosphate, pH 7 and methanol. The morphine-maleimide solution in 50 mM potassium phosphate, pH 7.0, is added to a solution of sulfo silicon di[(1,6-diphenyl-2,3-naphthalocyanine] diphthalocyanine bis ((thiopropionamido)butyl dimethylsilyloxide) in 50 mM potassium phosphate, pH 7.0, so that the final concentrations are 10 mM and 2 mM, respectively. The solution is stirred at room temperature for 3 h and the sulfonated hybrid phthalocyanine-morphine derivative is purified on a reversed phase C$_{18}$ column using a linear gradient of 10 mM potassium phosphate, pH 7.0 and methanol.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to t hose skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications mentioned herein are incorporated herein by reference to describe and disclose specific information for which the reference was cited in connection with.

What is claimed is:

1. A water soluble hybrid phthalocyanine derivative.

2. A derivative of claim 1 wherein the derivative is silicon[di(1,6-diphenyl-2,3 naphthalocyanine)]diphthalocyanine bis [poly(ethylene glycol) methyl ether].

3. A derivative of claim 1 wherein the derivative is silicon[di(1,6-diphenyl-2,3-naphthalocyanine)]diphthalocyanine bis[poly(ethylene glycol)].

4. A derivative of claim 1 wherein the derivative is silicon [di(1,6-diphenyl-2,3-naphthalocyanine)]diphthalocyanine [poly(ethylene glycol)][poly(ethylene glycol) acetylthiopropionate].

5. A derivative of claim 1 wherein the derivative is silicon[di(1,6-diphenyl 2,3-naphthalocyanine)]di(2,3-dicarboxyphthalocyanine)dihydroxide.

6. A derivative of claim 1 wherein the derivative is silicon[di(1,6-diphenyl 2,3-naphthalocyanine)]di(2,3-dicarboxyphthalocyanine) bis[poly(ethylene glycol)methyl ether].

7. A derivative of claim 1 wherein the derivative is sulfo silicon di[(1,6-diphenyl-2,3-naphthalocyanine]diphthalocyanine dihydroxide.

8. A derivative of claim 1 wherein the derivative is silicon [di(1,6-diphenyl-2,3-naphthalocyanine)]diphthalocyanine [poly(ethylene glycol)][poly(ethylene glycol) thiopropionate].

9. A derivative of claim 1 wherein the derivative is sulfo silicon di[(1,6-diphenyl-2,3-naphthalocyanine] diphthalocyanine[-2-butyrothiolactone)amidomethoxide] hydroxide.

10. A derivative of claim 1 wherein the derivative is sulfo silicon di[(1,6-diphenyl-2,3-naphthalocyanine] diphthalocyanine[N-(cysteine)amidomethoxide]hydroxide.

11. A derivative of claim 1 wherein the derivative is silicon tetra-tert-butylphthalocyanine bis [(4-aminobutyl) dimethylsilyloxide].

12. A derivative of claim 1 wherein the derivative is sulfo[$2^1,2^6,12^1,12^6$-tetraphenyldinaphtho[b,1]-7,17-dibenzo[g,q]-5,10,15,20-tetraazoporphyrinato]silicon dihydroxide.

13. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis (4-Aminobutyldimethylsilyloxide).

14. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis (3-aminopropyldiisopropylsilyloxide).

15. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis-[(10-carbomethoxydecyl) dimethyl silyloxide].

16. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis (7-oct-1-enyldimethylsilyloxide).

17. A derivative of claim 1 wherein the derivative is sulfo silicon naphthalocyanine bis(4-aminobutyldimethyl silyloxide).

18. A derivative of claim 1 wherein the derivative is sulfo silicon naphthalocyanine bis [10-(carbomethoxy)decyl dimethylsilyloxide].

19. A derivative of claim 1 wherein the derivative is sulfo silicon naphthalocyanine bis(3-aminopropyldiisopropylsilyloxide).

20. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis[N-succinamido)aminobutyldimethyl silyloxide.

21. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis[4 [(acetylthiopropionamido)butyl] dimethylsilyloxide].

22. A derivative of claim 1 wherein the derivative is sulfo[$2^1,2^6,12^1,12^6$-tetraphenyldinaphtho[b,l]-7,17-dibenzo[g,q]-5,10,15,20-tetraazoporphyrinato]silicon bis[4 [(thiopropionamido)butyl] dimethylsilyloxide].

* * * * *